United States Patent
Menchen et al.

(10) Patent No.: US 6,716,994 B1
(45) Date of Patent: Apr. 6, 2004

(54) MOBILITY-MODIFYING CYANINE DYES

(75) Inventors: Steven M. Menchen, Fremont, CA (US); Scott C. Benson, Alameda, CA (US); Barnett B. Rosenblum, San Jose, CA (US); Shaheer H. Khan, Foster City, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/477,270

(22) Filed: Jan. 4, 2000

(51) Int. Cl.[7] .................. C07D 209/02; C09B 23/02
(52) U.S. Cl. .......................... 548/455; 430/581
(58) Field of Search ................ 548/455; 430/581

(56) References Cited

U.S. PATENT DOCUMENTS

| | | |
|---|---|---|
| 3,734,739 A | 5/1973 | Borror |
| 4,981,977 A | 1/1991 | Southwick et al. ......... 548/455 |
| 5,268,486 A | 12/1993 | Waggoner et al. ......... 548/427 |
| 5,321,130 A | 6/1994 | Yue et al. ................. 536/23.1 |
| 5,486,616 A | 1/1996 | Waggoner et al. ......... 548/217 |
| 5,569,587 A | 10/1996 | Waggoner ..................... 435/6 |
| 5,569,766 A | 10/1996 | Waggoner et al. ......... 548/150 |
| 5,627,027 A | 5/1997 | Waggoner ..................... 435/6 |
| 5,800,996 A | 9/1998 | Lee et al. ..................... 435/6 |
| 5,863,727 A | 1/1999 | Lee et al. ..................... 435/6 |
| 5,945,526 A | 8/1999 | Lee et al. ................. 536/26.6 |
| 6,004,536 A | 12/1999 | Leung et al. |

FOREIGN PATENT DOCUMENTS

| | | |
|---|---|---|
| WO | WO 96/13552 A | 5/1996 |
| WO | WO 97/13810 A | 4/1997 |
| WO | WO 97/40104 A | 10/1997 |
| WO | WO 99/05221 A | 2/1999 |

OTHER PUBLICATIONS

Brooker et al., 1945, "Absorption Spectra of Dyes with Heteroaromatic Nuclei—Color and Constitution. Part VII, Interpretation of Absorptions of Dyes Containing Heterocyclic Nuclei of Different Basicities," *J. Am. Chem. Soc.* 67:1875:1889 (in particular at p. 1878).

Schäfer, Ed., 1973, "Dye Lasers," *Topics in Applied Physics*. 4:144–193, Springer–Verlag, New York, Heidelberg, Berlin.

Tu et al., 1998, "The influence of fluorescent dye structure on the electrophoretic mobility of end–labeled DNA," *Nucl. Acids Res.* 26(11):2797–2802.

International Search Report from co–pending International Application No. PCT/US01/00152, dated Jul. 18, 2001.

*Primary Examiner*—Joseph K. McKane
*Assistant Examiner*—Kamal Saeed
(74) *Attorney, Agent, or Firm*—Ann Peasu; Vincent P. Liptak

(57) ABSTRACT

The present invention provides a novel class of fluorescent cyanine dye compounds that are modified at one of the hetercyclic ring nitrogen atoms with a mobility-modifying moiety that permits the electrophoretic mobilities of polynucleotides labeled with the mobility-modifying cyanine dyes to be adjusted or tuned in a predictable fashion while retaining enzymatic activity. The ability to predictably tune the relative electrophoretic mobilities of the dyes permits the creation of sets of mobility-matched fluorescent dyes of a variety of structures for a variety of applications, including fluorescence-based 4-color nucleic acid sequencing reactions.

5 Claims, No Drawings

US 6,716,994 B1

MOBILITY-MODIFYING CYANINE DYES

1. FIELD OF THE INVENTION

The present invention relates generally to fluorescent dye compounds that are useful as molecular probes. In particular, the present invention relates to fluorescent cyanine dye compounds that are mobility modified for use in nucleic acid sequencing reactions.

2. BACKGROUND OF THE INVENTION

The advent of automated four-color Sanger-type DNA sequencing has revolutionized the speed with which stretches of DNA can be reliably sequenced. In four-color Sanger-type DNA sequencing, a single-stranded target DNA of interest is hybridized with a complementary primer and the primer enzymatically extended with a DNA polymerase in the presence of a mixture of 2'-deoxyribonucleotides capable of supporting continuous primer extension (e.g., dATP, dGTP, dCTP and dTTP or dUTP) and a mixture of four labeled terminators. Each of the terminators is labeled with a different, spectrally distinguishable fluorescent label and terminates primer extension at a single type of template nucleotide. A mixture of terminators is used such that a termination event is achieved at each type of template nucleotide. The product of this primer extension or sequencing reaction is a nested set of labeled primer extension products in which the 3'-terminal nucleotide is identifiable by the color of its fluorescent label. These products are then electrophoretically separated, typically in a single gel lane or capillary, and the sequence of the target DNA determined from the colors of the resultant electrophoresis bands.

To avoid ambiguities in determining the sequence of the target DNA, the dyes used to label the primer extension products should either impart no electrophoretic mobility shifts on the products or impart uniform mobility shifts. However, in most instances, different types of dyes impart vastly different electrophoretic mobility shifts. Since the dyes must be spectrally distinguishable from one another, dyes having different structures, and hence quite different imparted electrophoretic mobility shifts, must be used. While sets of terminators that impart primer extension products with similar mobility shifts are available, rationally designing such sets of "mobility matched" terminators is currently virtually impossible. Rather, the sets are obtained through empirical trial and error. To date, no methods exists whereby one can predictably alter the electrophoretic mobilities imparted by terminators labeled with desirable dyes without altering the spectral properties of the dyes and/or jeopardizing the abilities of the labeled terminators to act as substrates for polymerizing enzymes. Accordingly, these are objects of the present invention.

3. SUMMARY OF THE INVENTION

These and other objects are furnished by the present invention, which in one aspect provides cyanine dye compounds having a mobility-modifying moiety that permits the electrophoretic mobilities of polynucleotides labeled with the dyes to be adjusted or tuned in a predictable fashion.

Cyanine dyes are a well-recognized class of fluorescent molecules which generally comprise first and second parent heteroaromatic ring systems covalently linked together via a methine, polymethine or cyclic alkylene bridge. The dyes may be homodimers, in which the first and second parent heteroaromatic ring systems are both members of the same class, or they may be heterodimers, in which the first and second parent heteroaromatic ring systems are both members of different classes. The parent ring systems may be optionally substituted with one or more substituents which can serve to alter the spectral, chemical and/or physical properties of the dyes.

The present invention concerns the class of cyanine dyes in which both parent heteroaromatic rings belong to the class of rings generally referred to as benzazoles/benzazoliums. The mobility-modifying cyanine dyes of the invention generally comprise: (i) a first parent benzazole/benzazolium heteroaromatic ring system that is substituted at the heteroaromatic ring nitrogen with a linking moiety; (ii) a second parent benzazole/benzazolium heteroaromatic ring system that is substituted at the heteroaromatic ring nitrogen with a mobility-modifying moiety; and (iii) a bridge linking the first and second parent benzazole/benzazolium rings via their respective C-2 carbons. The first and second parent benzazole/benzazolium ring systems may be the same or different, and may be optionally substituted with one or more of the same or different substituent groups. Preferably, both parent benzazole/benzazolium ring systems are the same or different substituted or unsubstituted indoline/indolinium ring systems. Depending upon the particular application, the linking moiety can be used to conjugate, preferably by way of covalent attachment, the mobility-modifying dyes of the invention to other molecules or substances.

Quite significantly, since the mobility-modified and linking moieties are located at opposing ends of the cyanine dye (i.e., on different heteroaromatic rings), nucleosides/tides and/or nucleoside/tide analogs labeled with the mobility-modifying cyanine dyes of the invention, e.g., labeled 2'-deoxyribonucleoside-5'-triphosphates and labeled terminating ribonucleoside-5'-triphosphates (e.g., 2',3'-dideoxyribonucleoside-5'-triphosphates), retain high activity as substrates for DNA polymerizing enzymes, making the mobility-modifying dyes ideal for use in fluorescence-based nucleic acid sequencing applications. Moreover, since the electrophoretic mobilities of polynucleotides labeled with the mobility-modifying dyes can be predictably tuned to match those labeled with other dyes, the mobility-modifying dyes of the invention are ideal for use in 4-color fluorescence-based nucleic acid sequencing reactions, as sets of dyes having matched mobilities in addition to desirable spectral and biological properties can be readily obtained.

Virtually any known cyanine dye can be mobility-modified according to the principles of the invention. Thus, parent heteroaromatic ring systems of which the dyes of the invention can be comprised include, but are not limited to, the substituted and unsubstituted benzazole/benzazolium rings comprising the cyanine, merocyanine and styryl dyes described in U.S. Pat. Nos. 5,486,616, 5,569,587, 5,569,766 and 5,627,027; the substituted and unsubstituted benzazole/benzazolium rings comprising the asymmetric cyanine dyes described in U.S. Pat. Nos. 5,321,130, 5,410,030, 5,436,134, 5,534,416, 5,582,977, 5,658,751, 5,656,449, and 5,863,753; and the substituted and unsubstituted benzazole/benzazolium rings comprising the various sulfonated cyanine dyes described in Tu et al., 1998, *Nucl. Acids Res.* 26(11):2797–2802, the disclosures of which are incorporated herein by reference. Additional substituted and unsubstituted benzazole/benzazolium ring systems of which the mobility-modifying cyanine dyes may be comprised are described in Brooker et al., 1945, "Absorption Spectra of Dyes with Heteroaromatic Nuclei—Color and Constitution.

Part VII. Intepretation of Absorptions of Dyes Containing Heterocyclic Nuclei of Different Basicities," *J. Am. Chem. Soc.* 67:1875–1889 (in particular at page 1878), the disclosure of which is incorporated herein by reference.

The mobility-modifying moiety comprises a pendant group bearing a plurality of charges through substitution with one or more of the same or different charged substituents. The pendant group can be any moiety capable of being substituted with the desired number of charged substituents, but is typically a group having the structure —D–D', where D is ($C_1$–$C_6$) alkyldiyl or 2–6 membered heteroalkyldiyl; and D' is ($C_1$–$C_6$) alkyl, 2–6 membered heteroalkyl, ($C_5$–$C_{14}$) aryl, ($C_5$–$C_{14}$) arylaryl, 5–14 membered heteroaryl or 5–14 membered heteroaryl-heteroaryl. When D is heteroalkyldiyl, it must be attached to the benzazole/benzazolium ring nitrogen atom via an alkyldiyl group. Preferred amongst the various D groups is ($C_1$–$C_6$) alkyleno, particularly ($C_1$–$C_6$) alkanos such as methano (—$CH_2$—), ethano (—$CH_2$—$CH_2$—), propano (—$CH_2$—$CH_2$—$CH_2$—), etc.

The polarity of the charged substituents substituting the pendant group depends upon the direction of the desired electrophoretic mobility shift. When an increase in electrophoretic mobility is desired, anionic substitutents should be used. When a decrease in electrophoretic mobility is desired, cationic substiutents should be used. When multiple charged substitutents are used they can be the same or different, and can even be of mixed polarities, although in most instances all of the charged substituents will have the same polarity.

The number of charged substituents substituting the pendant group depends upon the desired net charge of the mobility-modifying moiety, which in turn depends upon the identity of the charged substituent and the degree of mobility modification necessary. The charged substituents may be any substituent group having a net charge at the desired pH of use (typically pH 6 to 10). Suitable cationic substituents include, by way of example and not limitation, permanent cations such as quaternary ammoniums, especially those of the formula —$N^+RRR$, where each R is independently ($C_1$–$C_6$) alkyl, and cations derived from bases. Permanent cations or cationic substituents that are derived from strong bases ("strong cationic substituents"), such as those having a p$K_a$ of about 8 or greater, are preferred, as these strong cationic substituents are completely ionized at the pHs commonly employed in biological assays such as nucleic acid sequencing reactions.

Suitable anionic substituents include groups having a p$K_a$ of 6 or less, and include by way of example and not limitation, —C(O)O$^-$, —P(O)(O$^-$)$_2$, —P(O)(OH)(O$^-$), —O—P(O)$_2$(O$^-$), —S(O)$_2$O$^-$ and —O—S(O)$_2$O$^-$ (including any associated counterions). Anionic substituents that are derived from strong acids ("strong anionic substituents"), such as those having a p$K_a$ of 3 or less, are preferred, as these strong anionic substituents are completely ionized at the pHs commonly employed in biological assays such as nucleic acid sequencing reactions. Preferred amongst the strong anionic substituents are —S(O)$_2$O$^-$ and —O—S(O)$_2$O$^-$.

In addition to the desired charged substituents, the pendant group may be further substituted with one or more additional uncharged substituents. Such uncharged substituents can serve a variety of purposes, e.g., to increase the water solubility of the mobility-modifying dye, to decrease non-specific binding of the mobility-modifying dyes and/or to decrease the interactions between chromophores of multiply labeled compounds, thereby decreasing quenching of fluorescence.

The bridge joining the two parent heteroaromatic ring systems can be any type of bridge commonly used to join the parent heteroaromatic ring systems of cyanine dyes. Preferably, the bridge permits electron delocalization. Electron-delocalizing bridges useful for linking the heteroaromatic rings of the dyes include, but are not limited to, methine, polymethine, squarine and cyclic alkene bridges. The bridges may be optionally substituted with one or more of the same or different substituents that typically serve to increase the chemical and/or photostability of the dye and/or increase its quantum yield.

The linking moiety has the structure —L—LG, where L is a linker and LG is a linking group that can be used to conjugate, preferably by way of covalent attachment, the mobility-modifying cyanine dye to another compound or substance, such as a protein, nucleoside|tide, polynucleotide, polymer, particle etc. The identity of linking group LG will depend upon the nature of the desired conjugation. For example, the conjugation may be: (i) mediated by ionic interactions, in which case linking group LG is a charged group; (ii) mediated by hydrophobic interactions, in which case linking group LG is a hydrophobic moiety; (iii) mediated by covalent attachment, in which case linking group LG is a reactive functional group ($R_x$) that is either capable of forming a covalent linkage with another complementary functional group ($F_x$) or is capable of being activated so as to form a covalent linkage with complementary functional group $F_x$; or (iv) mediated through the use of pairs of specific binding molecules, such as biotin and avidin/streptavidin, in which case linking group LG is one member of the pair, e.g., biotin.

The linking group LG is attached to the benzazole/benzazolium ring nitrogen via linker L. Depending upon the application, linker L can be hydrophobic, hydrophilic, long or short and/or rigid, semirigid or flexible. Regardless of the identity of the linker L, in order to avoid adversely affecting the spectral properties of the cyanine dye chromophore, it must be attached to the benzazole/benzazolium nitrogen atom via an alkyldiyl group.

In another aspect, the invention provides labeled conjugates comprising a mobility-modifying cyanine dye according to the invention and another molecule or substance. The mobility-modifying cyanine dye is conjugated to the other molecule or substance, typically via covalent attachment, through linking group LG as previously described. Once conjugated, the dye provides a convenient fluorescent label for subsequent detection. The dyes of the invention can be used to fluorescently label a wide variety of molecules and substances, including amino acids, proteins, antibodies, enzymes, receptors, nucleosides/tides, nucleic acids, carbohydrates, lipids, steroids, hormones, vitamins, drugs, metabolites, toxins, organic polymers, etc. The dyes can also be used to label particles such as nanoparticles, microspheres or liposomes. The molecule or substance may be labeled with one or more mobility-modifying cyanine dyes of the invention, which may be the same or different.

In one preferred embodiment, the labeled conjugate is a labeled nucleoside/tide or nucleoside/tide analog. The dye may be conjugated to either the sugar or nucleobase moiety of the receptive nucleoside|tide or nucleoside/tide analog, but is usually conjugated to the nucleobase moiety.

The labeled nucleoside/tide or nucleoside|tide analog may be enzymatically incorporable, in which case it may be conveniently used in conjunction with a template nucleic acid, a primer and appropriate polymerizing enzymes to enzymatically generate labeled polynucleotides. A particularly preferred class of enzymatically-incorporable labeled nucleoside/tides and nucleoside/tide analogs are labeled terminators, as such terminators can be conveniently used in Sanger-type sequencing reactions to generate labeled polynucleotide sequencing fragments having defined gel electrophoretic mobilities.

Alternatively, the labeled nucleoside/tide or nucleoside/tide analog may be synthetically incorporable, such as a labeled nucleosidic or non-nucleosidic phosphoramidite synthesis reagent. Such reagents can be conveniently used in conjunction with standard solid phase oligonucleotide synthesis reagents and supports to label synthetic polynucleotides and/or polynucleotide analogs at their 3'-terminus, their 5'-terminus and/or at one or more internal positions with mobility-modifying dyes of the invention.

In another aspect, the invention provides methods of using the dyes of the invention to sequence a target nucleic acid. The method generally comprises forming a series of differently-sized primer extension products that are labeled with a dye of the invention, separating the series of differently-sized labeled extension products, typically based on size, and detecting the separated labeled extension products based on the fluorescence of the label. The sequence of the target nucleic acid is then assembled according to known techniques.

The series of differently-sized labeled extension products can be conveniently generated by enzymatically extending a primer-target hybrid according to well-known methods. For example, the series of labeled extension products can be obtained using a primer labeled with a dye or dye pair of the invention and enzymatically extending the labeled primer-target hybrid in the presence of a polymerase, a mixture of enzymatically-extendable nucleotides or nucleotide analogs capable of supporting continuous primer extension and at least one, typically unlabeled, terminator that terminates primer extension upon incorporation (e.g., a 2',3'-dideoxyribonucleoside-5'-triphosphate). Alternatively, the series of labeled extension products can be obtained using an unlabeled primer and enzymatically extending the unlabeled primer-target hybrid in the presence of a polymerase, a mixture of enzymatically-extendable nucleotides or nucleotide analogs capable of supporting continuous primer extension and at least one terminator labeled with a dye of the invention. In either embodiment, the polymerase serves to extend the primer with enzymatically-extendable nucleotides or nucleotide analogs until a terminator is incorporated, which terminates the extension reaction. Once terminated, the series of labeled extension products are separated, typically based on size, and the separated labeled extension products detected based on the fluorescence of the labels. The sequence of the target is then obtained via conventional means.

In a particularly advantageous embodiment of this method, a mixture of four different terminators are used in a single extension reaction. Each different terminator is capable of terminating primer extension at a different template nucleotide, e.g., a mixture of 7-deaza-ddATP, ddCTP, 7-deaza-ddGTP and ddTTP or ddUTP, and is labeled with a different, spectrally-resolvable fluorophore, where at least one of the fluorophores is a mobility-modifying dye according to the invention. According to this embodiment, an unlabeled primer-target nucleic acid hybrid is enzymatically extended in the presence of, a polymerase, a mixture of enzymatically-extendable nucleotides or nucleotide analogs capable of supporting continuous primer extension and a mixture of the four different, labeled terminators. Following separation based on size, a series of separated labeled extension products is obtained in which the emission properties (i.e., color) of each separated extension product reveals the identity of its 3'-terminal nucleotide. In a particularly preferred embodiment, all of the labeled terminators are excitable using a single light source.

Alternatively, terminators may be used in the absence of enzymatically-extendable nucleotides. In this instance, the primer is extended by only a single base. Again, the primer may be labeled or, alternatively, one or more of the terminators may be labeled. Preferably, a mixture of four different labeled terminators is used, as described above. These "mini sequencing" embodiments are particularly useful for identifying polymorphisms in chromosomal DNA or cDNA.

In yet another aspect, the invention provides mobility-matched sets of labeled terminators and/or polynucleotide primers that can be conveniently used in Sanger-type sequencing reactions to generate sequencing ladders having matched electrophoretic mobilities. For 4-color nucleic acid sequencing applications, one or several conventional cyanine dyes having the desired spectral properties can be selected and the respective comparative mobilities of polynucleotide fragments labeled therewith obtained. The cyanine dyes can then be simply mobility-modified according to the principles taught herein to tune the electrophoretic mobilities of polynucleotides labeled therewith as necessary to obtain sets of dyes that are mobility-matched. A preferred set of mobility-matched terminators includes Compounds 31, 32, 33 and 34 (see Section 5.10, infra). A preferred set of mobility-matched polynucleotide primers includes primers labeled with the dye chromophores of Compounds 31, 32, 33 and 34.

In a final aspect, the invention provides kits comprising the mobility-modifying cyanine dyes and/or labeled conjugates of the invention and reagents useful for labeling molecules and/or for performing assays such as nucleic acid sequencing.

The mobility-modifying cyanine dyes of the invention provide significant advantages over currently available cyanine dyes. Because the mobility-modifying moiety does not significantly alter the spectral properties of the cyanine dye chromophore, these dyes are useful in virtually any applications that utilize fluorescent dyes. However, owing to their ability to predictably alter the electrophoretic mobilities of polynucleotides labeled therewith, the mobility-modifying dyes of the invention provide the ability to create mobility-matched sets of fluorescent dyes for applications involving the electrophoretic separation of labeled polynucleotides, such as automated nucleic acid sequencing. In particular, mixed dye sets (i.e., dyes with different structures) may be conveniently employed in automated sequencing applications due to the ability to match the respective mobilities of polynucleotides labeled therewith according to this invention. Moreover, enzymatically-incorporable nucleoside/tides, enzymatically-incorporable nucleoside/tide analogs and terminators labeled with the mobility-modifying dyes of the invention retain high enzymatic activity with the polymerases commonly employed in automated nucleic acid sequencing methods, including thermostable polymerases such as AMPLITAQ® DNA polymerase FS (PE Biosystems, Foster City, Calif.).

4.1 DETAILED DESCRIPTION OF THE INVENTION 4.1 Abbreviations

The abbreviations used throughout the specification to refer to certain nucleobases, nucleosides and/or nucleotides are those commonly employed in the art and are as indicated below:

| Expression | Abbreviation |
|---|---|
| adenine | A |
| 7-deazaadenine | 7-deaza-A |
| $N^6$-$\Delta^2$-isopentenyladenine | 6iA |
| $N^6$-$\Delta^2$-isopentenyl-2-methylthioadenine | 2ms6iA |
| cytosine | C |
| guanine | G |
| 6-thioguanine | 6sG |
| 7-deazaguanine | 7-deaza-G |
| $N^2$-dimethylguanine | 2dmG |
| 7-methylguanine | 7mG |
| thymine | T |
| 4-thiothymine | 4sT |
| uracil | U |
| dihydrouracil | D |
| 4-thiouracil | 4sU |
| base Y | Y |
| ribonucleoside-5'-triphosphate | NTP |
| adenosine-5'-triphosphate | ATP |
| 7-deazaadenosine-5'-triphosphate | 7-deaza-ATP |
| cytidine-5'-triphosphate | CTP |
| guanosine-5'-triphosphate | GTP |
| 7-deazaguanosine-5'-triphosphate | 7-deaza-GTP |
| thymidine-5'-triphosphate | TTP |
| uridine-5'-triphosphate | UTP |
| 2'-deoxyribonucleoside-5'-triphosphate | dNTP |
| 2'-deoxyadenosine-5'-triphosphate | dATP |
| 2'-deoxy-7-deazaadenosine-5'triphosphate | 7-deaza-dATP |
| 2'-deoxycytidine-5'-triphosphate | dCTP |
| 2'-deoxyguanosine-5'-triphosphate | dGTP |
| 2'-deoxy-7-deazaguanosine-5'-triphosphate | 7-deaza-dGTP |
| 2'-deoxythymidine-5'-triphospate | dTTP |
| 2'-deoxyuridine-5'-triphosphate | dUTP |
| 2',3'-dideoxyribonucleoside-5'-triphosphate | ddNTP |
| 2',3'-dideoxyadenosine-5'-triphosphate | ddATP |
| 2',3'-dideoxy-7-deazaadenosine-5'-triphosphate | 7-deaza-ddATP |
| 2',3'-dideoxycytidine-5'-triphosphate | ddCTP |
| 2',3'-dideoxyguanosine-5'-triphosphate | ddGTP |
| 2',3'-dideoxy-7-deazaguanosine-5'-triphosphate | 7-deaza-ddGTP |
| 2',3'-dideoxythymidine-5'-triphosphate | ddTTP |
| 2',3'-dideoxyuridine-5'-triphosphate | ddUTP |

4.2 Definitions

As used herein, the following terms are intended to have the following meanings:

"Spectrally Resolvable:" means, in reference to a set of fluorescent dyes, that the fluorescence emission bands of the respective dyes are sufficiently distinct, i.e., sufficiently non-overlapping, that the dyes, either alone or when conjugated to other molecules or substances, are distinguishable from one another on the basis of their fluorescence signals using standard photodetection systems such as photodetectors employing a series of band pass filters and photomultiplier tubes, charged-coupled devices (CCD), spectrographs, etc., as exemplified by the systems described in U.S. Pat. Nos. 4,230,558 and 4,811,218 or in Wheeless et al., 1985, *Flow Cytometry: Instrumentation and Data Analysis*, pp. 21–76, Academic Press, New York. Preferably, all of the dyes comprising a spectrally resolvable set of dyes are excitable by a single light source.

"Mobility-Matched:" refers to a set of fluorescent dyes that, when used to label polynucleotides of equal lengths with one dye molecule per each polynucleotide molecule, yields differentially labeled polynucleotides having substantially similar electrophoretic mobilities. Typically, the relative electrophoretic mobilities of the labeled polynucleotides will vary by less than about one-half nucleotide. Preferably, the mobility-matched dyes are spectrally resolvable, as previously defined.

"Mobility-modifying Dye Chromophore:" refers to a mobility-modifying cyanine dye according to the invention exclusive of its linking moiety —L—LG. For example, the mobility-modifying dye chromophore derived from the mobility-modifying dye according to structural formula (I.A) has the structure:

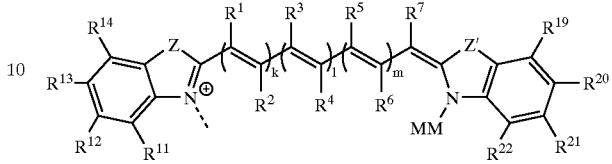

wherein k, l, m, Z, Z', $R^1$, $R^2$, $R^3$, $R^4$, $R^5$, $R^6$, $R^7$, $R^{11}$, $R^{12}$, $R^{13}$, $R^{14}$, $R^{19}$, $R^{20}$, $R^{21}$, $R^{22}$ and MM are as defined for structural formula (I.A), infra, and the dotted line protruding from the heteroaromatic ring nitrogen represents the site of attachment of the linking moiety —L—LG. Mobility-modifying dye chomophores can be derived from other structural formulae described herein in a similar manner.

"Nucleobase:" refers to a substituted or unsubstituted nitrogen-containing parent heteroaromatic ring of a type that is commonly found in nucleic acids. Typically, but not necessarily, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanie (G), isoguanine, $N^2$-dimethylguanine (dmG), 7-methylguanine (7mG), 2-thiopyrimidine, 6-thioguanine (6sG) hypoxanthine and $O^6$-methylguanine; 7deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. Additional exemplary nucleobases can be found in Fasman, 1989, *Practical Handbook of Biochemistry and Molecular Biology*, pp. 385–394, CRC Press, Boca Raton, Fla., and the references cited therein. Preferred nucleobases are purines, 7-deazapurines and pyrimidines. Particularly preferred nucleobases are the normal nucleobases, defined infra, and their common analogs, e.g., 2ms6iA, 6iA, 7-deaza-A, D, 2dmG,:7-deaza-G, 7mG, hypoxanthine, 4sT, 4sU and Y.

"Normal Nucleobase:" refers to a nucleobase that is naturally-occurring and encoding, i.e., adenine, cytosine, guanine, thymine or uracil.

"Nucleoside:" refers to a compound consisting of a nucleobase covalently linked, typically via a heteroaromatic ring nitrogen, to the C1' carbon of a pentose sugar. Typical pentose sugars include, but are not limited to, those pentoses in which one or more of the carbon atoms are each independently substituted with one or more of the same or different —R, —OR, —NRR or halogen groups, where each R is independently hydrogen, ($C_1$–$C_6$) alkyl or ($C_5$–$C_{14}$) aryl. The pentose sugar may be saturated or unsaturated. Exemplary pentose sugars include, but are not limited to, ribose, 2'-deoxyribose, 2'-($C_1$–$C_6$)alkoxyribose, 2'-($C_5$–$C_{14}$) aryloxyribose, 2',3'-dideoxyribose, 2',3'-didehydroribose, 2'-deoxy-3'-haloribose, 2'-deoxy-3'-fluororibose, 2'deoxy-3'-chlororibose, 2'-deoxy-3'-aminoribose, 2'-deoxy-3'-($C_1$–$C_6$)

alkylribose, 2'-deoxy-3'-($C_1$–$C_6$)alkoxyribose, 2'-deoxy-3'-($C_5$–$C_{14}$)aryloxyribose, 2',3'-dideoxy-3'-haloribose and 2',3'-dideoxy-3'-fluororibose.

When the nucleobase is a purine or a 7-deazapurine, the pentose sugar is attached to the N9 or C8 position of the nucleobase. When the nucleobase is a pyrimidine, the pentose sugar is attached to the N1-position of the nucleobase (see, e.g., Kornberg and Baker, 1992, *DNA Replication, 2$^{nd}$ Ed.*, Freeman, San Francisco), except for pseudouridines, in which the pentose sugar is attached to the C5 position of the uracil nucleobase. Preferred nucleosides are those in which the nucleobase is a purine, a 7-deazapurine, a pyrimidine, a normal nucleobase or a common analog of a normal nucleobase and the pentose sugar is any of the exemplary pentose sugars listed above.

"Normal Nucleoside:" refers to a compound consisting of a normal nucleobase covalently linked via the N1 (C, T or U) or N9 (A or G) position of the nucleobase to the C1' carbon of ribose or 2'-deoxyribose.

"Nucleoside Analog:" refers to a nucleoside in which the pentose sugar is replaced with a pentose sugar analog. Exemplary pentose sugar analogs include, but are not limited to, substituted or unsubstituted furanoses having more or fewer than 5 ring atoms, e.g., erythroses and hexoses and substituted or unsubstituted 3–6 carbon acyclic sugars. One or more of the carbon atoms may be independently substituted with one or more of the same or different —R, —OR, —NRR or halogen groups, where each R is independently hydrogen, ($C_1$–$C_6$) alkyl or ($C_5$–$C_{14}$) aryl.

"Nucleotide:" refers to a nucleoside in which one or more, typically one, of the pentose carbons is substituted with a phosphate ester having the formula:

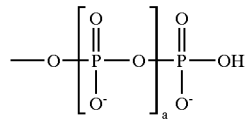

where a is an integer from 0 to 4. Preferably, a is 2 and the phosphate ester is attached to the 3'- or 5'-carbon of the pentose. Particularly preferred nucleotides are those in which the nucleobase is a purine, a 7-deazapurine, a pyrimidine, a normal nucleobase or a common analog thereof.

"Normal Nucleotide:" refers to a normal nucleoside in which the 3'- or 5'-carbon of the ribose or 2'-deoxyribose is substituted with a phosphate ester having the formula:

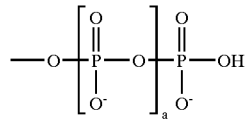

where a is an integer from 0 to 2. Preferred normal nucleotides are those in which a is 2 and the phosphate ester is attached to the 5'-carbon of the ribose (NTP) or 2'-deoxyribose (dNTP).

"Nucleotide Analog:" refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkyiphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present.

Also included within the defintion of "nucleotide analog" are nucleobase monomers which can be polymerized into polynucleotide analogs in which the DNA/RNA phosphate ester and/or sugar phosphate ester backbone is replaced with a different type of linkage.

"Enzymatically-Incorporable Nucleotide or Nucleotide Analog:" refers to a nucleotide or nucleotide analog which is capable of acting as a substrate for a - polymerizing enzyme in a template-directed nucleic acid synthesis reaction such that it is enzymatically incorporated into a nascent polynucleotide or polynucleotide analog chain. Typical enzymatically-incorporable nucleotides and nucleotide analogs are those in which the sugar is a pentose. Preferred enzymatically-incorporable nucleotides are those in which the nucleobase is a purine, a 7-deazapurine, a pyrimidine, a normal nucleobase or a common analog thereof and the pentose is a pentose-5'-triphosphate, such as NTPs, dNTPs and ddNTPs.

"Enzymatically-Extendable Nucleotide or Nucleotide Analog:" refers to an enzymatically-incorporable nucleotide or nucleotide analog that, once incorporated into a nascent polynucleotide or polynucleotide analog chain, supports incorporation of further nucleotides or nucleotide analogs. Thus, enzymatically-extendable nucleotides or nucleotide analogs have a hydroxyl group that is capable of forming a covalent linkage with another, subsequent nucleotide or nucleotide analog. Typical enzymatically-extendable nucleotides and nucleotide analogs are those in which the sugar is a pentose. Preferred enzymatically-extendable nucleotides are those in which the nucleobase is a purine, a 7deazapurine, a pyrimidine, a normal nucleobase or a common analog thereof and the pentose sugar is a 3'-hydroxylpentose-5'-triphosphate, such as NTPs and dNTPs.

"Terminator:" refers to an enzymatically-incorporable nucleotide or nucleotide analog which does not support incorporation of subsequent nucleotides or nucleotide analogs. Typical terminators are those in which the nucleobase is a purine, a 7-deaza-purine, a pyrimidine, a normal nucleobase or a common analog thereof and the sugar moiety is a pentose which includes a 3'-substituent that blocks further synthesis. Substituents that block further synthesis include, but are not limited to, amino, deoxy, halogen, alkoxy and aryloxy groups. Exemplary terminators include, but are not limited to, those in which the sugar-phosphate ester moiety is 2',3'-dideoxyribose-5'-triphosphate, 2',3'-dideoxy-3"-aminoribose-5'-triphosphate, 2'-3'-deoxy-3"-haloribose-5'-triphosphate, 2',3'-dideoxy-3"-fluororibose-5'-triphosphate, 2'-deoxy-3'-($C_1$–$C_6$)alkoxyribose-5'-triphosphate, 2'-deoxy-3'-($C_5$–$C_{14}$)aryloxyribose-5'-triphosphate, 2',3'-dideoxy-3"-($C_1$–$C_6$) alkylribose-5'-triphosphate and 2',3'-didehydroribose-5'-triphosphate.

"Nucleoside/tide:" refers to a nucleoside and/or a nucleotide and/or a mixture thereof.

"Polynucleotide:" refers to a linear polymeric chain of nucleoside monomer units that are covalently connected to one another by phosphate ester internucleoside linkages. Unless stated otherwise, "polynucleotide" as used herein includes polymers of any length, including oligonucleotides, polynucleotides and nucleic acids as those terms are commonly used in the art. Where polynucleotides of specific size ranges are intended, the number of monomer units is specifically delineated. Thus, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g. "ATGCCTG," it will be understood that the sequence is presented in the 5'→3' direction. 2'-Deoxyribopolynucleotides are preceded with the letter "d," e.g. "d(ATGCCTG)."

Polynucleotides may be composed of a single type of sugar moiety, as in the case of RNA and DNA, or mixtures of different sugar moieties, as in the case of RNA/DNA chimeras. Preferred polynucleotides are ribopolynucleotides and 2'-deoxyribopolynucleotides according to the structural formulae below:

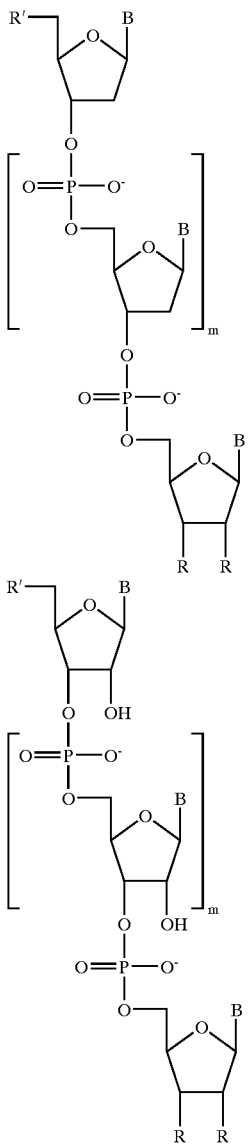

wherein:
each B is independently a nucleobase, preferably a purine, a 7-deazapurine, a pyrimidine, a normal nucleobase or a common analog thereof;

each m defines the length of the respective polynucleotide and can range from zero to thousands, tens of thousands, or even more;

each R is independently selected from the group consisting of hydrogen, halogen, fluoro, ($C_1$–$C_8$) alkyl, —OR" and —NR"R", where each R" is independently hydrogen, ($C_1$–$C_6$) alkyl or ($C_5$–$C_{14}$) aryl, or two adjacent Rs are taken together to form a bond such that the ribose sugar is 2',3'-didehydroribose; and each R' is independently hydroxyl or

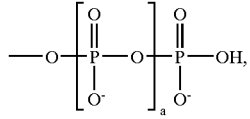

where a is zero, one or two.

In the preferred ribopolynucleotides and 2'-deoxyribopolynucleotides illustrated above, the nucleobases B are covalently attached to the C1' carbon of the sugar moiety as previously described.

"Polynucteotide Analog:" refers to a polynucleotide in which at least one nucleoside monomer unit is a nucleoside analog and/or at least one phosphate ester intenucleoside linkage is a phosphate ester analog, as previously defined. Also included within the definition of polynucleotide analogs are polynucleotides in which the phosphate ester and/or sugar phosphate ester internucleoside linkages are replaced with other types of linkages, such as N-(2-aminoethyl)-glycine amides and other amides (see, e.g., Nielsen et al., 1991, Science 254:1497–1500; WO 92/20702; U.S. Pat. No. 5,719,262; U.S. Pat. No. 5,698,685) morpholinos (see U.S. Pat. No. 5,698,685; U.S. Pat. No. 5,378,841; U.S. Pat. No. 5,185,144); carbamates (see Stirchak & Summerton, 1987, J. Org. Chem. 52:4202); methylene(methylimino) (see Vasseur et al., 1992, J. Am. Chem. Soc. 1 14:4006); 3'-thioformacetals (see Jones et al., 1993, J. Org. Chem. 58:2983); sulfamates (see U.S. Pat. No. 5,470,967); and others (see, e.g., U.S. Pat. No. 5,817,78 1; Frier & Altman, 1997, Nucl. Acids Res. 25:4429 and the references cited therein).

"Alkyl:" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop2-en-1-yl, cycloprop-1-en-1-yl; cycloprop-2-en-1-yl, prop-1-yn-1-yl , prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are ($C_1$–$C_6$) alkyl.

"Alkanyl:" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are ($C_1$–$C_6$) alkanyl.

"Alkenyl:" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop- 1-en-1 -yl, but-2-en-1-yl , but-2-en- 1 -yl, but-2-en-2-yl, buta-1 ,3-dien-1 -yl, buta-1 ,3dien-2-yi, cyclobut-1-en-1-yl, cyclobut-1-en-3-yl, cyclobuta-1,3-dien-1-yl, etc.; and the like. In preferred embodiments, the alkenyl group is $(C_2-C_6)$ alkenyl.

"Alkynyl:" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl , prop-2-yn-1-yl, etc.; butynyls such as but-1-yn-1-yl, but-1-yn-3-yl, but-3-yn-1-yl, etc.; and the like. In preferred embodiments, the alkynyl group is $(C_2-C_6)$ alkynyl.

"Alkyldiyl:" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop2-en-1,2-diyl, cycloprop-2-en-1,1-diyl, prop-1-yn-1,3-diyl, etc.; butyldiyls such as, butan-1,1-diyl, butan-1,2-diyl, butan-1,3diyl, butan-1,4-diyl, butan-2,2-diyl, 2-methyl-propan-1,1 -diyl, 2-methyl-propan-1,2-diyl, cyclobutan-1,1 -diyl; cyclobutan-1,2-diyl, cyclobutan-1,3-diyl, but-1-en-1,1-diyl, but-1-en-1,2-diyl, but-1-en-1,3-diyl, but-1-en-1,4diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4diyl, buta-1,3-diyn-1,4-diyl, etc.; and the like. Where specific levels of saturation are intended, the nomenclature alkanyldiyl, alkenyldiyl and/or alkynyidiyl is used. In preferred embodiments, the alkyldiyl group is $(C_1-C_6)$ alkyldiyl. Also preferred are saturated acyclic alkanyldiyl groups in which the radical centers are at the terminal carbons, e.g., methandiyl (methano); ethan-1,2-diyl (ethano); propan-1,3diyl (propano); butan-1,4diyl (butano); and the like (also referred to as alkylenos, defined infra).

"Alkyleno:" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is $(C_1-C_6)$ or $(C_1-C_4)$ alkyleno. Also preferred are straight-chain saturated alkano groups, e.g., methano, ethano, propano, butano, and the like.

"Heteroalkyl, Heteroalkanyl, Heteroalkenyl, Heteroalkanyl, Heteroalkyldiyi and Heteroalkyleno:" refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —SH$_2$—, —S(O)$_2$—, —SnH$_2$— and the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

"Acyclic Heteroatomic Bridge:" refers to a divalent bridge in which the backbone atoms are exclusively heteroatoms. Typical acyclic heteroatomic bridges include, but are not limited to, any of the various heteroatomic groups listed above, either alone or in combinations.

"CYClic Heteroalkyl:" refers to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cyclic heteroalkanyl" or "cyclic heteroalkenyl" is used. Typical cyclic heteroalkyl moieties include, but are not limited to, groups derived from epoxides, imidazolidine, morpholine, piperazine, piperidine, pyrazolidine, pyrrolidine, quinuclidine, and the like. In preferred embodiments, the cyclic heteroalkyl is a 3–6 membered cyclic heteroalkyl. Particularly preferred cyclic heteralkyls are morpholino, pyrrolidino, pipyridino, tetrahydrothiopheno, tetrahydrofliranyl and tetrahydropyranyl.

"Parent Aromatic Ring System:" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl:" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C5–C$_{r4}$) aryl, with (C$_5$–C$_{10}$) being even more preferred. Particularly preferred aryls are cyclopentadienyl, phenyl and naphthyl.

"Aryldiyl:" refers to a divalent aromatic hydrocarbon group derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the azyldiyl group is (C5–C$_{r4}$) aryldiyl, with (C$_5$–C$_{10}$) being even more preferred. The most preferred aryldiyl groups are divalent groups derived from benzene and naphthalene, especially phena-1,4-diyl, naphtha-2,6-diyl and naphtha-2,7-diyl.

"Aryleno:" refers to a divalent bridge group having two adjacent monovalent radical centers derived by the removal of one hydrogen atom from each of two adjacent carbon atoms of a parent aromatic ring system. Attaching an aryleno bridge group, e.g. benzo, to a parent aromatic ring system, e.g benzene, results in a fised aromatic ring system, e.g. naphthalene. The bridge is assumed to have the maximum number of non-cumulative double bonds consistent with its attachment to the resultant fused ring system. When an aryleno group is formed by taking together two adjacent substituents on a structure that includes alternative substituents, to avoid double-counting carbon atoms, the carbon atoms of the aryleno bridge replace the bridging carbon atoms of the structure. As an example, consider the following structure:

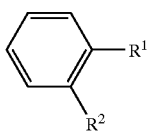

wherein:
R$^1$, when taken alone is hydrogen, or when taken together with R$^2$ is (C$_5$–C$_{14}$) arleno; and
R$^2$, when taken alone is hydrogen, or when taken together with R$^1$ is (C$_5$–C$_{14}$) aryleno.

When R$^1$ and R$^2$ are each hydrogen, the resultant compound is benzene. When R$^1$ taken together with R$^2$ is C$_6$ aryleno (benzo), the resultant compound is naphthalene. When R$^1$ taken together with R$^2$ is C$_{10}$ aryleno (naphthaleno), the resultant compound is anthracene or phenanthrene. Typical aryleno groups include, but are not limited to, aceanthryleno, acenaphthyleno, acephenanthrleno, anthraceno, auuleno, benzeno (benzo), chryseno, coroneno, fluorantheno, fluoreno, hexaceno, hexapheno, hexaleno, as-indaceno, s-indaceno, indeno, naphthaleno (naphtho), octaceno, octapheno, octaleno, ovaleno, penta-2,4dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2] naphthaleno, [2,3]naphthaleno, etc. Thus, in the above example, when R$^1$ taken together with R$^2$ is [2,3] naphthaleno, the resultant compound is anthracene. When R$^1$ taken together with R$^2$ is [1,2]naphthaleno, the resultant compound is phenanthrene. In a preferred embodiment, the aryleno group is (C$_5$–C$_{14}$), with (C$_5$–C$_{10}$) being even more preferred.

"Arylaryl:" refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C$_5$–C$_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a (C$_5$–C$_{14}$) aromatic, more preferably a (C$_5$–C$_{10}$) aromatic. Also preferred are arylaryl groups in which all of the parent aromatic ring systems are identical, e.g., biphenyl, triphenyl, binaphthyl, trinaphthyl, etc.

"Biaryl:" refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C$_5$–C$_{14}$) aromatic rings, more preferably (C$_5$–C$_{10}$) aromatic rings. A particularly preferred biaryl group is biphenyl. "Arylalkyl:" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C$_6$–C$_{20}$) arylalkyl, e.g., the alkanyl, alkenyl or alkynyl moiety of the arylalkyl group is (C$_1$–C$_6$) and the aryl moiety is (C$_5$–C$_{14}$). In particularly preferred embodiments the arylalkyl group is (C$_6$–C$_{13}$), 10 e.g., the alkanyl, alkenyl or alkynyl moiety of the arylalkyl group is (C$_1$–C$_3$) and the aryl moiety is (C$_5$–C$_{10}$).

"Arylheteroalkyl:" refers to an acyclic heteroalkyl group in which one of the hydrogen atoms bonded to a carbon or heteroatom, typically a terminal carbon or heteroatom, is replaced with an aryl group. Where arylheteroalkyl moieties are having specified levels of saturation intended, the nomenclature aryl heteroalkanyl, aryl heteroalkenyl and/or aryl heteroalkynyl is used. In preferred embodiments, the arylheteroalkyl group is a 6–26 membered arylheteroalkyl, e.g., the heteroalkyl moiety is 1–6 membered and the aryl moiety is (C$_5$–C$_{20}$) aryl. In particularly preferred embodiments, the arylheteroalkyl group is 6–13 membered, e.g., the heteroalkyl moiety is 1–3 membered and the aryl moiety is (C$_5$–C$_{10}$).

"Parent Heteroaromatic Ring System:" refers to a parent aromatic ring system in which one or more carbon atoms (and any associated hydrogen atoms) are each independently replaced with the same or different heteroatom. Typical heteratoms to replace the carbon atoms include, but are not limited to, N, P, O, S, Si, etc. (Including and associated hydrogen or other atoms). Specifically included within the definition of "parent heteroaromatic ring systems" are fused ring systems in which one or more of the rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline,. isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–14 membered heteroaryl, with 5–10 membered heteroaryl being particularly preferred. The most preferred heteroaryl groups are those derived from thiophene, pyrrole, benzothiophene, benzoftiran, indole, pyridine, quinoline, imidazole, oxazole and pyrazine.

"Heteroardiyl:" refers to a divalent heteroaromatic group derived by the removal of one hydrogen atom from each of two different, atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent groups derived from acridine, arsindole, carbazole, β-carboline, chromane, chromene, cinnoline, furan, imidazole, indazole, indole, indoline, indolizine, isobenzofiran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryldiyl group is 5–14 membered heteroaryldiyl, with 5–10 membered being particularly preferred. The most preferred heteroaryldiyl groups are divalent groups derived from the preferred heteroaryls thiophene, pyrrole, benzothiophene, benzofuran, indole, pyridine, quinoline, imidazole, oxazole and pyrazine.

"Heteroaryleno:" refers to a divalent bridge group having two adjacent monovalent radical centers derived by the removal of one hydrogen atom from each of two adjacent atoms of a parent heteroaromatic ring system. Attaching a heteroaryleno bridge group, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. When a heteroaryleno substituent is formed by taking together two adjacent substituents on a structure that includes alternative substituents, to avoid double- counting ring atoms, the ring atoms of the heteroaryleno bridge replace the bridging ring atoms of the structure. As an example, consider the following structure:

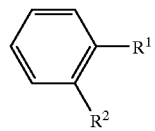

wherein:
$R^1$, when taken alone is hydrogen, or when taken together with $R^2$ is 5–14 membered heteroaryleno; and
$R^2$, when taken alone is hydrogen, or when taken together with $R^1$ is 5–14 membered heteroaryleno;

When $R^1$ and $R^2$ are each hydrogen, the resultant compound is benzene. When $R^1$ taken together with $R^2$ is a i-membered heteroaryleno (e.g., pyridino), the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, flrano, imidazolo, indazoleno, indoleno, indolizino, isobenzofirano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino,. quinolizino, quinoxalino, tetrazoleno, thiadiazoleno, thiazoleno, thiopheno, triazoleno, xantheno, and the like. Where a specific connectivity is intended, the involved bridging n atoms (of the heteroaryleno bridge) are denoted in brackets, e.g., [1,2]pyridino, [2,3]pyridino, [3,4] pyridino, etc. Thus, in the above example, when $R^1$ taken together with $R^2$ is [1,2]pyridino, the resultant compound is quinolizine. When $R^1$ taken together with $R^2$ is [2,3] pyridino, the resultant compound is quinoline. When $R^1$ taken together with $R^2$ is [3,4]pyridino, the resultant compound is isoquinoline. In preferred embodiments, the heteroaryleno group is 5–14 membered heteroaryleno, with 5–10 membered being even more preferred. The most preferred heteroaryleno groups are those derived from the preferred heteroaryls thiophene, pyrrole, benzothiophene, benzofuira, indole, pyridine, quinoline, imidazole, oxazole and pyrazine.

"Heteroaryl-Heteroaryl:" refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroatomic ring systems. For example, 5–14 membered heteroaryl-heteroaryl is a heteroaryl-heteroaryl group in which each parent heteroaromatic ring system comprises from 5 to 14 atoms, e.g., bipyridyl, tripuridyl, etc. Preferably, each parent heteroaromatic ring system is independently a 5–14 membered heteroaromatic, more preferably a 5–10 membered heteroaromatic. Also preferred are heteroaryl-heteroaryl groups in which all of the parent heteroaromatic ring systems are identical. The most preferred heteroaryl-heteroaryl groups are those in which each heteroaryl group is derived from the preferred heteroaryls thiophene, pyrrole, benzothiophene, benzofran, indole, pyridine, quinoline, imidazole, oxazole and pyrazine.

"Biheteroaryl:" refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5–14 membered heteroaromatic rings, more preferably 5–10 membered heteroaromatic rings. The most preferred biheteroaryl groups are those in which the heteroaryl groups are derived from the preferred heteroaryls thiophene, pyrrole, benzothiophene, benzofuran, indole, pyridine, quinoline, imidazole, oxazole and pyrazine.

"Heteroarylalkyl:" refers to an acyclic alkyl group in which one of the hydrogen atoms bonded to a carbon atom, typically a terminal or $sp^3$ carbon atom, is replaced with a heteroaryl group. Where specific alllyl moieties are intended, the nomenclature heteroarylalkanyl, heteroarylakenyl and/or heterorylalklynyl is used. In preferred embodiments, the heteroarylalkyl group is a 6–20 membered heteroarylalkyl, e.g., the alkanyl, alkenyl or alkynyl moiety of the heteroarylalkyl is 1–6 membered and the heteroaryl moiety is a 5–14-membered heteroaryl. In particularly preferred embodiments, the heteroarylalkyl is a 6–13 membered heteroarylalkyl, e.g., the alkanyl, alkenyl or alkynyl moiety is 1–3 membered and the heteroaryl moiety is a 5–10 membered heteroaryl.

"Substituted:" refers to a group in which one or more hydrogen atoms are each independently replaced with the same or different substituent(s). Typical substituents include, but are not limited to, —X, —R, —O⁻, =O, —OR, —SR, —S⁻, =S, —NRR, =NR, perhalo ($C_1$–$C_6$) alkyl,—$CX_3$, —$CF_3$, —CN, —OCN, —SCN, —NO, —$NO_2$, =$N_2$, —$N_3$, —S(O)$_2$O⁻, —S(O)$_2$OH, —S(O)$_2$R, —OS($O_2$)O⁻, —OS(O)$_2$OH, —OS(O)$_2$R, —P(O)(O⁻)$_2$, —P(O)(OH)(O⁻), —OP(O)$_2$(O⁻), —C(O)R, —C(S)R, —C(O)OR, —C(O)O⁻, —C(S)OR, and —C(NR)NRR, where each X is independently a halogen; each R is independently hydrogen, halogen, alkyl, alkanyl, alkenyl, alkynyl, aryl, arylalkyl, arylaryl, arylheteroalkyl, heteroaryl, heteroarytalkyl, heteroaryl-heteroaryl, —NR'R', —C(O)R' or —S(O)$_2$R$^1$; and each R$^1$ is independently hydrogen, alkyl, alkanyl, alkynyl, aryl, arylalkyl, arylheteralkyl, arylaryl, heteroaryl, heteroarylalkyl or heteroaryl-heteroaryl.

43 The Compounds

As discussed in the Background Section, the fluorescent dyes used to label polynucleotides in applications such as nucleic acid sequencing reactions frequently have a significant impact on their electrophoretic mobilities. These differences in electrophoretic mobilities are undesirable, as they can lead to significant ambiguities in fluorescence-based nucleic acid sequencing reactions, especially in 4-color sequencing reactions where fragments terminated with different terminating bases are separated in a single gel lane or capillary. For example, in 4-color Sanger-type nucleic acid sequencing methods, the base sequence is determined by correlating a color with a termination event. The order of the colors directly yields the order of the base sequence in an electrophoresis experiment. A dye label can impose more than a 10–12 base displacement in the electrophoretic mobility of a labeled fragment as compared with the corresponding unlabeled fragment. If all four labels impart the same mobility shift, then the correct order of bands is obtained on the elcetrophoresis gel or trace. However, if one of the dye labels imparts a mobility shift that is different from that imparted by the other three, all fragments labeled with that dye will be frame-shifted with respect to fragments labeled with the other dyes. Since the fragments will electrophorese out of order, an incorrect sequence will be obtained.

As a consequence, efforts have been made to develop families of dyes that induce minimal relative mobility shifts between labeled polynucletide fragments (Ju et al., 1995, Proc. Natl. Acad Sci. USA 92:4347–4351; Ju et al., 1995, Anal. Biochem. 231:131–140; Ju et al., 1996, Nucl. Acids Res. 24:1144–1148; Metzker et al., 1996, Science 271:1420–1422; Hung et al., 1996, Anal. Biochem. 243:15–27; Hung et al., 1997, Anal. Biochem. 252:78–88). In general, this has been accomplished by adjusting the structure of the dye-DNA linker (Metzker et al., 1996, supra).

Recently, it has been discovered that such mobility shifts are much more apparent with capillary array electrophoresis (CAE) than with traditional slab gel electrophoresis (Marsh et al., 1997, J. Capillary Electrophoresis 4:83–89). Thus, dyes exhibiting matched mobilities in a slab gel format may still display significant relative mobility shifts in the more desirable, higher through-put CAE format (Tu et al., 1997, Nucl. Acids Res. 26:2797–2802). As a consequence of this observation, Bashkin and co-workers recently studied the electrophoretic mobilities of polynucleotides labeled with certain cyanine dyes (Tu et al., 1998, supra). Through these studies, it was found that several factors play a role in the observed electrophoretic mobilities of labeled polynucleotides. Most notable are the net charge of the dye and the position(s) of charged substituents on the dye. While certain trends were noted, the authors simply catalogued observed electrophoretic mobilities. The authors did not study the effect of substitutions on the biological activity of nucleotides labeled with the dyes.

The present invention provides a novel class of fluorescent cyanine dye compounds that overcome this and other limitations in the art. The cyanine dye compounds of the invention are substituted at one of the heteroaromatic ring nitrogen atoms with a pendant group carrying a plurality of charges ("mobility-modifing moiety"). By adjusting the number of charges carried by the pendant group, the electrophoretic mobilities of polynucleotides labeled with the mobility-modifying cyanine dyes can be predictably adjusted or tuned to match the electrophoretic mobilities of polynucleotides labeled with other fluorescent dyes. Remarkably, the mobility-imparting characteristics of a particular "parent" cyanine dye can be modified without significantly altering the spectral properties of the dye. Moreover, enzymatically-incorporable nucleotides and nucleotide analogs labeled with the mobility-modifying dyes retain a high level of biological activity as substrates for the polymerase enzymes commonly employed in nucleic acid sequencing reactions, such as the thermostable polymerase AMPLITAQ® DNA polymerase FS (PE Biosystems, Foster City, Calif.). Consequently, the mobility-modifying cyanine dyes of the invention permit sets of mobility-matched dyes and/or mobility-matched labeled nucleosides/tides and analogs having specified spectral and/or biological properties to be readily obtained.

The mobility-modifying cyanine dyes of the invention belong to the well-recognized class of fluorescent molecules commonly known as cyanine dyes. Cyanine dyes generally comprise first and second parent nitrogen-containing heteroaromatic ring systems that are covalently linked together via a bridging moiety (see, e.g., U.S. Pat. No. 5,569,587). The present invention concerns the class of cyanine dyes in which both parent heteroaromatic ring systems belong to the class of rings generally referred to in the cyanine dye art as benzazoles/benzazoliums.

Benzole/Benzazolium heteroaromatic ring systems have the following general structure:

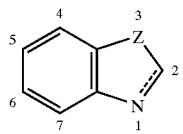

wherein:

Z is selected from the group consisting of —S—, —O—, —Se— and —CRR—, where each R, when taken alone, is independently ($C_1$–$C_6$) alkyl, or when taken together with another R is ($C_4$–$C_5$) alkyleno or ($C_4$–$C_5$) alkano. In the illustrated structure, the dotted line indicates a bond which may be either a single bond or a double bond. Since the mobility-modifying dyes of the invention are substituted at the ring nitrogen, whether the bond is a single bond or a double bond will depend upon the nature of the C2 substituent. When the bond is a single bond, the ring system is a benzazole. When the bond is a double bond, the ring nitrogen is positively charged and the ring system is a benzazolium. As will be described in more detail herein, the various carbons at positions C4, C5, C6 and C7 may be independently substituted with a variety of different substituents.

In the above structure, when Z is S, the heteroaromatic ring system is a substituted or unsubstituted benzothiazole/benzothiazolium; when Z is O, the heteroaromatic ring system is a substituted or unsubstituted benzoxazole/benzoxazolium; when Z is Se, the heteroaromatic ring system is a substituted or unsubstituted benzoselenazolel-benzoselenazolium; and when Z is CRR, the heteroaromatic ring system is a substituted or unsubstituted indoline/indolinium.

While both rings belong to the same general class, they need not be identical. Nor must they both be members of the same subclass. For example, one ring may be a substituted or unsubstituted benzoxazole/benzoxazolium and the other ring may be a substituted or unsubstituted indoline/indolinium. Mobility-modifying dyes of the invention in which both rings are members of the same subclass are referred to as "homodimers." Those dyes in which each ring is a member of a different subclass are referred to as "heterodimers." The substitution patterns of the rings of the homodimeric and/or heterodimeric dyes of the invention may be, but need not be, identical.

In the mobility-modifying cyanine dyes of the invention, the heteroaromatic ring nitrogen of one of the parent benzazolelbenzazolium ring systems is substituted with a mobility-modifying moiety. The heteroaromatic ring nitrogen of the other parent ring system is substituted with a linking moiety for conjugating the mobility-modifying cyanine dye to other molecules or substances. The nature of the mobility-modifying and linking moieties are described in more detail, infra.

The heteroaromatic ring systems may be optionally substituted with one or more of the same or different substituents, which can serve to alter the spectral, chemical and/or physical properties of the dyes, as will be described more fully below. The substitution patterns of each ring may be, but need not be, identical. Thus, in one illustrative embodiment of the invention, the mobility-modifying cyanine dyes are compounds according to structural formula (1):

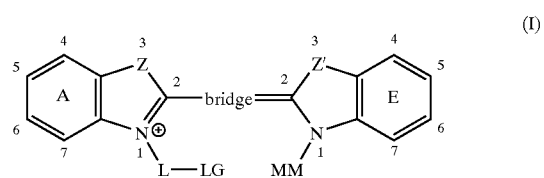

(I)

wherein:

rings A and E are the same or different substituted or unsubstituted benzazole/benuazolium heteroaromatic ring systems;

"L-LG" represents a linking moiety for conjugating the mobility-modifying cyanine dye to another molecule or substance, where L is a linker and LG is a linking group;

"bridge" is a bridging moiety linking the be le n lium heteroaromatic ring systems A and E to one another at their respective C-2 carbon atoms; and "MM" is a mobility-modifying moiety.

As will be discussed in more detail below, in structural formula (I), both the "L" and "MM" substituents comprise a terminal alkyldiyl group that is bonded to the heteroaromatic ring nitrogen such that the bond linking these substituents to their respective nitrogens of rings A and E is a N-CRR bond, where each R is independently hydrogen or ($C_1$–$C_6$) alkyl.

The attachment of the mobility-modifying moiety and linking moiety to different heteroaromatic ring nitrogens constitutes an important feature of the mobility-modifying dyes of the invention that has several important consequences. It is well-known that substituting the aromatic rings of chromophores and fluorophores such as cyanine dyes frequently alters their spectral properties in an unpredictable fashion. Rile not completely understood, it is believed that such spectral changes are due in part to perturbations of the electronic delocalization of the chromophore or fluorophore. Attaching the mobility-modifying and linking moieties to heteroaromatic ring nitrogens minimizes these spectral changes, resulting in mobility-modifying cyanine dyes having spectral properties that are substantially similar to those of the respective unmodified dyes. As a consequence, once a dye having desirable spectral properties is identified, it can be simply modified according to the principles described herein to predictably alter its influence on the electrophoretic mobilities of polynucleotides labeled with the resultant mobility-modifying dye without altering its spectral properties. Moreover, placing the mobility-modifying and linking moieties on different heteroaromatic ring systems permits the dyes to be conjugated to nucleotides and nucleotide analogs without affecting the ability of the resultant labeled nucleotides and nucleotide analogs to act as substrates for polymerizing enzymes.

Based on the above, those of skill in the art will appreciate that virtually any benzazole/benzazolium cyanine dye that is now known in the art or that is later developed can be advantageously mobility-modified according to the principles described herein. Thus, heteroaromatic rings A and E can each be independently selected from amongst the plethora of benzazole/benzazolium ring systems commonly used in cyanine dyes. Such ring systems include, for example, the substituted and unsubstituted benzazole/benzazolium ring systems comprising the cyanine, merocyanine and styryl dyes described in U.S. Pat. Nos. 5,486,616, 5,569,587, 5,569,766, 5,627,027; the substituted and unsubstituted benzazole/benzazolium ring systems comprising the asymmetric cyanine dyes described in U.S. Pat. Nos. 5,321,130, 5,410,030, 5,436,134, 5,534,416, 5,582,977, 5,658,751, 5,656,449 and 5,863,753; the substituted and unsubstituted benzazole/benzazolium ring systems comprising the sulfonated cyanine dyes described in Tu el al., 1998, Nucl. Acids Res. 26(11):2797–2802; and the various substituted and unsubstituted benzazolefbenzazolium ring systems described in Brooker et al., 1945, "Absorption Spectra of Dyes with Heteroaromatic Nuclei—Color and Constitution. Part VII. Interpretation of Absorptions of Dyes Containing Heterocyclic Nuclei of Different Basicities," *J. Am. Chem. Soc.* 67:1875–1889 (particularly at page 1878), the disclosures of which are incorporated herein by reference. In order to obtain mobility-modifying cyanine dyes according to the invention from these various rings, the substituent at one of the heteroaromatic ring nitrogens is replaced with a mobility-modifying moiety and the substituent at the other heteroaromatic ring nitrogen is replaced with a linking moiety as described herein.

In a preferred embodiment of the invention, the mobility-modifying dyes of the invention are homodimers, i.e., benzazole/benzazolium rings A and E are members of the same subclass, although they may have different patterns of substitution. More preferably, benzazole/benzazolium rings A and E are the same or different substituted or unsubstituted indolinelindolinium ring systems. Various mobility-modifying dyes comprised of a variety of different benzazole/benzazolium rings are described in more detail, infra.

Benzazoletenzazolium rings A and E are covalently attached to one another via their C2 carbons by a bridging moiety designated "bridge" in structural formula (I). Those of skill in the art will appreciate that virtually any bridging moiety employed in the art to covalently attach the parent rings of cyanine dyes to one another can be used to attach rings A and E to one another. Suitable bridging moieties are described, for example, in *Polymethine Dyes Structure and Propterties*, Nikolai Tyutyukov et aL, St. Kliment Ohridski University Press, 1991, the disclosure of which is incorporated herein by reference.

Preferably, rings A and E are attached to one another with bridges that permit extensive electronic delocalization. Bridges permitting extensive electron delocalization include, but are not limited to, methine, polymethine, squarine and cyclic alkylene bridges. The various carbon atoms of the bridges may be optionally substituted with one or more of the same or different substitutents, which are typically selected ftom the group consisting of($C_1$–$C_6$) alkyl, halogen, fluorine, chlorine, CN, $CF_3$, ($C_5$–$C_{14}$) aryl and 5–14 membered heteroaryl. In one embodiment, the bridge is a methine or polymethine bridge according to structural formula (B.1):

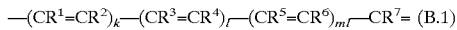

where:
k, l and m are each independently integers from 0 to 1; and $R^1$, $R^2$, $R^3$, $R^4$, $R^5$, $R^6$ and $R^7$ are each independently selected from the group consisting of hydrogen, halogen, —F, —Cl, —CN, —$CF_3$, ($C_1$–$C_6$) alkyl, ($C_5$–$C_{14}$) aryl or 5–14 membered heteroaryl.

For the polymethine bridges of structural formula (B.1), the number of methine groups (—CH=) between the heteroaromatic ring systems influences the spectral properties of the dye (see, e.g., Brooker et al, supra). Generally, the greater the number of methine groups, the longer the wavelengths of the absorption and emission sprectra Thus, the length and composition of the bridge can be adjusted to tune the spectral properties of the dye as desired. For dyes designed to fluoresce when excited using a red (630–650 nm) excitation source, preferred polymethine bridges are those in which the sum of k, l and m is 2. Particularly preferred methine and polymethine bridges are those in which $R^1$, $R^2$, $R^3$, $R^4$, $R^5$, $R^6$ and $R^7$, if present, are each hydrogen. A particularly preferred polymethine bridge is —CH=CH—CH=CH—CH=.

In another embodiment, the bridge comprises a 4–6 membered cyclic alkylene or cyclic heteroalkylene, which may be optionally substituted or unsubstituted, and which may also include optional flanking methine or polymethine units. The optional flanking methine or polymethine units may be substituted or unsubstituted, as previously described for the polymethine bridges of formula (B.1). The cyclic alkylene or heteroaltylene, and any optional flanking methine or polymethine units, forms an allylic system which permits extensive electron delocalization. In a preferred embodiment, the cyclic alkylene bridge is a compound according to structural formula (B.2):

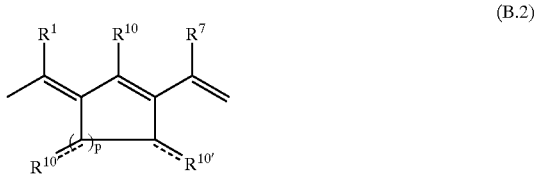

wherein:
p is an integer from 0 to 2;
$R^1$ and $R^7$ are as previously defmed for structural formula (B.I); and
$R^{10}$ and $R^{10'}$ are each independently selected from the group consisting of hydrogen, oxygen, halogen, —F, —Cl, —CN, —$CF_3$, —OR, —SR, —NRR, ($C_1$–$C_6$) alkyl, ($C_5$–$C_{14}$) aryl or 5–14 membered heteroaryl, where each R is independently hydrogen or ($C_1$–$C_6$) alkyl.

In structural formula (B.2), the dotted lines at substituents $R^{10'}$ represent bonds that may be either single bonds or double bonds, depending upon the substituent. For example, when $R^{10'}$ is oxygen, it may be double-bonded to the carbon, forming a carbonyl substituent.

In a preferred embodiment, bridges according to structural formula (B.2) include those compounds in which p is 2 or 3 and/or $R^1$, $R^7$, $R^{10}$ and $R^{10'}$ are each hydrogen.

In another preferred embodiment, bridges according to structural formula (B.2) include those compounds in which p is 0; $R^1$ and $R^7$ are each hydrogen; $R^{10}$ and $R^{10'}$ are each oxygen and the bond connecting substituent $R^{10'}$ is a double bond..

Mobility-modifying moiety MM constitutes the key feature of the mobility-modifing cyanine dyes of the invention. By manipulating MM, cyanine dyes having the desired electrophoretic mobility properties can be readily obtained. The mobility-modifying moiety generally comprises a pendant group bearing one or more charges through substitution with one or more of the same or different anionic or cationic substituents. The pendant group can be any moiety capable of being substituted with the desired number of charged substituents, but is typically a group having the structure —D—D', where D is a bond, ($C_1$–$C_6$) alkyldiyl, 2–6 membered heteroalkyldiyl or 1–6 membered acyclic heteroatomic bridge; and D' is ($C_1$–$C_6$) alkyl, 2–6 membered heteroalkyl, ($C_5$–$C_{14}$) aryl, ($C_5$–$C_{14}$) arylaryl, 5–14 membered heteroaryl or 5–14 membered heteroaryl-heteroaryl. Preferably, D is a bond when D' is ($C_1$–$C_6$) alkyl or 2–6 membered heteroalkyl; or D is ($C_1$–$C_6$) alkyleno when D' is ($C_5$–$C_{14}$) aryl, ($C_5$–$C_{14}$) arylaryl, 5–14 membered heteroaryl or 5–14 membered heteroaryl-heteroaryl. Preferred amongst the various D' groups are linear and branched ($C_{3–C_6}$) alkyls (especially alkanyls), linear and branched 3–6 membered heteroalkyls (especially heteroalkanyls), ($C_4$–$C_8$) cycloalkyls (especially cycloalkanyls and cyclohexanyl), 4–8-membered heterocycloalkyls (especially heterocycloalkanyls and piperidyl), ($C_5$–$C_{10}$) aryls (especially phenyl and naphthyl), ($C_5$–$C_{10}$) arylaryls (especially biaryls and biphenyl), 5–10 membered heteroaryls (especially pyridyl, pyrrolyl, indolyl, quinolinyl, thiophenyl, and benzothiophenyl) and 5–10 membered heteroaryl-heteroaryls (especially biheteroaryls composed of the above preferred heteroaryls).

Attaching aromatic rings such as aryl, arylaryl, heteroaryl and heteroaryl-heteroaryl groups directly to the heteroaromatic ring nitrogen of benzazole/benzazolium cyanine dyes has an unpredictably large effect on the absorbance and emission spectral properties of the cyanine dye. To avoid imposing these unpredictable spectral shifts, substituent D should be selected such that substituent D' is attached to the heteroaromatic ring nitrogen via an alkyldiyl group. When D' is ($C_5$–$C_{14}$) aryl, ($C_5$–$C_{14}$) arylaryl, 5–14 membered heteroaryl or 5–14 membered heteroaryl-heteroaryl, substituent D is typically a ($C_1$–$C_6$) alkyldiyl, preferably a (CI-$C_6$) alkyleno and more preferably a ($C_1$–$C_6$) alkano such as methano (—$CH_2$—), ethano (—$CH_2CH_2$—), propano (—$CH_2CH_2CH_2$—), etc. These D groups separate the mobility-modifing moiety from the heteroaromatic ring nitrogen so as not to adversely affect the spectral characteristics of the resultant dye. The aromatic rings may be attached directly to the benzazole/benzazolium ring nitrogen when spectral shifts are desired. The most preferred pendant groups according to structure —D—D' are those in which D is ($C_1$–$C_6$) alkyleno or ($C_1$–$C_6$) alkano and D' is phenyl, pyridyl, pyrrolyl, indolyl, quinolinyl, thiophenyl or benzothiophenyl; and those in which D is a bond and D' is ($C_3$–$C_6$) alkyl, especially ($C_3$–$C_6$) alkanyl.

Whether anionic or cationic charged substituents are used to substitute the pendant group will depend upon the direction of the desired mobility shift. When an increase in relative electrophoretic mobility is desired, the pendant group is substituted with anionic substituents. When a decrease in relative electrophoretic mobility is desired, the pendant group is substituted with cationic substituents. These substituents are described in more detail below.

The magnitude of the electrophoretic mobility shifts imparted by the mobility- modifying dyes of the invention relative to polynucleotides labeled with the corresponding unmodified dye (or another dye of interest) is related to the net charge of mobility- modifing moiety MM. The net charge of MM is in turn dependent upon the number and identities of charged substituents comprising the pendant group. For charged substituents that are completely ionized at approximately neutral pH (i.e., a pH in the range of 6 to 8), it has been discovered that the electrophoretic mobility increases linearly with net charge, i.e., each unit increase or decrease that the mobility-modifying moiety MM contributes to the net charge of the dye alters the electrophoretic mobility of polynucleotides labeled with the mobility-modifing dye by one nucleotide relative to polynucleotides labeled with the corresponding unmodified dye. Thus, approximately one net charge should be added to the mobility-modifing moiety for each nucleotide change in relative electrophoretic mobility desired.

In order to add charges in a predictable manner, substituents having permanent charges or that are completely ionized at the pHs commonly employed in nucleic acid electrophoresis applications (typically in the range of pH 6 to pH 10) are preferred. Suitable cationic substituents include, by way of example and not limitation, quarternary ammonium groups and groups having a $pK_a$ of 8 or greater, including for example —NRR, —NRRR$^+$, morpholino and piperidino, where each R is independently hydrogen or ($C_1$–$C_6$) alkyl (and any associated counterions). Preferred cationic substituents are quaternary ammoniums of the formula —N$^+$RRR, where each R is independently ($C_1$–$C_6$) alkyl. When multiple cationic substituents are used, each substituent may be the same or different. Suitable anionic substituents are groups having a $pK_a$ of about 6 or less, preferably 3 or less, and include by way of example and not limitation, —C(O)O$^-$, —P(O)(O$^-$)$_2$, —P(O)(OH)(O$^-$), —O—P(O)$_2$(O$^-$), —S(O)$_2$O$^-$ and —O—S(O)$_2$O$^-$ (including any associated counterions).

The charged substituents can be attached directly to the pendant group, or may be spaced away form the pendant group through one or more intervening atoms, such as through a ($C_1$–$C_6$) alkyldiyl, a ($C_1$–$C_6$) alkyleno, a 1–6 membered heteroalkyldiyl or a 2–6 membered heteroalkyleno group or, alternatively through a 2–6 membered acyclic bridge. Selecting the appropriate number(s) and identity(ies) of charged substituents to achieve a desired change in electrophoretic mobility based upon the $pK_a$ of the desired charged substituent, pH of the assay and net charge of the dye to be mobility-modified is within the capabilities of those having skill in the art.

In embodiments where the mobility-modifying cyanine dye includes a linking moiety comprising a linking group capable of covalently conjugating the dye to another molecule (discussed infra), the selectivity of the conjugation reaction can be conveniently controlled by selecting charged substituents that do not react or become activated under the conjugation conditions. Due to their non-reactive nature in the presence of a variety of conjugating reagents and conditions and their low $pK_a$, —S(O)$_2$O$^-$ and —O—S(O)$_2$O$^-$ are preferred anionic substituents, especially in instances where a carboxyl or carboxylate group is used to covalently conjugate the modified dye to the other molecules or substances.

In addition to the charged substituents, the pendant group may be fuirther substituted with one or more additional substituents without adversely affecting the spectral properties or relative electrophoretic mobility change achieved. Such substituents can serve a variety of purposes. For example, polar substituents can increase the water solubility of the mobility-modifing dye and sterically bulky substituents can decrease non-specific binding of the mobility-modifying dye, as well as decrease the interactions between dyes in molecules labeled with multiple dyes, thereby decreasing fluorescence quenching. Substituents capable of imparting these and other desirable properties will be apparent to those having skill in the art.

Virtually any substituent that does not adversely affect the imparted mobility shift and/or other desirable properties of the mobility-modifying dyes can be used. Typically, such additional substituents are uncharged at the desired pH of use. Thus, additional uncharged substituents that can be used to substitute the pendant group include, but are not limited to, ($C_1$–$C_6$) alkyl, ($C_1$–$C_6$) alkyl independently substituted with one or more W, 2–6 membered heteroalkyl, 2–6 membered heteroalkyl independently substituted with one or more W, ($C_5$–$C_{10}$) aryl, ($C_5$–$C_{10}$) aryl independently substituted with one or more W, ($C_5$–$C_6$) arylaryl, ($C_5$–$C_6$) arylaryl independently substituted with one or more W, ($C_6$–$C_{16}$) arylalkyl, ($C_6$–$C_{16}$) independently substituted with one or more W, 6–16 membered arylheteroalkyl, 6–16 membered arylheteroalkyl independently substituted with one or more W, 5–10 membered heteroaryl, 5–10 membered heteroaryl independently substituted with one or more W, 5∝6 membered heteroaryl-heteroaryl, 5–6 membered heteroaryl independently substituted with one or more W, 6–16 membered heteroarylalkyl, 6–16 membered heteroarylalkyl independently substituted with one or more W, 6–16 membered heteroaryl-heteroalkyl and 6–16 membered heteroaryl-heteroalkyl independently substituted with one or more W, wherein:

each W is independently —R, —X, =O, —OR, =S, —SR, —NRR, =NR, ($C_1$–$C_6$) perhaloalkyl, —$CX_3$, —CN, —OCN, —SCN, —NO, —$NO_2$, =$N_2$, —$N_3$, —NHOH, —$S(O)_2R$, —C(O)R, —C(S)R, —C(O)OR', —C(S)OR', —C(O)SR', —C(S)SR', and —C(NR)NRR;

each X is independently a halogen (preferably —F, —Cl or —Br);

each R is independently —H, —NR"R", —C(O)R", —$S(O_2)R$", ($C_1$–$C_6$) aikyl, ($C_1$–$C_6$) alkanyl, ($C_2$–$C_6$) alkenyl, ($C_2$–$C_6$) alkynyl, ($C_5$–$C_{10}$) aryl, ($C_6$–$C_{16}$) arylalkyl, 5–10 membered heteroaryl or 6–16 membered heteroarylalkyl; and each R' is independently ($C_1$–$C_6$) alkyl, ($C_1$–$C_6$) alkanyl, ($C_2$–$C_6$) alkenyl and ($C_2$–$C_6$) alkynyl, ($C_5$–$C_{10}$) aryl, ($C_6$–$C_{16}$) arylalkyl, 5–10 membered heteroaryl or 6–16 membered heteroarylalkyl; and each R" is independently —H, ($C_1$–$C_6$) alkyl, ($C_1$–$C_6$) alkanyl, ($C_2$–$C_6$) alkynyl, ($C_5$–$C_{10}$) aryl, ($C_6$–$C_{16}$) arlyalkyl, 5–10 membered heroaryl or 6–16 membered heteroarylalkyl. The various R, R' and R" groups can be further substituted with one or more of the same or different W groups, as defined above.

Such additional substituents are preferably groups that do not react or become activated under the conditions used to conjugate the dyes to other molecules or substances.

In a preferred embodiment, if present, any additional substituents are each independently selected from the group consisting of ($C_1$–$C_6$) alkyl, ($C_1$–$C_6$) alkanyl, ($C_2$–$C_6$) alkenyl, ($C_2$–$C_6$) alkynyl, —X, —OR, —NRR, —$CF_3$, —CN, —$NO_2$, and —C(O)R, where each R is independently hydrogen, —NR'R', —C(O)R—, —$S(O)_2R^1$, ($C_1$–$C_6$) alkyl, ($C_1$–$C_6$) alkanyl, ($C_2$–$C_6$) alkenyl or ($C_2$–$C_6$) alkynyl; each R' is independently hydrogen, ($C_1$–$C_6$) alkyl, ($C_1$–$C_6$) alkanyl, ($C_2$–$C_6$) alkenyl or ($C_2$–$C_6$) alkynyl; and X is —F, —Cl or —Br. Most preferably, the mobility-modifying moiety does not include any additional substituents.

As will be recognized by those having skill in the art, the hydrophobicity of the pendant group and the net charge of mobility modifying moiety MM can affect the water-solubility of the resultant mobility-modifying cyanine dye. As mobility-modifying dyes that are soluble in the aqueous buffers and solutions commonly employed in nucleic acid sequencing reactions and/or hybridization assays are desired, the hydrophobicity of the pendant group and net negative charge of mobility-modifying moiety MM should be adjusted so that the resultant dye is soluble in these buffers and solutions. Generally, the hydrophobicity of the pendant group can increase with increasing net charge of MM. Skilled artisans can readily select an appropriate combination of pendant group hydrophobicity and net charge of MM so as to retain the desired degree of solubility for particular applications.

It has been discovered that polynucleotides labeled with conventional cyanine dyes, such as the mono-sulfonated benzo cyanine dye BenzoCy5, illustrated below:

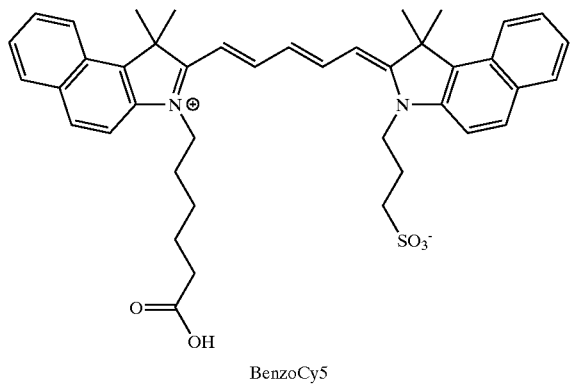

BenzoCy5 have electrophoretic mobilities that are up to four bases slower than polynucleotides labeled with dibenzorhodamine dyes (see, e.g., U.S. Pat. No. 5,936,087) or extended rhodamine dyes (see, e.g., U.S. application Ser. No. 09/325,243; attorney docket no. 4446). Replacing the mono-sulfonated alkyl group on the BenzoCy5 dye with the mobility modifier 2,4-bis-sulfonatophenylmethan-1-yl to yield the Mobility-Modifying BenzoCy5 dye illustrated below increased the relative electrophoretic mobilities of labeled polynucleotides by one base:

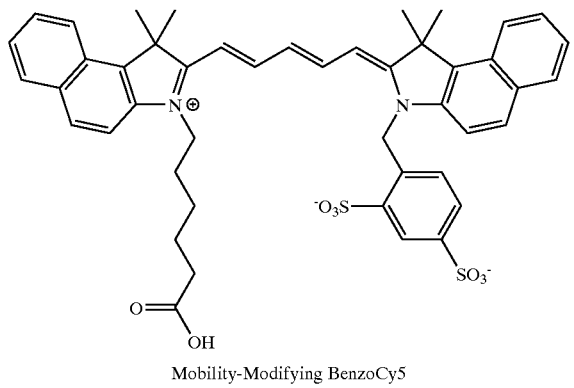

Mobility-Modifying BenzoCy5

As red-emitting dyes such as dibenzo- and extended rhodamines possess desirable characteristics for nucleic acid sequencing applications, preferred mobility-modifing dyes of the invention are those that have electrophoretic mobilities that are matched to these rhodamine dyes. Such mobility-modifying dyes will typically have mobility-modifying moieties that bear from 2 to 7 anionic substituents, more typically from 2 to 5 anionic substituents, depending upon the identity of the rhodamine dye being mobility-matched and the overall net charge of the substituent substituting the benzazole/benzazolium heteroaromatic rings.

Thus, in a preferred embodiment of the invention, mobility-modifying moiety MM is a substituted arylalkanyl according to structural formula (MM.1):

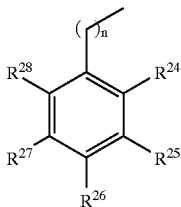

(MM.1)

wherein:

n is an integer from 1 to 6 (preferably 1 to 3);

$R^{24}$, when taken alone, is hydrogen, a strong anionic substituent, $—S(O)_2O^-$, or $—O—S(O)_2O^-$, or when taken together with $R^{25}$ is a benzo group or a benzo group independently substituted with one or more strong anionic substituents, $—S(O)_2O^-$, or $—O—S(O)_2O^-$ groups;

$R^{25}$, when taken alone, is hydrogen, a strong anionic substituent, $—S(O)_2O^-$, or $—O—S(O)_2O^-$, or when taken together with $R^{24}$ or $R^{26}$ is a benzo group or a benzo group independently substituted with one or more strong anionic substituents, $—S(O)_2O^-$, or $—O—S(O)_2O^-$ groups;

$R^{26}$, when taken alone, is hydrogen, a strong anionic substituent, $—S(O)_2O^-$, or $—O—S(O)_2O^-$, or when taken together with $R^{25}$ or $R^{27}$ is a benzo group or a benzo group independently substituted with one or more strong anionic substituents, $—S(O)_2O^-$, or $—O—S(O)_2O^-$ groups; and $R^{27}$, when taken alone, is hydrogen, a strong anionic substituent, $—S(O)_2O^-$, or $—O—S(O)_2O^-$, or when taken together with $R^{26}$ or $R^{28}$ is a benzo group or a benzo group independently substituted with one or more strong anionic substituents, $—S(O)_2O^-$, or $—O—S(O)_2O^-$ groups;

$R^{28}$, when taken alone, is hydrogen, a strong anionic substituent, $—S(O)_2O^-$, or $—O—S(O)_2O^-$, or when taken together with $R^2$ is a benzo group or a benzo group independently substituted with one or more strong anionic substituents, $—S(O)_2O^-$, or $—O—S(O)_2O^-$ groups, with the proviso that MM has a net charge of at least about −1 at a pH in the range of about pH 6 to pH 10.

In a particularly preferred embodiment according to structural formula (MM.1), at least two of $R^{24}$, $R^{25}$, $R^{26}$, $R^{27}$ and $R^{28}$ are other than hydrogen and n is 1.

In another particularly preferred embodiment according to structural formnula (MM.1), n is 1; $R^{24}$ and $R^{26}$ are each independently $—S(O)_2O^-$ or $—O—S(O)_2O^-$, preferably $—S(O)_2O^-$; and $R^{25}$, $R^{27}$ and $R^{28}$ are each hydrogen.

In another particularly preferred embodiment according to structural formula (MM.1), at least three of $R^{24}$, $R^{25}$, $R^{26}$, $R^{27}$ and $R^{28}$ are other tharn hydrogen and n is 1.

In still another particularly preferred embodiment according to structural formula (MM.1), at least four of $R^{24}$, $R^{25}$, $R^{26}$, $R^{27}$ and $R^{28}$ are other than hydrogen and n is 1.

In another particularly preferred embodiment according to structural formula (MM.1), at least five of $R^{24}$, $R^{25}$, $R^{26}$, $R^{27}$ and $R^{28}$ are other than hydrogen and n is 1.

In another preferred embodiment of the invention, mobility-modifying moiety MM is a substituted alkanyl according to structural formula (MM.2):

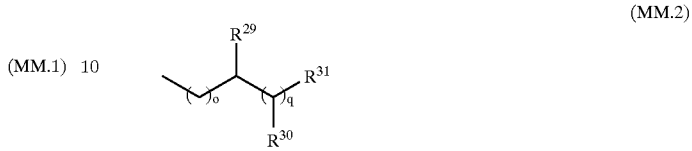

(MM.2)

wherein:

o is an integer from 1 to 3;

q is an integer from 1 to 3;

$R^v$ is a strong anionic substituent, $—S(O)_2O^-$ or $—O—S(O)_2O^-$, each $R^{30}$ is independently selected from the group consisting of hydrogen a strong anionic substituent, $—S(O)_2O^-$ and $—O—S(O)_2O^-$; and $R^{31}$ is selected from the group consisting of hydrogen, a strong anionic substitutent, $—S(O)_2O^-$, $—O—S(O)_2O^-$ and $—CH_3$, with the proviso that MM has a net charge of at least −2 at a pH in the range of about pH 6 to pH 10.

In a particularly preferred embodiment of mobility-modifying moieties according to structural formula (MM.2), at least one of $R^+$ is a strong anionic substituent, $—S(O)_2O^-$ or $—O—S(O)_2O^-$, preferably $—S(O)_2O^-$ or $—O—S(O)_2O^-$, In another particularly preferred embodiment according to structural formula (MM.2), o is 1; q is 1; $R^{30}$ is $—S(O)_2O^-$ or $—O—S(O)_2O^-$; and $R^3$ is $—CH_3$.

The mobility-modifying cyanine dyes of the invention include a linking moiety of the formula —L—LG, where L is a linker and LG is a linking group, for conjugating the dyes to other molecules or substances. The nature of linker L and linking group LG will depend upon the particular application and the type of conjugation desired. The linker can be hydrophilic or hydrophobic, long or short, rigid, semirigid or flexible, depending upon the particular application. The linker can be optionally substituted with one or more substituents or one or more additional linking groups, which may be the same or different than linking group LG, thereby providing a "polyvalent" linking moiety capable of conjugating with multiple molecules or substances. Preferably, however, linker L does not include such additional substituents or linking groups.

A wide variety of linkers L comprised of stable bonds suitable for spacing linking groups such as LG from molecules are known in the art, and include by way of example and not limitation, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. Thus, linker L may include single, double, triple or aromatic carbon-carbon bonds, nitrogen-nitrogen bonds, carbon-nitrogen, carbon-oxygen bonds and/or carbon-sulfur bonds, and may therefor include functionalities such as carbonyls, ethers, thioethers, carboxamides, sulfonamides, ureas, urethanes, hydrazines, etc. In one embodiment, linker L has from 1–20 non-hydrogen atoms selected from the group consisting of C, N, O, and S and is composed of any combination of ether, thioether, amine, ester, carboxamnide, sulfonmide, hydrazide, aromatic and heteroaromatic bonds.

Choosing a linker having properties suitable for a particular application is within the capabilities of those having skill in the art. For example, where a rigid linker is desired, L may be a rigid polypeptide such as polyproline, a rigid polyunsaturated alkyldiyl or an aryldiyl, biaryldiyl, arylarydiyl, heteroaryldiyl, biheteroaryldiyl, heteroaryl-heteroaryldiyl, etc. Where a flexible linker is desired, L may be a-flexible polypeptide such as polyglycine or a flexible saturated alkanyldiyl or heteroalkanyldiyl. Hydrophilic linkers may be, for example, polyalcohols or polyethers such as polyalkyleneglycols. Hydrophobic linkers may be, for example, alkydiyls or aryidiyls. Linkers suitable for use in most biological applications include ($C_1$–$C_{12}$) alkyldiyls, particularly alkanylenos such as methano (—$CH_2$—), ethano (—$CH_2$-$CH_2$—), propano (—$CH_2$-$CH_2$-$CH_2$—), butano (—$CH_2$-$CH_2$-$CH_2$-$CH_2$—), pentano (—$C_2$—$CH_2$-$CH_2$-$CH_2$-$CH_2$—) and hexano (—$CH_2$-$CH_2$-$CH_2$-$CH_2$-$CH_2$—); and ($C_6$-$C_{26}$) arylalkyldiyls, particularly those having the structural formula —$(CH_2)_i$—$\phi$—or —$(CH_2)_i$—$\psi$—,where each i is independently an integer from 1 to 6, $\phi$ is phenyldiyl (especially phena-1,3-diyl or phena-1,4-diyl) and $\psi$ is naphthyldiyl (especially naphtha-2,6diyl or naphtha-2,7-diyl). Analogs of these linkers L containing one or more heteroatoms, particularly heteroartoms selected from the group consisting of O, S, N and NR", where R" is hydrogen or ($C_1$–$C_6$) alkyl, can also be conveniently used to space linking group LG from the dyes of the invention. Linkers L tailored to specific applications are discussed in more detail, infra.

The dyes can be conjugated to a variety of different molecules and substances using a plethora of different conjugation means. For example, the conjugation can be mediated via hydrophobic interactions, ionic attraction, through the use of pairs of specific binding molecules such as biotin and avidinlstreptavidin or through covalent attachment. When conjugation via hydrophobic interactions is desired, linking group LG is a hydrophobic moiety that is capable of forming hydrophobic interactions with a hydrophobic moiety on the molecule or substance to be conjugated. Typical hydrophobic moieties include, but are not limited to, unsubstituted and substituted aryl, arylalkyl, arylaryl, heteroaryl, heteroarylaklyl and heteroaryl-heteroaryl groups. When the hydrophobic moiety is substituted, the substituents are preferably nonpolar, more preferably hydrophobic. Suitable hydrophobic moieties for forming nonovalent conjugates will be apparent to those of skill in the art.

When conjugation via ionic attraction is desired, linking group LG is a charged moiety having a net charge of a polarity opposite to a net charge on the molecule or substance to be conjugated. Typical charged moieties include, by way of example and not limitation, quaternary armunoniums, carboxylates and sulfonates, including salts thereof. A variety of cyclic quaternary ammoniums that are suitable for use as LG are described in U.S. Pat. No. 5,863,753 (see, e.g., Cols. 8–9), the disclosure of which is incorporated herein by reference.

When conjugation via pairs of specific binding molecules such as biotin and avidin/streptavidin is desired, LG will constitute one member of the binding pair. The molecule or substance to be conjugated will bear the other member of the binding pair. Where one of the members of the specific binding pair is a small molecule, such as biotin or a hormone, that member preferably comprises LG. A variety of biotins capable of being covalently linked to reactive futnctional groups such as amines are commercially available (e.g., Molecular Probes, Eugene, Oreg.). These biotins can be incorporated into the dyes of the invention to yield biotin-labeled dyes suitable for non-covalent conjugation to a variety of avidinistreptavidin-labeled molecules or substances.

Other representative specific binding pairs that can comprise linking group LG are provided in TABLE 1, infra.

TABLE 1

| Representative Specific Binding Pairs | |
|---|---|
| biotin | avidin (or streptavidin or anti-biotin) |
| IgG | protein A or protein G |
| drug | drug receptor |
| toxin | toxin receptor |
| carbohydrate | lectin or carbohydrate receptor |
| peptide | peptide receptor |
| protein | protein receptor |
| enzyme inhibitor | enzyme |
| DNA (RNA) | complementary DNA (RNA) |
| hormone | hormone receptor |

Preferably, linking group LG is capable of mediating conjugation via covalent attachment. In this preferred embodiment, linking group LG is typically a reactive functional group ($R_x$). Covalent conjugates are obtained by reacting a dye of the invention including a reactive group $R_x$ with a molecule or substance that contains, or is modified to contain, one or more fuinctional groups $F_x$ that are complementary to reactive group $R_x$, The exact identities of $R_x$ and $F_x$ will depend upon the nature of the desired covalent linkage and the chemistry used to form the covalent linkage. Generally, reactive group $R_x$ is a functional group that is capable of reacting with a complementary functional group $F_x$ under specified reaction conditions to form a covalent linkage. However, those of skill in the art will recognize that a variety of functional groups that are typically unreactive under certain reaction conditions can be activated to become reactive. Groups that can be activated to become reactive include, e.g., carboxylic acids and esters, including salts thereof. Such groups are referred to herein as "activatable precursors" and are specifically intended to be included within the expression "reactive group."

Pairs of reactive groups $R_x$ and complementary groups $F_x$ suitable for forming covalent linkages with one another under a variety of different reaction conditions are well-known. Any of these complementary pairs of groups can be used to covalently conjugate the dyes of the invention to other compounds or substances. In one convenient embodiment, reactive group $R_x$ and complementary functional group $F_x$ comprise complementary electrophiles and nucleophiles (or their respective activatable precursors). In another convenient embodiment, reactive group $R_x$ is a photoactivatable group that becomes chemically reactive only after illumination with light of an appropriate wavelength and complementary finctional group $F_x$ is a group capable of forming a covalent linkage with the chemically reactive species. Such photoactivatable groups can be conveniently used to photo cross-link the dyes of the invention to other molecules and/or substances.

A plethora of complementary electrophile/nucleophile pairs and photoactivatable groups suitable for covalently conjugating two molecules together are well-known. The actual choice of complementary pairs and/or photoactivatable group will depend upon a variety of factors, and will be apparent to those of skill in the art. Examples of complementary electrophiles and nucleophiles suitable for use in a wide variety of contexts are shown in TABLE 2, where reaction between the indicated electrophilic and nucleophilic species yields the indicated covalent linkage. Conditions under which the covalent linkages may be formed are well-known.

TABLE 2

Examples of Some Routes to Useful Covalent Linkages

| Electrophilic Group | Nucleophilic Group | Resulting Linkage |
|---|---|---|
| activated esters | amines/anilines | carboxamides |
| acyl azides* | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | carboxylic acids | esters |
| acyl halides | amines/anilines | amides |
| acyl halides | alcohols | esters |
| acyl halides | thiols | thioesters |
| alkyl halides | thiols | thioesters |
| alkyl sulfonylhalides | amines | alkyl sulfonamides |
| alkyl sulfonylhalides | alcohols/phenols | alkyl sulfonates |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Acyl azides can rearrange to isocyanates.

As understood in the art, the "activated esters" of TABLE 2 generally have the formula —C(O)Ω, where Ω is a good leaving group. Exemplary good leaving groups include, by way of example and not limitation: oxysuccinimidyl; N-succinimidyl; oxysulfosuccinimidyl; 1-oxybenzotriazolyl; and —$OR^b$, where $R^b$ is selected ftrom the group consisting of ($C_4$–$C_{20}$) cycloalkyl (e.g., cyclohexyl), 4–20 membered heterocycloalkyl, ($C_5$–$C_{20}$) aryl, ($C_5$–$C_{20}$) aryl substituted with one or more of the same or different electron-withdrawing groups (e.g., —$NO_2$, —F, —Cl, —CN, —$CF_3$, etc.), 5–20 membered heteroaryl, 5–20 membered heteroaryl substituted with one or more of the same or different electron-withdrawing groups, n-dialkylaminoalkyls (e.g., 3dimethylaminopropyl) and N-morpholinomethyl, or $R^b$ is used to form an anhydride of the formula —$OCOR^b$ or —$OCNR_bNHR^c$, where $R^b$ and $R^c$ are each independently selected form the group consisting of ($C_1$–$C_6$) alkyl, ($C_1$–$C_6$) perhaloalky, ($C_1$–$C_6$) perfluoroalky and ($C_1$–$C_6$) alkoxy. A preferred activated ester is NHS ester.

Exemplary photoactivatable groups suitable for conjugation via light-activated cross-linking include, but are not limited to, azido (—$N_3$), 4-azido-phenyl and 2-nitro4-azidophenyl. Conjugation using photoactivatable groups typically-involves illuminating a mixture comprising the photoactivatable dyes and the molecule or substance to be conjugated, followed by separation of unreacted dyes and byproducts.

As will be recognized by those of skill in the art, reactive group $R_x$ can comprise any of the electrophilic, nucleophilic or photoactivatable groups discussed above. The selection of reactive group $R_x$ used to covalently conjugate the dyes of the invention to the other molecule or substance typically depends upon the identity of the complementary functional group $F_x$ on the molecule or substance to be conjugated. The types of complementary functional groups typically present on molecules or substances to be conjugated include, but are not limited to, amines, thiols, alcohols, phenols, aldehydes, ketones, phosphates, imidazoles, hydrazines, hydroxylamines, mono- and disubstituted amines, halides, epoxides, sulfonate esters, carboxylic acids or carboxylates, or a combination of these groups. A single type of complementary functional group may be available on the molecule or substance (which is typical for polysaccharides), or a variety of different complementary functional groups may be available (e.g. amines, thiols, alcohols, phenols), which is typical for proteins. The molecule or substance may be conjugated to more than one dye, which may be the same or different Although some selectivity can be obtained by carefilly controlling the reaction conditions, selectivity of conjugation is best obtained by appropriate choice of reactive group $R_x$ in light of the available complementary functional group(s) $F_x$. In instances where the molecule or substance to be conjugated does not contain available complementary finctional group(s) $F_x$, it can be modified to contain such groups using any of a variety of standard techniques.

In a preferred embodiment, reactive group $R_x$ is a group that reacts with, or that can be readily activated to react with, an amine, a thiol or an alcohol. A preferred reactive group $R_x$ capable of reacting with a hydroxyl is a phosphoramidite. A preferred reactive group $R_x$ capable of reacting with an amine is a carboxylic acid or an activated ester, most preferably a N-hydroxysuccinimidyl (NHS) ester. The NHS ester may be conveniently obtained by reacting a dye of the invention including a carboxylic acid reactive group $R_x$ with N-hydroxysuccinimide in the presence of an activating agent (e.g., dicyclohexylcarbodiimide ) according to known methods. The preparation of dyes having phosphoramidite reactive groups are described in a later section.

For a discussion of the various reactive groups $R_x$ and respective complementary functional groups $F_x$ that can be conveniently used to covalently conjugate the dyes of the invention to a variety of biological and other molecules or substances, as well as reaction conditions under which the conjugation reactions can be carried out, see Haugland, 1996, *Molecular Probes Handbook of Fluorescent Probes and Research Chemicals*, Molecular Probes, Inc.; Brinkley, 1992, Bioconjugate Chem. 3:2 and Garman, 1997, *Non-Radioactive Labelling: A Practical Approach*, Academic Press, London, as well as the references cited in all of the above. Additional suitable groups can be found in U.S. Pat. No. 5,268,486 (see, e.g., Col. 15–17).

The mobility-modifying dyes of the invention will now be firther described by reference to various preferred embodiments. According to one preferred embodiment of the invention, the mobility-modifying cyanine dyes are compounds according to structural formula (I.A):

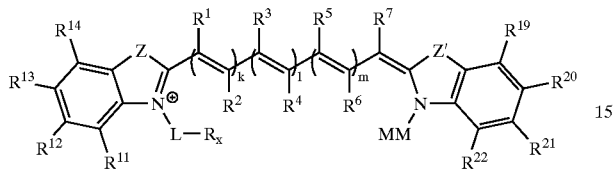

(I.A)

wherein:

$R^1$, $R^2$, $R^3$, $R^4$, $R^5$, $R^6$, and $R^7$ are each independently selected from the group consisting of hydrogen, halogen, —F, —Cl, —CN, —CF$_3$, (C$_1$–C$_6$) alkyl, (C$_5$–C$_{14}$) aryl or 5–14 membered heteroaryl;

k is an integer from 0 to 1;

l is an integer from 0 to 1;

m is an integer from 0 to 1;

Z is selected from the group consisting of —S—, —O—, —Se— and —CR$^8$R$^9$—, where R$^8$ and R$^9$ when taken alone, are each independently (C$_1$–C$_6$) alkyl, or when taken together are (C$_{4-C5}$) alkyleno or (C$_4$–C$_5$) alkano;

$Z^1$ is selected from the group consisting of —S—, —O—, —Se— and —CR$^8$R$^9$—, where Rland R$^9$, when taken alone, are each independently (C$_1$–C$_6$) alkyl, or when taken together are (C$_4$–C$_5$) alkyleno or (C$_4$–C$_5$) alkano;

L and $R_x$ are a linker and a reactive group, respectively, as previously described;

MM is a mobility-modifying moiety as previously described;

$R^{11}$, $R^{12}$, $R^{13}$, $R^{14}$, $R^{20}$, $R^{21}$ and $R^{22}$, when taken alone, are each independently selected from the group consisting of hydrogen, (C$_1$–C$_6$) alkyl, (C$_1$–C$_6$) alkyl independently substituted with one or more W, 2–6 membered heteroalkyl, 2–6 membered heteroalkyl independently substituted with one or more W, (C$_5$–C$_{10}$) aryl, (C$_5$–C$_{10}$) aryl independently substituted with one or more W, (C$_5$–C$_6$) arylaryl, (C$_5$–C$_6$) arylaryl independently substituted with one or more W, (C$_6$–C$_{16}$) arylalkyl, (C$_6$–C$_{16}$) independently substituted with one or more W, 6–16 membered arylheteroalkyl, 6–16 membered arylheteroalkyl independently substituted with one or more W, 5–10 membered heteroaryl, 5–10 membered heteroaryl independently substituted with one or more W, 5–6 membered heteroaryl-heteroaryl, 5–6 membered heteroaryl independently substituted with one or more W, 6–16 membered heteroarylalkyl, 6–16 membered heteroarylalkyl independently substituted with one or more W, 6–16 membered heteroaryl-heteroalkyl and 6–16 membered heteroaryl-heteroalkyl independently substituted with one or more W, or when taken together with an adjacent RI are each independently selected from the group consisting of (C$_6$–C$_{10}$) aryleno, (C$_6$–C$_{10}$) aryleno independently substituted with one or more W, 6–10 membered heteroaryleno and 6–10 membered heteroaryleno independently substituted with one or more W;

each W is independently —R, —X, =O, —OR, =S, —SR, —NRR, =NR, (C$_1$–C$_6$) perhaloalkyl, —CX$_3$, —CN, —OCN, —SCN, —NO, —NO$_2$, =N$_2$, —N$_3$, —NHOH, —S(O)$_2$R, —C(O)R, —C(S)R, —C(O)OR', —C(S)OR', —C(O)SR', —C(S)SR', and —C(NR)NRR;

each X is independently a halogen (preferably —F, —Cl or —Br);

each R is independently —H, —NR"R", —C(O)R", —S(O)R", (C$_1$–C$_6$) alkyl, (C$_1$–C$_6$) alkanyl, (C$_2$–C$_6$) alkenyl, (C$_2$–C$_6$) alkynyl, (C$_5$–C$_{10}$) aryl, (C$_6$–C$_{16}$) arylalkyl, 5–10 membered heteroaryl or 6–16 membered heteroarylalkyl;

each R' is independently (C$_1$–C$_6$) alkyl, (C$_1$–C$_6$) alkanyl, (C$_2$–C$_6$) alkenyl and (C$_2$–C$_6$) alkynyl, (C$_5$–C$_{10}$) aryl, (C$_6$–C$_{16}$) arylalkyl, 5–10 membered heteroaryl or 6–16 membered heteroarylalkyl; and each R" is independently —H, (C$_1$–C$_6$) alkyl, (C$_1$–C$_6$) alkanyl, (C$_2$–C$_6$) alkynyl, (C$_5$–C$_{10}$) aryl, (C$_6$–C$_{16}$) arylalkyl, 5–10 membered heteroaryl or 6-16 membered heteroarylalkyl. The various R, R' and R" groups can be further substituted with one or more of the same or different W groups, as defined above.

One class of particularly preferred dyes according to structural formula (I.A) includes those compounds in which L, $R_x$ and mobility-modifying moiety MM constitute one of their respective previously-described preferred embodiments.

Another class of particularly preferred dyes according to structural formula (P.A) includes those compounds in which $R^1$, $R^2$, $R^3$, $R^4$, $R^5$, $R^6$, and $R^7$ are each hydrogen and/or the sumn of k, l and m is 2.

Still another class of particularly preferred dyes according to structural formula (I.A) includes those compounds in which Z and Z' are the same; $R_{20}$ and $R^{13}$ are the same; $R^{21}$ and $R^{12}$ are the same; and/or $R^{22}$ and $R^{11}$ are the same.

Yet another class of particularly preferred dyes according to structural formula (I.A) includes those compounds in which any arylenos formed by taking two adjacent $R^{11}$ together are each independently benzo or benzo substituted with one or more of the same or different strong anionic substituents.

Yet another class of particularly preferred dyes according to structural formula (I.A) includes those compounds in which Z is —CR$^8$R$^9$—, where R$^8$ is (C$_1$–C$_3$) alkanyl and R$^9$ is (C$_1$–C$_3$) alkanyl; and Z' is —CR$^8$R$^9$, where R$^8$ is (C$_1$–C$_3$) alkanyl and R$^9$ is (C$_1$–C$_3$) alkanyl. Even more preferred are those compounds in which Z and Z' are the same, especially dyes in which R$^8$, R$^8$, R$^9$, R$^9$ are the same.

Yet another class of particularly preferred compounds according to structural formula (I.A) includes compounds according to structural formulae (I.D), (I.E), (I.F), (I.G), (I.H) (I.I), (I.J) and (I.K):

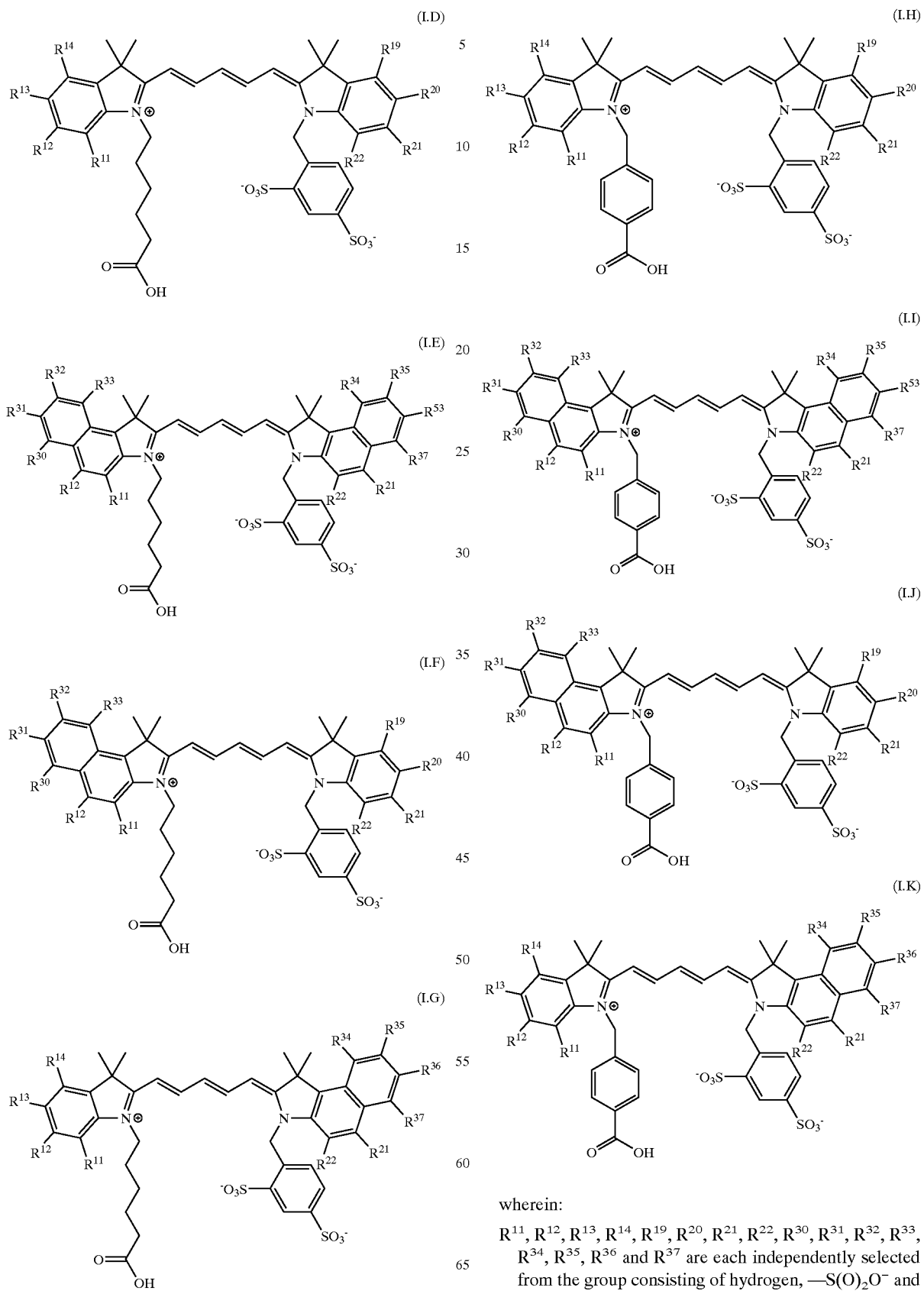
wherein:
$R^{11}, R^{12}, R^{13}, R^{14}, R^{19}, R^{20}, R^{21}, R^{22}, R^{30}, R^{31}, R^{32}, R^{33}, R^{34}, R^{35}, R^{36}$ and $R^{37}$ are each independently selected from the group consisting of hydrogen, —S(O)$_2$O$^-$ and —O—S(O)$_2$O$^-$.

Especially preferred amongst the compounds of the structural formulae (I.D), (I.E), (I.F), (I.G), (I.H), (I.I), (I.J) and/or (I.K) are those compounds in which $R^{11}$, $R^{12}$, $R^{13}$, $R^{14}$, $R^{19}$, $R^{20}$, $R^{21}$, $R^{22}$, $R^{30}$, $R^{31}$, $R^{32}$, $R^{33}$, $R^{34}$, $R^{35}$, $R^{36}$ and $R^{37}$ are each hydrogen A particularly preferred class of mobility-modifying dyes according to structural formulae (I.D) and/or (I.H) are those compounds in which one or two of $R^{11}$, $R^{12}$, $R^{13}$ and $R^{14}$ and/or one or two of $R^{19}$, $R^{20}$, $R^{21}$ and $R^{22}$, are each independntly —$S(O)_2O^-$ or —O—$S(O)_2O^-$; and the remaining Rs are each hydrogen.

A particularly preferred class of mobility-modifying dyes according to structural formulae (I.E) and/or (I.I) are compounds in which $R^{11}$, $R^{12}$, $R^{21}$, and $R^{22}$ are each hydrogen; one or two of $R^{30}$, $R^3$, $R^{32}$ and $R^{33}$ and/or one or two of $R^{34}$, $R^{35}$, R36 and $R^{37}$ are each independently —$S(O)_2O^-$ or —O—$S(O)_2O^-$; and the remaining Rs are each hydrogen.

A particularly preferred class of mobility-modifing dyes according to structural formulae (I.F) and/or (I.J) are compounds in which $R^{11}$ and $R^{12}$ are each hydrogen; one or two of $R^{30}$, $R^{31}$, $R^{32}$ and $R^{33}$ and/or one or two of $R^{19}$, $R^{20}$, $R^{21}$ and $R^{22}$ are each independently —$S(O)_2O^-$ or —O—$S(O)_2O^-$; and the remaining Rs are each hydrogen.

A particularly preferred class of mobility-modifying dyes according to structural formulae (I.G) and/or (I.K) are compounds in which $R^{21}$ and $R^{22}$ are each hydrogen; one or two of $R^{11}$, $R^{12}$, $R^{13}$ and $R^{14}$ and/or one or two of $R^{34}$, $R^{35}$, $R^{36}$ and $R^{37}$ are each independently —$S(O)_2O^-$ or —O—$S(O)_2O^-$; and the remaining Rs are each hydrogen.

Representative exemplary preferred dyes according to structural formulae (I.D), (I.E), (I.F) and/or (I.G) are provided in the Examples section. The corresponding dyes according to structural formulae (I.H), (I.I), (I.J) and/or (I.K) are also preferred.

Those of skill in the art will appreciate that the various compounds encompassed by formulae (I), (I.A), (I.D), (I.E), (I.F), (I.G), (I.H), (I.I), (I.J) and (I.K), as well as their various conjugates and reagents described infra, may exhibit the phenomenon of tautomerism. Depending on the various substituents, rnany of these compounds also contain chiral centers. The various compounds may further exhibit the phenomena of conformational isomerism or geometric isomerism. As the formulae drawings within this specification can represent only one of the possible tautomeric, enantiomeric, conformational isomeric or geometric isomeric forms, it should be understood that the invention encompasses any tautomeric, enantiomeric, conformational isomeric or geometric isomeric forms of the compounds which exhibit the desired activities and/or properties described herein.

Moreover, all of the mobility-modifying cyanine dye compounds described herein, and consequently their respective conjugates and reagents, include charged groups. It is to be understood that all of the compounds described herein include any necessary counterions, even though not explicitly illustrated. Typical negatively charged counter ions to balance the heteroaromatic imminium nitrogen and/or positively charged substituents composing mobility-modifying moiety MM include, but are not limited to, chloride, bromide, iodide, sulfate, alkanesulfonate, alkenesulfonate, alkynesulfonte, arylsulfonate, phosphate, perch lorate, periodate, tetrafluoroborate, tetrarylborate, nitrate and anions of aromatic or aliphatic carboxylic acids. Typical positively charged counter ions to balance anionic substituents on the mobility-modifing moiety include, but are not limited to $Na^+$, $K^+$, $Li^+$, quaternary ammoniums, etc. Counter ions suitable for balancing other substituents will depend upon the charge of the substituent, and will be apparent to those having skill in the art.

4.4 Methods of Synthesis

The synthetic route to the mobility-modifying cyanine dyes of the invention requires the synthesis of three precursors: (i) a parent benzazolium ring system E having a mobility-modifying moiety MM attached to the benzazolium ring nitrogen; (ii) a parent benzazolium ring system A having a linking moiety (-L-LG) attached to the benzazolium ring nitrogen; and (iii) a source for the bridge linking rings A and E. While the mobility- modifying dyes of the invention have not been previously described, the chemistry that is required to prepare and combine these precursors so as to yield any of the compounds described herein is generally well-understood by one skilled in the art.

For example, methods suitable for synthesizing benzazolium precursors according to structural formulae (A.1) and (E.1) are described in U.S. Pat. No. 5,436,134 (particularly at Cols. 13–33):

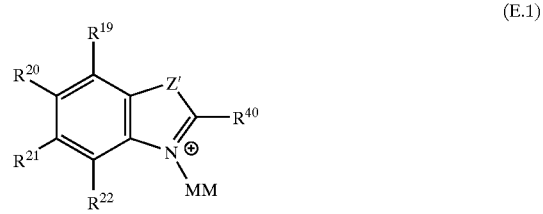

(E.1)

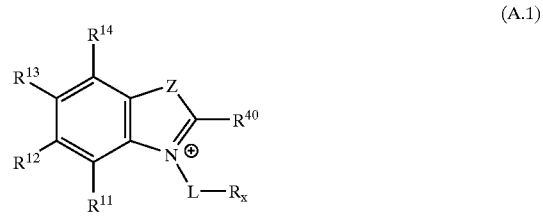

(A.1)

Additional suitable methods are described in U.S. Pat. Nos. 5,863,753; 5,321,130; 5,410,030; 5,534,416; 5,582,977 and 5,658,751, as well as the various references cited therein.

In structural formulae (A.1) and (E.1), MM, L, $R_x$, Z, $Z^1$, $R^{11}$, $R^{12}$, $R^{13}$, $R^{14}$, $R^{19}$, $R^{20}$, $R^{21}$ and $R^{22}$ are as previously defined for structural formula (I.A) and $R^{40}$ and $R^{40'}$ are substituents whose nature is determined by the synthetic method utilized to couple the benzazolium precursor with each other. When the bridge joining the two heterocycles is a metine bridge, then one of $R^{40}$ and $R^{40'}$ is alkylthio (commonly methylthio), chloro, bromo, or iodo and the other one of $R^{40}$ and $R^{40'}$ is methyl. The methyl is incorporated into the final compound.

Compounds in which the heterocycles are joined by a polymethine bridge according to structural formula (B.1) or a cyclic alkylene bridge according to structural formula (B.2) may be synthesized by methods that are well-known in the art. Preferred methods of synthesis, exemplified with certain preferred mobility-modifying dyes including a linking moiety of the formula -L-$R_x$ and a polymethine bridge are outlined in Schemes (I) and (II), below. The various steps can be adapted as necessary to synthesize the full range of mobility-modifying dyes according to the invention.

In Schemes (I) and (II), n, $R^{24}$, $R_{25}$, $R^{26}$, $R^{27}$ and $R^{28}$ are as previously defmed for structural formula (MM.1); Z, Z', L, $R_x$, $R^{11}$, $R^{12}$, $R^{13}$, $R^{14}$, $R^{19}$, $R^{20}$, $R^{21}$ and $R^{22}$ are as previously defined for structural formula (I.A); Ph is phenyl; Ac$_2$O is acetic anhydride; Ac is acetate; and EtOH is ethanol.

Scheme (I)

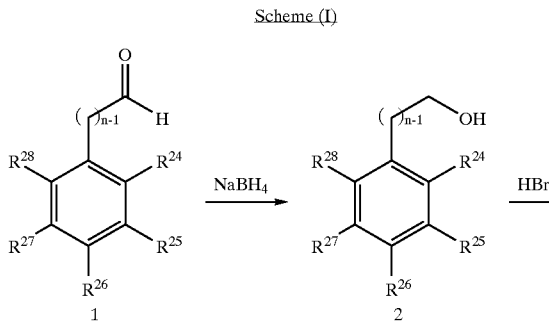

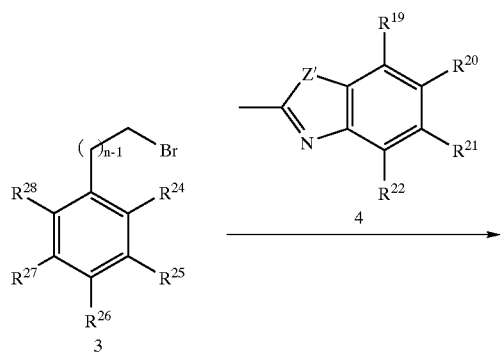

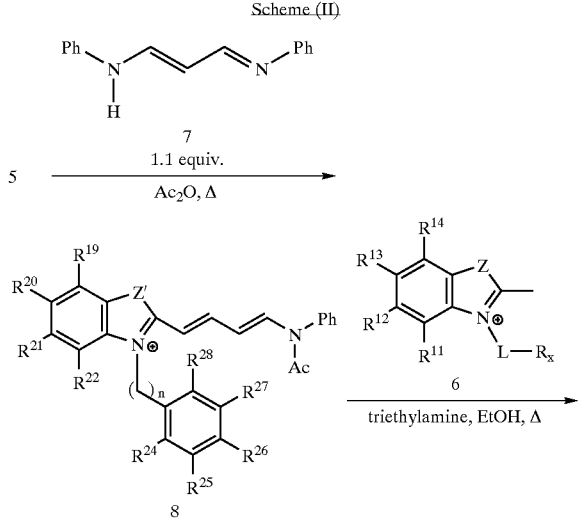

Scheme (II)

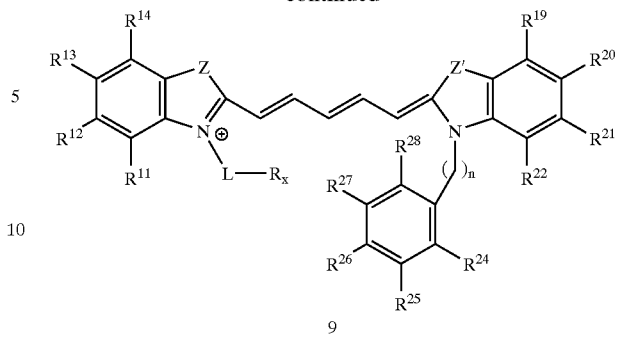

-continued

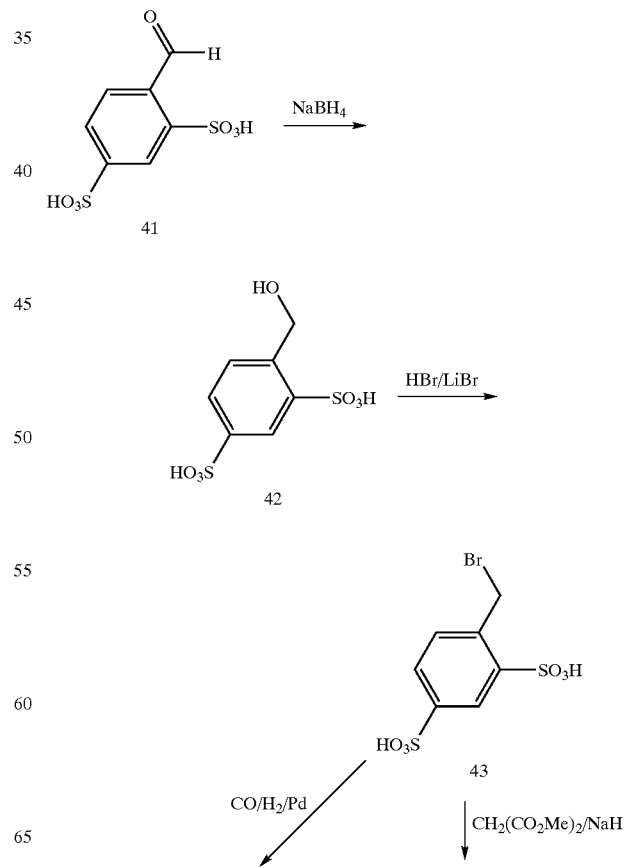

Referring to Scheme (I), benzazolium precursor 5 is obtained by reducing an aldehyde precursor of the desired mobility modifying moiety 1 to its corresponding alcohol 2 in the presence of a reducing agent such as sodium borohydride. Alcohol 2 is then treated with HBr to yield the corresponding bromide 3. Bromide 3 is reacted with benzazole 4 in nitrobenzene solvent under argon atmosphere and 190° C. to yield the corresponding mobility-modifying precursor 5. Compounds 1 are either commercially available or can be prepared using well-known techniques.

Schemes for synthesizing certain exemplary aromatic precursors 3 and analogous aliphatic precursors useful for mobility-modifying benzazole ring 11 to yield mobility-modified cyanine precursor 12 according to Scheme (I) are illustrated in Schemes (Ia) and (Ib), respectively, below.

Scheme (Ia)

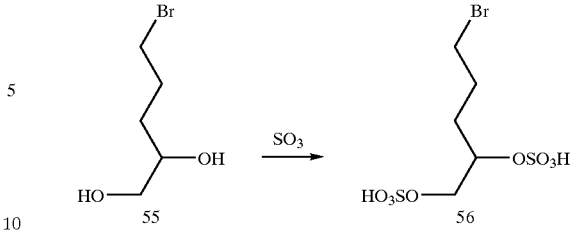

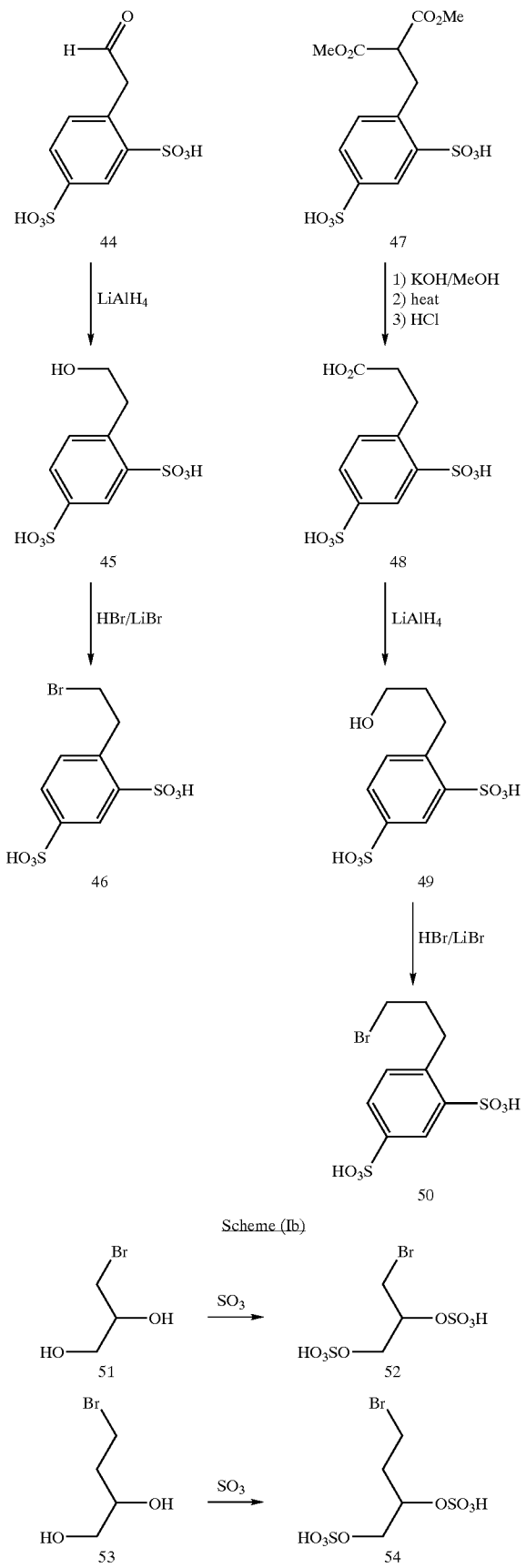

Referring to Scheme (Ia), commercially available aldehyde 41 is reduced to the alcohol with sodium borohydride in water, yielding the benzyl alcohol 42, which upon treatment with hydrogen bromide and a metal bromide salt, yields the benzylic bromide 43. Benzylic bromide 43 can be used to fimctionalize the indolinine precursor to the cyanine dye with the disulfonate mobility modifier according to Scheme (I), or can be used as a starting material to increase the length of the linkage between the sulfonated aromatic ring and the indolinine nitrogen. As examples, 43 can be carbonylated with carbon monoxide and hydrogen with a palladium catalyst to yield aldehyde 44; reduction of 44 to the alcohol 45 with lithium aluminum hydride, followed by treatment of 45 with hydrobromic acid with lithium bromide yields the bromide 46 which can be used to functionalize the indolinine precursor to the cyanine dye according to Scheme (I) with an ethyl linker between the aromatic disulfonate and the indolinine nitrogen. In addition, 43 can be condensed with the sodium salt of dimethylmalonate to yield the dimethyl ester 47; hydrolysis of the ester to the bis-acid, which is decarboxylated to the mono-acid with heat, followed by isolation work-up with hydrochloric acid yields the free acid 48; reduction of 48 with lithium aluminum hydride to yield alcohol 49, followed by treatment of 49 with hydrobromic acid with lithium bromide yields the bromide 50 which can be used to functionalize the indolinine precursor to the cyanine dye according to Scheme (I) with a propyl linker between the aromatic disulfonate and the indolinine nitrogen.

Referring to Scheme (Ib), commercially available propandiol bromide 51 can be converted to bromopropane disulfate 52, and propandiols 53 (synthesized according to Serves et al., 1995, Phosphorous, Sulfur Silicon Relat. Elem 101:75–82) and 55 (synthesized according to Ni and Matile, 1998, Chem. Commun. pp. 755–56) can be converted to bromopropane disulfates 54 and 56, respectively, by treatment of the diols with sulfur trioxide, according to standard procedures (see, e.g, Everett Gilbert, "Sulfonation and Related Reactions," Robert E. Krieger Publishing Co, Huntington, New York, 1977, Chapter 6). Bromodisulfates 52, 54, and 56 can be used to fnctionalize the indolinine cyanine dye precursor with the disulfate mobility modifier according to Scheme (I) to yield disulfates with methyl, ethyl, and bromo linkers, respectively, between the indolinine nitrogen and the disulfate portion of the chain.

The various precursors of the mobility-modifing dye are then condensed to form the completed dye, as illustrated in Scheme (II), supra. Referring to Scheme (II), bridge precursor 7 is reacted with mobility-modifying precursor 5 in the presence excess anhydride and heated to reflux (typically about 120 to 140° C.) to yield compound 8. Compound 8 is then condensed with benzazolium 6 (which is synthesized according to Scheme (I). or standard methods) in the presence of a base and a polar solvent to yield mobility-modifying dye 9.

Those of skill in the art will recognize that while Scheme II depicts a specific bridge precursor 7, analogous precursors can be used to create mobility-modifing cyanine dyes containing different bridges using, for example, the methods described in U.S. Pat. Nos. 5,436,134, 5,863,753, 5,321,130, 5,410,030, 5,534,416, 5,582,977 and 5,658,751, as well as the various references cited therein. In addition, depending upon thenature of the Z, Z', L, $R_x$ and/or the various R substituents, these groups may require protection during all or some of the synthesis steps, and/or reaction with activating groups for further derivatization of the dye. Groups suitable for protecting and/or activating specific functionalities, as well as methods for their removal, are well-known and will be apparent to those of skill in the art. Guidance for selecting suitable protecting groups can be found, for example, in Greene & Wuts, 1991, *Protective Groups in Organic Synthesis,* 2nd Ed., John Wiley & Sons, Inc., New York.

A significant advantage of Schemes (I) and (II) is that $—S(O)_2O^-$ and $—O—S(O)_2O^-$ groups on either mobility-modifier or the parent heteroaromatic rings are not reactive under the conditions used, and therefore do not require protection. In addition, when reactive group $R_x$ is a carboxyl or a salt thereof, it does not require protection during the synthesis conditions outlined in Scheme (II). Thus, Schemes (I) and (II) are the preferred method of synthesizing compounds according to structural formulae (I.D), (I.E), (I.F), (I.G), (I.H). (I.I), (I.J) and (I.K).

4.5 Reagents and Conjugates Incorporating The Dye Compounds

In another aspect, the present invention comprises reagents labeled or conjugated with the mobility-modifing cyanine dyes of the invention. Reagents of the invention can be virtually any molecule or substance to which the dyes of the invention can be conjugated, including by way of example and not lirnitation, proteins, polypeptides, polysaccharides, nucleosides, nucleotides, polynucleotides, lipids, solid supports, organic and inorganic polymers, and combinations and assemblages thereof, such as chromosomes, nuclei, living cells (e.g., bacteria or other microorganisms, mammalian cells, tissues, etc.), and the like. The dyes are conjugated with the reagent via the linking moiety by a variety of means, including hydrophobic attraction, ionic attraction, covalent attachment or with the aid of pairs of specific binding molecules, as previously described. Preferably, the dyes are conjugated via covalent attachment.

Conjugation typically results from mixing appropriate reactive mobility-modifying cyanine dyes and the molecules or substances to be conjugated in a suitable solvent in which both are soluble using methods well-known in the art, followed by separation of the conjugate from any unconjugated starting materials or unwanted by-products. The dye conjugate can be stored dry or in solution for later use.

4.5.1 Nucleosideltide Reagents

A preferred class of conjugates include nucleosides/tides and nucleoside/tide analogs that are labeled with the dyes of the invention. Such labeled nucleosides/tides are particularly useful for labeling polynucleotides formed by enzymatic synthesis, e.g., labeled nucleotide triphosphates used in the context of template-directed primer extension, PCR amplification, Sanger-type polynucleotide sequencing, and/or nick-translation reactions. Referring to Scheme (III), below, dye-labeled nucleoside/tides and/or nuleoside/tide analog conjugates are generally obtained by condensing a nucleoside/tide or nucleoside/tide analog modified to contain a linking moiety of the formula $-L-F_x$ (35) with a dye according to structural formula (I.A) in which LG is a reactive group $R_x$ (36) to yield a dye-labeled nucleosides/tides or nucleoside/tide analog according to structural formula (II).

Scheme (III)

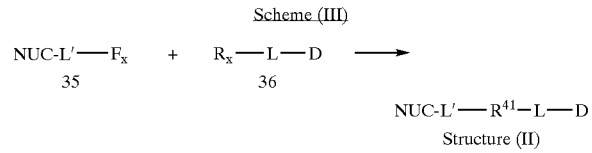

In Scheme (III), L and $R_x$ are a linker and a reactive group, respectively, as previously described; D represents a mobility-modifing dye chromophore; $F_x$ is complementary functional group, as previously described; L' is a bond or a second linker; NUC represents a nucleoside/tide or a nucleoside/tide analog; and $R_{41}$ represents a covalent linkage formed by reaction between $R_x$ and $F_x$, as will be described in more detail, below.

During the condensation, reactive group $R_x$ and complementary functional group $F_x$ react to form covalent linkage $R^{41}$. Thus, it will be recognized by those of skill in the art that reactive group $R_x$ and complementary functional group $F_x$ can each constitute respective members of the various pairs of complementary groups described supra, such as the various pairs of complementary electrophiles and nucleophiles listed in TABLE 2. Preferably, one of $R_x$ or $F_x$ (preferably $F_x$) is an amine, thiol or hydroxyl group, most preferably a primary amine group, and the other one of $R_x$ or $F_x$ (preferably $R_x$) is a group capable of reacting with an amine, thiol or hydroxyl, most preferably a carboxylic acid or a salt, ester or activated ester thereof. Thus, a particularly preferred covalent linkage $R^{41}$ is an amide of the formula $—C(O)NR^{45}—$, where $R^{45}$ is hydrogen or $(C_1–C_6)$ alkyl.

Complementary functional group $F_x$ is attached to NUC via linker L'. Complementary functional group $F_x$ may be attached directly to NUC, in which case L' represents a bond, or it may be spaced away from NUC by one or more intervening atoms, in which case L' represents a linker. Any of the linkers L previously described in connection with the mobility-modifying cyanine dyes per se can be used for linker L'. Preferred linkers L' are described in more detail below.

Complementary functional group $F_x$ may be attached to NUC at a variety of different positions, e.g., the nucleobase, the sugar and/or the phosphate ester or other backbone moiety. Nucleosides/tides and nucleoside/tide analogs that are appropriately modified at these various positions such that they can be conjugated with dye pairs according to the invention are known in the art. Preferably, complementary group $F_x$ is attached to the nucleobase via linker L'. When the nucleobase is a 7-deazapurine, L' is usually attached to the C7 or C8 position of the nucleobase. When the nucleobase is a pyrimidine, L' is usually attached to the C5 position of the nucleobase. When the nucleobase is a purine, L' is usually attached to the C7 position of the nucleobase. Linkers L' useful for covalently conjugating the dyes of the invention to the nucleobase of NUC are described in U.S. Pat. No. 5,821,356, U.S. Pat. No. 5,770,716 and U.S. application Ser. No. 08/833,854 filed Apr. 10, 1997, the disclosures of which are incorporated herein by reference.

Preferred linkers L' for covalently conjugating the dyes of the invention to the nucleobase of NUC include $(C_1–C_{20})$ alkylenos, 2–20 membered heteroalkyldiyls and 2–20 membered heteroalkylenos, especially ($C_1$–$C_{20}$) alkynos, ($C_1$–$C_{20}$) alkenos, 2–20 membered heteroalkynos and 2–20 membered heteroalkenos. A particularly preferred linker L' is —C|C—$CH_2$—, where the terminal sp carbon is covalently attached to the nucleobase of NUC and the terminal methylene (sp$^3$) carbon is covalently attached to $R^{41}$ in the compounds of structural formula (II), or to $F_x$ of compound 35.

Additional preferred linkers L' for covalently conjugating the dyes or of the invention to the nucleobase of NUC include propargylethoxy groups according to structural formula —C|C—$CH_2$—O—$CH_2$—$CH_2$—$NR^{47}$—$R^{48}$—, wherein $R^{47}$ is hydrogen or ($C_1$–$C_6$) alkyl and $R^{48}$ is selected from the group consisting of —C(O)—($CH_2$)$_r$—, —C(O)—$CHR^{49}$—, —C(O)—C|C—$CH_2$— and —C(O)—φ—($CH_2$)$_4$—, where each r is independently an integer from 1 to 5 and φ represents a $C_6$ aryldiyl or a 6-membered heteroaryldiyl, preferably phena-1,4-diyl

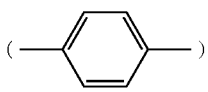

and $R^{49}$ is hydrogen, ($C_1$–$C_6$) alkyl or an amino acid side chain (including side chains of both gene-encoded and non-encoded amino acids). With these linkers L', the terminal sp carbon is attached to the nucleobase of NIC and the other terminal group is attached to $R^{41}$ in the compounds of structural formula (II), or to $F_x$ of compound 35.

In a preferred embodiment, the labeled nucleosides/tide and/or nucleoside/tide analogs according to structural formula (II) are labeled enzymatically-incorporable nucleotides, labeled enzymatically extendible nucleotides or labeled terminators.

In another preferred embodiment, the labeled nucleosides/tides and nucleoside/tide analogs are those obtained from Scheme (III) in which compound 36 is a compound according to structural formula (I.A), (I.D), (I.E), (I.F), (I.G), (I.H), (I.I), (I.J) or (I.K), or any of the preferred embodiments thereof and/or compound 35 is a compound according to structural formula (IIa):

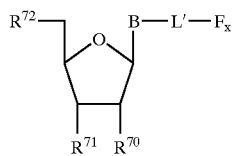

(IIa)

wherein:

B is a nucleobase;

$F_x$ is a complementary finctional group as previously described;

L' is a linker a previously described;

$R^{70}$ and $R^{71}$, when taken alone, are each independently selected from the group consisting of hydrogen, hydroxyl and a moiety which blocks polymerase-mediated template-directed polymerization, or when taken together form a bond such that the illustrated sugar is 2',3'-didehydroribose; and $R^{72}$ is selected from the group consisting of hydroxyl, a phosphate ester having the formula

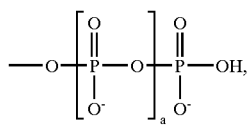

where a is an integer from 0 to 2, and a phosphate ester analog. Typically, $F_x$ is an amino group of the formula —$NHR^{51}$, where $R^{51}$ is hydrogen or ($C_1$–$C_6$)alkyl, but can be any of the nucleophilic or electrophilic groups listed in TABLE 2, supra.

In a prefefred embodiment of structural formula (IIa), B is a normal nucleobase or a common analog thereof, a 7-deazapurine, a purine or a pyrimidine and L' is one of its previously described preferred embodiments. In a particularly preferred embodiment, B is a nucleobase selected from the group consisting of adenine, 7-deaza-adenine, cytosine, guanine, 7-deaza-guanine, thymine and uracil. When the preferred nucleobase B is a purine or a 7-deaza-purine, the pentose moiety is attached to the $N^9$-position of the nucleobase, and when the preferred B is a pyrimidine, the pentose moiety is attached to the $N^1$-position of the nucleobase. Linker L' is attached to nucleobase B as previously described.

In structural formula (IIa), when both $R^{70}$ and $R^{71}$ are hydroxyl, the resultant compounds produced in Scheme (III) are labeled ribonucleoside/tides. When $R^{70}$ is hydrogen and $R^{71}$ is hydroxyl, the resultant compounds are labeled 2'-deoxyribonucleoside/tides. When $R^{70}$ and $R^{71}$ are each hydrogen, the resultant compounds are 2',3'-dideoxyribonucleoside/tides Labeled 2',3'-dideoxyribonucleoside-5'-triphosphates (ddNT[]s) find particular use as terminators in Sanger-type DNA sequencing methods utilizing fluorescent detection. Labeled 2'-deoxyribonucleoside-5'-triphosphates (dNTPs) find particular use as means for labeling DNA polymerase extension products, e.g., in the polymerase chain reaction or nick-translation. Labeled ribonucleoside-5'-triphosphates (NTPs) find particular use as means for labeling RNA polymerase extension products.

Referring to Scheme (III), supra, the synthesis of alkynylamino-derivatized compounds 35 useful for conjugating the dyes of the invention to nucleosides/tides and/or nucloside/tide analogs is taught in EP 87305844.0 and Hobbs et al., 1989, J. Org. Chem. 54:3420. Briefly, the alkynylamino-derivatized nucleotides are formed by placing the appropriate halonucleoside (usually 5-iodopyrimidine and 7-iodo-7-deazapurine dideoxynucleosides as taught by Hobbs et al., 1989, supra) and Cu(I) in a flask, flushing the flask with argon to remove air and adding dry DMF followed by addition of an alkynylamine, triethylamine and Pd(0). The reaction mixture is stirred for several hours, or until thin layer chromatography indicates consumption of the halonucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional ethanol/methylene chloride. The combined filtrates can be concentrated and purified by flash-chromatography on silica gel using a methanol-methylene chloride gradient. The corresponding nucleoside mono-, di- and triphosphates are obtained by standard techniques (see, e.g., the methods described in U.S. Pat. No. 5,821,356, U.S. Pat. No. 5,770,716 and U.S. application Ser. No. 08/833,854 filed Apr. 10, 1997, discussed supra). Methods for synthesizing compound 35 modified with a propargylethoxyamido linker L' can also be found in these patents and application.

Additional synthesis procedures suitable for use in synthesizing compounds according to structural formula (II) are described, for example, in Gibson et al., 1987, Nucl. Acids Res. 15:6455–6467; Gebeyehu et al., 1987, Nucl. Acids Res. 15:4513–4535; Haralambidis et al., 1987, Nucl. Acids Res. 15:4856–4876; Nelson et al., 1986, Nucleosides and Nucleotides. 5(3):233–241; Bergstrom et al., 1989, J. Am. Chem. Soc. 111:374–375; U.S. Pat. No. 4,855,225, U.S. Pat. No. 5,231,191 and U.S. Pat. No. 5,449,767, the disclosures of which are incorporated herein by reference. Any of these methods can be routinely adapted or modified as necessary to synthesize thefull range of labeled nucleosides/tides and nucleosideltide analogs described herein.

4.5.2 Phosphoramidite Reagents

Another preferred class of reagents of the invention comprises phosphoramidite compounds which incorporate the mobility-modifying cyanine dyes of the invention. Such phosphoramidite reagents are particularly useful for the automated chemical synthesis of polynucleotides labeled with the dyes of the invention. Such phosphoramidite reagents, when reacted with a hydroxyl group, such as a 5'-hydroxyl group of a nucleoside/tide or polynucleotide, form a phosphite ester linkage which, in turn, is oxidized to yield a phosphate ester linkage. For a detailed discussion of phosphoramidite chemistry see, e.g., Caruthers et al., U.S. Patent Nos. 4,458,066 and 4,415,732 and Gait, 1985, *Oligonucleotide Synthesis: A Practical Approach*, IRL Press, Oxford, England. The phosphoramidite reagents can be nucleosidic or non-nucleosidic, as will be described in more detail, below.

4.5.2.1 Non-Nucleosidic Phosphoramidite Reagents

In one aspect, the phosphoramidite reagents of the invention are non-nucleosidic compounds according to structural formula (III):

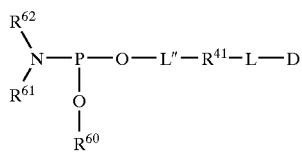

(III)

wherein:

N, O and P represent nitrogen, oxygen and phosphorous, respectively;

L" represents a bond or a linker as will be described more fully below;

R"represents a bond or a linkage as previously defined for structural formula (II);

L represents a linker as previously defined for structural formula (I);

D represents a dye chromophore according to the invention or a protected derivative thereof;

$R^{60}$ is a phosphite ester protecting group;

$R^{61}$, when taken alone, is selected from the group consisting of $(C_1-C_6)$ alkyl, $(C_1-C_6)$ alkanyl, $(C_2-C_6)$ alkenyl, $(C_2-C_6)$ alkynyl, $(C_3-C_{10})$ cycloalkyl, $(C_5-C_{20})$ aryl and $(C_6-C_{26})$ arylalkyl, or when taken together with $R^{62}$ forms a straight-chain or branched $(C_2-C_{10})$ alkyleno or a straight-chain or branched 2–10 membered heteroalkyleno; and $R^{62}$, when taken alone, is selected from the group consisting of $(C_1-C_6)$ alkyl, $(C_1-C_6)$ alkanyl, $(C_2-C_6)$ alkenyl, $(C_2-C_6)$ alkynyl, $(C_{3-C10})$ cycloalkyl, $(C_5-C20)$ aryl and $(C_6-C_{26})$ arylalkyl, or when taken together with $R^{61}$ forms a straight-chain or branched $(C_2-C_{10})$ alkyleno or a straight-chain or branched 2–10 membered heteroalkyleno.

According to structural formula (III), $R^{60}$ is a phosphite ester protecting group which prevents unwanted extension of the polynucleotide to which the phosphoramidite is attached. Generally, $R^{60}$ is stable to polynucleotide synthesis conditions yet is able to be removed from a synthetic polynucleotide product with a reagent that does not adversely affect the integrity of the polynucleotide or the dye. A variety of phosphite ester groups having these characteristics are well-known in the art. Preferably, $R^{60}$ is methyl, β-cyanoethyl or 4nitrophenylethyl.

While not depicted in structural formula (III), dye chromophore D is attached to linker L at the heteroaromatic imminium nitrogen, as depicted in structural formula (I). In some insances, D may contain functional groups that require protection, either during the synthesis of the phosphorarnidite reagent or during its subsequent use to label molecules such as polynucletodies. The protecting group(s) used will depend upon the nature of the functional groups, and will be apparent to those having skill in the art. Generally, the protecting groups used should be stable under the acidic conditions commonly employed in polynucleotide synthesis to remove 5'-hydroxyl protecting groups (e.g., dimethoxytrityl) and labile under the basic conditions used to deprotect and/or cleave synthetic polynucleotides from resins. Guidance for selecting appropriate protecting groups can be found, for examnple, in Greene & Wuts, 1991, *Protective Groups in Organic Synthesis*, John Wiley & Sons, Inc., New York.

It should be noted, however, that cyanine dyes are generally not completely stable under the basic conditions typically used to deprotect and/or cleave synthetic polynucleotides from synthesis resins. Thus, any base-labile protecting groups used should be removable under relatively mild basic conditions (e.g., exposure to ammonium hydroxide or 0.05M potassium carbonate in methanol for 2 hrs. or less at a temperature of 55° C. or less or, alternatively, exposure to a 50:50 mixture of anmnonium hydroxide and 40% aqueous methylamine for 90 min. at room temperature or 5 min. 65° C.). Of course, any exocyclic amines or other finctionalities on the nucleoside phosphoramidites used to synthesize the polynucleotide that will be labeled with the compounds according to structural formula (III) should likewise be protected with such mild base-labile protecting groups. Suitable groups are known in the art, and include, for example, isobutyryl, phenoxyacetyl, 4-isopropyl-phenoxyacetyl and acetyl. Other protecting groups having these properties will be apparent to those having skill in the art. Polynucleotide synthesis reagents and supports having appropriate base-labile linkage and protecting groups, as well as reagents for their removal and/or cleavage are comnnercially available (see, e.g., products catalog of Glen Research, Sterling, Va. 20164).

The phosphoramidite portion of the molecule is linked to dye chromophore D via linkage —L"—R"—L—. As will be discussed in more detail below, the linkage —L"—$R^{41}$—

L"— can take a variety of forms, but generally must be a linkage that is (i) stable to DNA synthesis conditions; (ii) does not substantially interfere with oligonucleotide-target hybridization; and (iii) does not quench the fluorescence of the dye to which it is attached, e.g., U.S. Pat. Nos. 5,231,191, 5,258,538, 4,757,141 and 5,212,304.

The composition of —L"—$R^{41}$—L— is in part dictated by the methods used to synthesize the phosphoramidite reagents. For example, appropriately protected mobility-modifying dyes according to structural formula (I) in which linking group LG is a hydroxyl can be conveniently phosphitylated using standard methods and reagents to yield phosphoramidites according to structural formula (III). In these instances, L is any of the previously-described linkers that is compatible with polynucleotide synthesis conditions and —L"—$R^{41}$ constitutes a bond.

Alternatively, dyes of formula (I) in which linking moiety LG is reactive group $R_x$ can be conveniently "converted" to include a hydroxyl by reacting the dye with an "adapter molecule" which includes a hydroxyl and a functional group complementary to reactive group $R_x$, such as any of the previously-described complementary functional groups $F_x$ (see, e.g., TABLE 2, supra.). Analogous to the compounds of structural formula (II), in the compounds of structural formula (III), the reaction between reactive group $R_x$ and functional group $F_x$ form linkage $R^{41}$. The oxygen intervening the phosphorous atom and linker L" is contributed by the adapter molecule. Thus, adapter molecules useful for providing a hydroxyl group suitable for phosphitylation are generally compounds having the structure $R^{63}$—O—L"—$F_x$, where $R^{63}$ is hydrogen or a hydroxyl protecting group, preferably an acid-labile hydroxyl protecting group as described in more detail, infra. Preferably, $F_x$ is an amine of the formula —$NHR^{56}$, where $R^{56}$ is hydrogen or ($C_1$–$C_6$) alkyl and reactive group $R_x$ of the dye is a carboxyl or carboxylate, or an activated ester thereof, such that $R^{41}$ in the compounds of structural formula (III) is an amide or substituted amide having the formula —$NR^{56}$—C(O)—, where $R_{56}$ is as previously described.

Linker L" is analogous to linker L and therefore may be flexible or rigid, long or short, or hydrophobic or hydrophilic, depending upon the particular application. Linker L" can be any of the previously described linkers L or L' that are stable to polynucleotide synthesis conditions. Selection of an appropriate linker will depend upon the particular application, and will be apparent to those having skill in the art. For example, linker L" may be a ($C_1$–$C_{30}$) alkyldiyl, 1–30 membered heteroalkyldiyl, ($C_5$–$C_{14}$) aryldiyl, ($C_5$–$C_{14}$) arylaryldiyl, ($C_6$–$C_{26}$) arylalkyldiyl, 6–26 membered arylheteroalkyldiyl, 5–14 membered heteroaryldiyl, 5–14 membered heteroaryl-heteroaryldiyl, 6–26 membered heteroarylalkyldiyl or 6–26 membered heteroaryl-heteroalkyldiyl. Preferred linkers L" include alkylenos and heteroalkylenos, especially ($C_1$–$C_{30}$) alkanos and linear polyethylene oxides having the formula —$(CH_2CH_2O)_u$—$CH_2CH_2$—, where u is an integer ranging from 1 to 30, preferably from 2 to 10, and more preferably from 2 to 6.

Those of skill in the art will appreciate that compounds according to structural formula (III) are particularly useful for labeling the 5'-terminus of synthetic polynucleotides with the mobility-modifying dyes of the invention. However, in many instances it may be desirable to label the 3'-terminus and/or to provide internal labels intervening the nucleosides of a synthetic polynucleotide. In these instances, linker L" (or, alternatively linker L) should provide a hydroxyl group for subsequent synthesis. The hydroxyl for subsequent synthesis is protected during the phosphitylation reaction with an acid-labile protecting group, such as those typically used to protect the primary 5'-hydroxyl of the 2'-deoxyribonucleoside phosphorarnidites commonly employed in polynucleotide synthesis, as described in more detail, infra. Preferred linkers L" (or alternatively L) according to this aspect of the invention include branched ($C_1$–$C_{30}$) alkyls substituted with a hydroxyl. Particularly preferred phosphoramidite reagents according to this aspect of the invention are compounds according to structural formula (III.A):

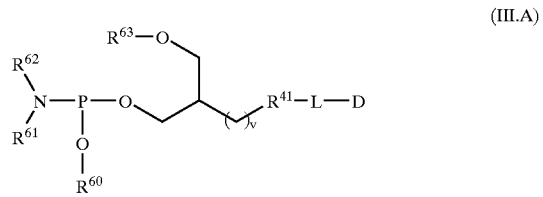

(III.A)

wherein:

N, P and O represent nitrogen, phosphorous and oxygen, respectively;

$R^{41}$, L, D, $R^{60}$, $R^{61}$ and $R^{62}$ are as previously defined for structural formula (III);

$R^{63}$ is hydrogen or an acid-labile hydroxyl protecting group; and v is an integer from 1 to 30, preferably from 1 to 5.

In the compounds of structural formula (III.A), $R^{63}$ is hydrogen or an acid labile hydroxyl protecting group. Preferably, $R^{63}$ is a triphenylmethyl (trityl) group or a derivative thereof that is substituted with one or more of the same or different electron- donating substituents. As used herein, the term "electron-donating" refers to the tendency of a substituent to release valence electrons to neighboring atoms in the molecule of which it is a part, i.e., it is electropositive with respect to neighboring atoms. Preferably, electron-donating substituents include amnino, ($C_1$–$C_6$) alkyl, ($C_1$–$C_8$) aryl, ($C_1$–$C_6$) alkoxy, and the like. More preferably, the electrondonating substituent(s) are methoxy. Exemplary acid-labile trityl derivatives include 4,4'-dimethoxytrityl, i.e. bis(p-anisyl)phenylmethyl, monomethoxytrityl, α-naphthyldiphenylmethyl, tri(p-methoxyphenyl)methyl, and the like. Attachment and cleavage conditions for these and other trityls can be found in Greene and Wuts, 1991, *Protective Groups in Organic Synthesis*, $2^{nd}$ Ed., John Wiley & Sons, New York, and Gait, 1985, *Oligonucleotide Synthesis: A Practical Approach*, IRL Press, Oxford, England.

In a preferred embodiment of the invention, in the compounds of structural formulae (III) and (III.A), $R^{61}$ and $R^{62}$ are taken alone and are each independently a branched or straight-chain ($C_1$–$C_6$) alkyl, more preferably a branched or straight-chain ($C_1$–$C_6$) alkanyl. In a particularly preferred embodiment, $R^{61}$ and $R^{62}$ are each independently propan-2-yl (isopropyl), butan-2-yl, butan-3-yl, 2-methyl-propan-1-yl (iso- butyl) or 2-methyl-propan-2-yl (t-butyl).

In another preferred embodiment, in the compound of structural formulae (III) and (III.A), $R^{61}$ and $R^{62}$ are taken together and form a straight chain ($C_2$–$C_5$) alkano bridge or a ($C_2$–$C_{10}$) branched alkano bridge in which the principle chain or bridge contains from 2 to 5 carbon atoms. In an alternative preferred embodiment, $R^{61}$ and $R^{62}$, when taken together with the nitrogen atom, form a 5–8 membered heteroalkyl, optionally containing one or more additional heteroatoms selected from the group consisting of nitrogen, oxygen and sulfur. In a particularly preferred embodiment, $R^{61}$ and $R^{62}$, when taken together with the nitrogen atom, form a morpholino group.

In yet another preferred embodiment, in the compounds of structural formulae (III) and (III.A), D is a chromophore derived from structure (I), (I.A), (I.D), (I.E), (I.F) or (I.G), or any of their preferred embodiments.

Phosphoramidite reagents according to structural formulae (III) and (III.A) can be synthesized by a variety of known methods. Hydroxyls and other reactive functionalities of the dye chromophore are protected with protecting groups that can be removed under the desired conditions, commonly with a DNA synthesis deprotection agent, such as ammonia, ethanolamine, iodine, methylamine/ammonium hydroxide mixtures, and mixtures of t-butylamine/water/methanol (1:2:1) (see, e.g., U.S. Pat. No. 5,231,191). Preferred protecting groups include esters of benzoic acid or pivalic acid. Most preferably, the protecting groups are removable under mildly basic conditions, as described supra.

Any hydroxyl groups on L, L', or L" for subsequent synthesis are protected with an acid-labile protecting group, preferably 4,4'-dimethoxytrityl, prior to phosphitylation. If linking moiety LG of the protected dye is a hydroxyl, it can be phosphitylated according to standard methods. If the linking moiety contains reactive group $R_x$, such as, for example, a carboxyl group, it is activated, e.g., with carbodiimide, and reacted with an adapter molecule, e.g., ethanolamine, hexanol amine, or the like, in N,N-dimethylformnamide (DMF), or another like aprotic solvent to yield a protected dye with a hydroxyl functionality. The hydroxyl is then reacted with a phosphitylating agent using standard procedures, e.g., di-(N,N-diisopropylamino) methoxyphosphine in acetonitrile containing catalytic amounts of tetrazole diisopropylamine, to yield the phosphoramidite (see, e.g., U.S. Pat. No. 5,231,191).

4.5.2.2 Nucleosidic Phosphoramidite Reagents

In a second preferred embodiment, the phosphoramidite reagents of the invention are 2'-deoxyribonucleoside-5'-phosphoramidites according to structural formula (IV):

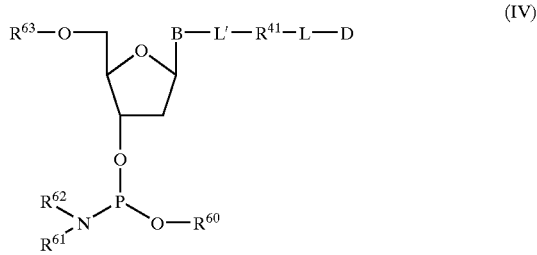

(IV)

wherein:

B is a nucleobase or a protected derivative thereof;

L', $R^{41}$, L, D, $R^{60}$, $R^{61}$ and $R^{62}$ are as previously described for structural formula (III); and $R^{63}$ is as previously described for structural formula (III.A).

When B is a purine or 7-deazapurine, the illustrated 2'-deoxyribose moiety is attached to the $N^9$-position of the purine or deazapurine. Alternatively, when B is a pyrimidine, the 2'-deoxyribose moiety is attached at the $N^1$-position of the pyrimidine. B and D are linked through linkage —L'—$R^{41}$—L—, typically formed by the reaction of complementary reactive and functional groups, as described in detail above. If B is a purine, L' is attached to the C-8 position of the purine, while if B is a 7-deazapurine, L' is attached to the C-7 position of the 7-deazapurine. If B is a pyrimidine, L' is attached to the C-5 position of the pyrimidine. The site of attachment of L' to other nucleobases will be apparent to those of skill in the art.

As will be recognized by those of skill in the art, the exocyclic amines and other functionalities of nucleobase B may require protection during the synthesis of the phosphorarnidite reagent and/or during its subsequent use to synthesize labeled polynucleotides. The particular protecting group (s) selected will depend on the identity of the nucleobase or nucleobase analog, and will be apparent to those of skill in the art. Generally, protecting groups commonly used in the art of nucleic acid synthesis are used. For example, the exocyclic amines of adenine and cytosine can be protected with benzoyl (Bz) and the exocyclic amine of guanine can be protected with dimethylformarnide (dmf) or isobutyryl (iBu) using conventional N-acylating procedures. The $O^6$ amide oxygen of guanine, as well as the $O^4$ amide oxygen of thymine and/or uracil can also be optionally protected with, for example, phosphinothioyl, 2-nitrophenyl or substituted ethyl groups (e.g., cyanoethyl) using conventional techniques (see, e.g., Deskalov et al., 1981, Bull. Chem. Soc. Japan 54:3076; Jones et al., 1981, Tetrahedron Lett. 22:4755; Gaffriey & Jones, 1982, Tetrahedron Lett. 23:2257; Trichtinger et al., 1983, Tetrahedron Lett. 24:211; Himmelsbach et al., 1981, Tetrahedron Lett. 40:59).

Preferably, the nucleobase is protected with groups that are readily removed under mild basic conditions, as previously described. Protecting groups removable under such mild basic conditions are well-known. For example, polynucleotides synthesized with $dA^{Bz}$, $dC^{Bz}$, $dG^{iBu}$ and dT phosphoramidities (and their corresponding resins) can be cleaved and deprotected in 90 minutes or less using a 50:50 mixture of ammonium hydroxide and 40% aqueous methylamino (Aldrich M2, 775-1), depending upon the temperature (5 minutes at 65° C.; 90 minutes at 25° C.). Polynucleotides synthesized with $dA^{iBz}$, $dA^{Pac}$, $dC^{Ac}$, $dG^{iPr-Pac}$ and dT phosphoramidites (and their corresponding resins) can be cleaved and deprotected in 2 hours at room temperature with ammonium hydroxide or 0.05M potassium carbonate in methanol. Thus, preferred exocyclic amine protecting groups for adenine are benzoyl (Bz), isobutyryl (iBu) and phenoxyacetyl (Pac). Preferred exocyclic amine protecting groups for cytosine are Bz and acetyl (Ac). Preferred exocyclic amine protecting groups for guanine are iBu and 4-isopropyl-phenoxyacetyl (iPr-Pac). The actual protecting group selected for a particular nucleobase will depend upon the protection of the other nucleobase and will be apparent to those of skill in the art.

Preferred compounds according to structural formula (IV) include those compounds in which L" is one of the previously described preferred embodiments of linker L' and L, D, $R^{60}$, $R^{61}$, $R^{62}$, and/or $R^{63}$ are their respective preferred embodiments previously described in connection with structural formula (III) or (III.A).

The 2'-deoxyribonucleoside phosphoramidites according to structural formula (IV) can be synthesized using standard methods, as is illustrated in Scheme (IV), below, with a propargyl linker L', carboxyl reactive groups $R_x$ and primary amino complementary functional groups $F_x$.

Scheme (IV)

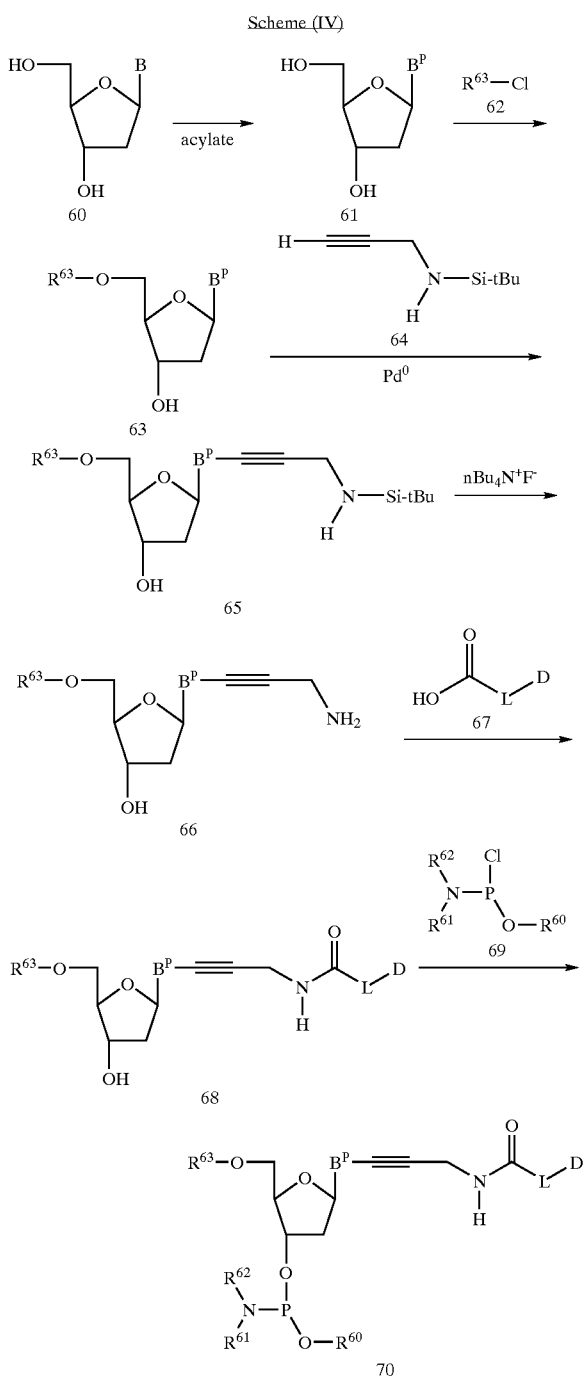

In Scheme (IV), $R^{60}$, $R^{61}$, $R^{62}$, $R^{63}$, B, L and D are as previously defined for structural formula (IV) and $B^P$ is a protected nucleobase or nucleobase analog.

According to Scheme (IV), nucleoside 60 is Nacylated to protect any exocyclic amines using standard procedures, yielding protected nucleoside 61. Protected nucleoside 61 is reacted with chloride 62 (e.g., 4,4'-dimethoxytritylchloride) to yield 5'-protected nucleoside 63. Compound 63 is reacted with compound 64 in the presence of palladium(0), yielding protected propargyl linker-modified nucleoside 65. The t-butylsilyl protecting group of the propargylarnino linker is selectively removed with tetrabutyl ammonium fluoride ($nBu_4N^+F^-$) to yield protected nucleoside 66. Next, the protected nucleoside 66 is labeled with the dye by reacting it with dye 67 under conditions in which the reactive group of the dye react with the complementary functional group of the protected nucleoside to form a covalent linkage. In the specific example illustrated in Scheme (IV), the reactive carboxyl of dye 67 is conveniently converted to a reactive ester, e.g., a NHS ester, with dicyclohexyl carbodiimide and N-hydroxysuccinirnide. The activated NHS ester then reacts with compound 66 to yield dye-labeled nucleoside 68, which is phosphitylated with compound 69 to yield phosphoramidite 70. Any reactive groups on dye chromophore D or linker L can be protected as previously described. Methods of synthesizing compounds according to structural formula (IV) including linkers L' and linkages $R_{41}$ other than those depicted in Scheme (IV) can be synthesized by routine modification of the above method, by resort to other conventional synthetic methods (see, e.g., Meyer, "Incorporation of Modified Bases into Oligonucleotides," *In: Methods in Molecular Biology Volume 26: Protocolsfor Oligonucleotide Conjugates*, Chapter 2, Agarwal, Ed., 1994, Humana Press, Totowa, N.J., as well as the references cited therein), or by routine modification of the methods provided in connected with the compounds of structural formula (III).

Labeled 2'-deoxyribonucleoside-3'-phosphoramidites according to structural formula (IV) are particularly well suited for providing labels at the 3',5' and/or internal positions of chemically-synthesized polynucleotides.

4.5.2.3 Polynucleotide Reagents

Yet another preferred class of reagents of the present invention comprise polynucleotides or polynucleotide analogs labeled with the mobility-modifying cyanine dyes of the invention. Such labeled polynucleotides or analogs are useful in a number of important contexts, including as DNA sequencing primers, PCR primers, oligonucleotide hybridization probes, oligonucleotide ligation probes, and the like.

In one preferred embodiment, the labeled polynucleotides or polynucleotide analogs of the present invention include multiple dyes positioned so that fluorescence energy transfer takes place there between. Such.multi-dye energy-transfer polynucleotides find application as spectrally-tunable sequencing primers as described, for example, in Ju et aL, 1995, Proc. Natl. Acad. Sci. USA 92:4347–435 1, and as hybridization probes as described, for example, in Lee et al., 1993, Nucl. Acids Res. 21:3761–3766.

Labeled polynucleotides and/or polynucleotide analogs may be synthesized either enzymatically, e.g., using a DNA polymerase or ligase (see, e.g., Stryer, 1981, *Biochemistry*, Chapter 24, W. H. Freeman and Company), or by chemical synthesis, e.g., by the phosphoramidite method, the phosphite-triester method, and the like (see, e.g., Gait, 1990, *Oligonucleotide Synthesis*, IRL Press, Oxford, England). Labels may be introduced during enzymatic synthesis utilizing the labeled enzymatically-incorporable nucleoside/tides and/or nucleoside/tide analogs described above, or during chemical synthesis using the labeled non-nucleosidic or nucleosidic phosphoramidite reagents described above. Alternatively, the labels may be introduced subsequent to synthesis via conventional conjugation reactions.

Generally, if the labeled polynucleotide is made using enzymatic synthesis, the following procedure may be used. A target DNA is denatured and an oligonucleotide primer is annealed to the template DNA. A mixture of enzymatically-incorporable nucleoside/tides or nucleosideltide analogs capable of supporting continuous template- directed enzymatic extension of the primed target (e.g., a mixture including dGTP, dATP, dCTP and dTTP or dUT?) is added to the primed target. At least a fraction of the nucleoside/tides or nucleosideltide analogs is labeled with a dye compound of the invention or are labeled terminators, as described above. Next, a polymerase enzyme is added to the mixture under conditions where the polymerase enzyme is active. A labeled polynucleotide is formed by the incorporation of the labeled nucleosideltides or nucleoside/tide analogs or terminators during polymerase-mediated strand synthesis. In an alternative enzymatic synthesis method, two primers are used instead of one: one complementary to the (+) strand of the target and another complementary to the (-) strand of the target, the polymerase is a thermostable polymerase and the reaction temperature is cycled between a denaturation temperature and an extension temperature, thereby exponentially synthesizing a labeled complement to the target sequence by PCR, (see, e.g., PCR *Protocols,* 1990, Innis et al Eds., Academic Press).

Labeled polynucleotides or polynucleotide analogs may also be chemically synthesized using the phosphoramidite or other solution or solid-phase methods. Detailed descriptions of the chemistry used to form polynucleotides by the phosphoramidite method are provided elsewhere (see, e.g., Caruthers et aL, U.S. Pat. Nos. 4,458,066 and 4,415,732; Caruthers et al., 1982, Genetic Engineering 4:1–17; *Users Manual Model* 392 *and* 394 *Polynucleotide Synthesizers,* 1990, pages 6-1 through 6-22, Applied Biosystems, Part No. 901237).

The phosphoramidite method of polynucleotide synthesis is the preferred method because of its efficient and rapid coupling on solid support. The synthesis is performed with the growing polynucleotide chain attached to a solid support, such that excess reagents, which are in the liquid phase, can be easily removed by decanting, filtration, etc., thereby eliminating the need for purification steps between synthesis cycles.

The following briefly describes the steps of a typical polynucleotide synthesis cycle using the phosphoramidite method. First, a solid support including a protected nucleoside monomer is treated with acid, e.g., trichloroacetic acid, to remove the 5'-hydroxyl protecting group, freeing the hydroxyl for a subsequent coupling reaction. An activated intermediate is then formed by simultaneously adding a protected nucleoside phosphorarnidite monomer and a weak acid, e.g., tetrazole, to the reaction. The weak acid protonates the nitrogen of the phosphoramidite forming a reactive intermediate.

Nucleoside addition is complete within 30 s. Next, a capping step is performed which terminates any polynucleotide chains that did not undergo nucleoside addition. Capping is preferably done with acetic anhydride and 1-methylimidazole. The intemucleotide linkage is then converted from the phosphite to the more stable phosphotriester by oxidation using iodine as the preferred oxidizing agent and water as the oxygen donor. After oxidation, the hydroxyl protecting group is removed with a protic acid, erg., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and any protecting groups on the dyes are removed by treating the polynucleotide solution in base at an elevated temperature, e.g., 55° C. Preferably the various protecting groups removed using the mildly basic conditions previously described.

Any of the nucleoside phosphoramidite monomers may be dye-labeled phosphoramidites as described above. If the 5'-terminal position of the nucleotide is labeled, a labeled non-nucleotidic phosphoramidite of the invention may be used during the final condensation step. If the 3'-terminal position or one or more internal position of the oligonucleotide are labeled, a labeled nucleosidic phospborarnidite of the invention may be used during any of the condensation steps or, alternatively, using the non-nucleosidic phosphoramidites of the invention.

Subsequent to synthesis, the polynucleotide may be labeled at a number of positions, including the 5'-terminus, (see, e.g., *Oligonucleotides and Analogs*, Eckstein 1990, Ed., Chapter 8, IRL Press; Orgel et al.,1983, *Nucleic Acids Research* 11(18):6513; U.S. Pat. No. 5,118,800), the phosphodiester backbone,(see, e.g., Orgel et al., supra, at Chapter 9) or the 3'-terniminus (see e.g., Nelson, 1992, *Nucleic Acids Research* 20(23):6253–6259; U.S. Pat. No. 5,401,837 U.S. Pat. No. 5,141,813.) For a through review of oligonucleotide labeling procedures see R. Haugland in *Excited States of Biopolymers*, Steiner Ed., Plenum Press, NY (1983).

In one preferred post-synthesis chemical labeling method an oligonucleotide is labeled as follows. A dye including a carboxy linking group is converted to the N-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5 % HCl, dried over magnesium sulfate, filtered, and concentrated to a solid which is resuspended in DMSO. The DMSO dye stock is then added in excess (10–20 =) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g. 0.1 molar triethylamine acetate (TEAA). The fraction containing the crude labeled oligonucleotide is frther purified by reverse phase HPLC employing gradient elution.

4.6 Kits

In a final aspect, the invention comprises kits comprising the mobility- modifing cyanine dyes and/or labeled conjugate of the invention. In one embodiment, the kits are useful for conjugating the mobility-modifying dyes of the invention to other molecules or substances. Such kits generally comprise a mobility-modifed dye of the invention including an optional linking moiety and buffers, solvents, etc. suitable for conjugating the dye to another molecule or substance.

In another embodiment, the kits are useful for labeling enzymatically synthesized polynucleotides with the mobility-modifing dyes of the invention. Such kits generally comprise a labeled enzymatically-incorporable nucleoside/tide or nucleoside/tide analog according to the invention, a mixture of enzymatically-incorporable nucleoside/tides or nucleoside/tide analogs capable of supporting continuous primer extension and a polymerizing enzyme. Preferably, the labeled enzymatically-incorporable nucleoside/tide or nucleoside/tide analog is a compound according to structural formula (II or II.A), most preferably a labeled terminator. Preferred polymerizing enzymes are therrnostable polymerases such as AMPLITAQ® DNA polymerase FA (PE Biosystems, Foster City, Calif.).

In a final embodiment, the kits are useful for labeling synthetic polynucleotides with the mobility-modifying dyes of the invention. Such kits generally comprise a labeled phosphoramidite reagent according to the invention and synthesis reagents and/or solid supports optionally for carrying out oligonucleotide synthesis.

4.7 Methods Utilizine the Dyes and Reagents of the Invention

The mobility-modifying dyes of the invention and conjugatesincorporating the dyes are well suited to any method utilizing fluorescent detection, particularly aqueous applications and methods requiring the simultaneous detection of multiple spatially-overlapping analytes. The various dyes and conjugates of the invention are particularly well suited for identifying classes of polynucleotides that have been subjected to a biochemical separation procedure, such as electrophoresis, or that have been distributed among locations in a spatially-addressable hybridization array.

In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphism detection (AmpFLP) is based on amplified fragment length polymorphisms, i.e., restriction fragment length polymorphisms that are amplified by PCRF These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

In another such fragment analysis method known as nick translation, a reaction is used to replace unlabeled nucleotides in a double-stranded (ds) DNA molecule with labeled nucleotides. Free 3'-hydroxyl groups are created within the dsDNA by "nicks" caused by treatment with deoxyribonuclease I (DNAase I). DNA polymerase I then catalyzes the addition of a labeled nucleotide to the 3'-hydroxyl terminus of the nick. At the same time, the 5' to 3'-exonuclease activity of this enzyme eliminates the nucleotide at the 5'-phosphoryl terminus of the nick. A new nucleotide with a free 3'-OH group is incorporated at the position of the original excised nucleotide, and the nick is shifted along by one nucleotide in the 3' direction. This 3' shift will result in the sequential addition of new labeled nucleotides into the dsDNA. The nicktranslated polynucleotide is then analyzed, for example, by using a separation process such as electrophoresis.

Another exemplary fragment analysis method is based on variable numbers of tandem repeats, or VNTRs. VNTRs are regions of double-stranded DNA that contain multiple adjacent copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments using a labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes and energy-transfer dye pairs of the invention by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a terminator that will not support continued DNA elongation. When proper proportions of dNTPs and a single terminator complementary to A, G, C or T are used, enzyme-catalyzed primer extension will be terminated in a fraction of the extension products at each site where the terminator is incorporated. If labeled primers or labeled terminators are used for each reaction, the sequence information can be detected by fluorescence after separation of the resultant primer extension products by high-resolution electrophoresis. In the chain termination method, dyes of the invention can be attached to either the sequencing primers or terminators. The dyes can be linked to a complementary functionality on the 5'-end of the primer, e.g. following the teaching in Fung et at, U.S. Pat. No. 4,757,141; on the base of a primer; or on the base of a terminator, e.g. via the alkynylamino or other linking groups described above. Concentration ranges for the various enzymes, primers, dNTPs and labeled terminators are those commonly employed in the art.

In each of the above fragment analysis methods, labeled extension products are preferably separated by electrophoretic procedures, e.g. *Gel Electrophoresis of Nucleic Acids: A Practical Approach,* 1981, Rickwood and Hames, Eds., IRL Press Limited, London; Osterman, 1984, *Methods of Protein and Nucleic Acid Research,* Vol. 1 Springer-Verlag, Berlin; or U.S. Pat. Nos. 5,374,527, 5,624,800 and/or 5,552,028. Preferably, the type of electrophoretic matrix is crosslinked or uncrosslinked polyacrylamide having a concentration (weight to volume) of between about 2–20 weight percent. I More preferably, the polyacrylamide concentration is between about 4–8 percent. Preferably, in the context of DNA sequencing, the electrophoresis matrix includes a denaturing agent, e.g., urea, formamide, and the like. Detailed procedures for constructing such matrices are given by Maniatis et aL, 1980, "Fractionation of Low Molecular Weight DNA and RNA in Polyacrylamide Gels Containing 98% Formamnide or 7 MUrea," *Methods in Enzymology* 65:299–305; Maniatis et al., 1975, "Chain Length Determination of Small Double- and Single-Stranded DNA Molecules by Polyacrylamide Gel Electrophoresis," *Biochemistry* 14:3787–3794; Maniatis et at., 1982, *Molecular Cloning: A Laboratory Manual*, Cold Spring Harbor Laboratory, New York, pgs. 179–185; and ABI PRISM™ 377 *DNA Sequencer User's Manual*, Rev. A, Jan. 1995, Chapter 2 (p/n 903433, The Perkin-Elmer Corporation, Foster City, Calif.). The optimal electrophoresis conditions, e.g., polymer concentration, pH, temperature, and concentration of denaturing agent, employed in a particular separation depend on many factors, including among others, the size range of the nucleic acids to be separated, their base compositions, whether they are single stranded or double stranded, and the nature of the classes for which information is sought by electrophoresis. Accordingly, application of the invention may require standard preliminary testing to optimize conditions for particular separations.

Subsequent to electrophoretic separation, the labeled extension products are detected by measuring the fluorescence emission from the labels. To perform such detection, the labeled products are illuminated by standard means, e.g. high intensity mercury vapor lamps, lasers, or the like. The illumination wavelength will depend upon the spectral properties of the particular label. Preferably, the illumination means is a laser having an illumination beam at a wavelength greater than 620 nm. As the mobility-modifying dyes of the invention generally absorb and emit light in the red region of the visible spectrum, more preferably, the illumination means is a 633 solid state HeNe laser at 638 nm. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like. Suitable exemplary electrophoresis detection systems are described elsewhere, e.g., U.S. Pat. Nos. 5,543,026; 5,274,240; 4,879,012; 5,091,652 and 4,811,218.

In preferred embodiments, the primer is unlabeled and the sequencing reaction includes, in addition to the polymerase and mixture of dNTPs, a mixture of four different terminators, one complementary to A, one complementary to G. one complementary to C and one complementary to T. Each of the different terminators is labeled with a different, spectrally resolvable dye. One of the terminators is labeled with a dye of the invention. As each of the labeled terminators fluoresces at a different wavelength, following separation based on size, the identity of the 3'-terminal nucleotide of each extension product is identified by the wavelength (or color) of the label. In particularly preferred embodiments, each of the different spectrally resolvable labels can be excited using a single light source. A set of such preferred labeled terminators is provided in the Examples section. Other sets will depend upon the excitation and emission spectral properties of the various labels, the described mobility shift, etc., and are readily obtained as described herein.

The invention having been described, the following examples are provided to illustrate, and not limit, the invention.

5. EXAMPLE: Compound Syntheses

This Example provides synthetic methods for certain exemplary compounds according to the invention.

5 5.1 Synthesis of (4(Hydroxymethyl)-I,3-Benzenedisulfonic Acid, Disodium Salt (Compound 42)

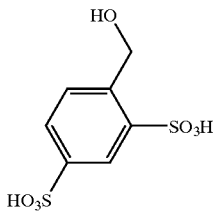

4-Formyl-1,3-benzenedisulfonic acid, disodium salt hydrate (41 from Aldrich Chemical Co.) (15 g) was dissolved in methanol (300 ml), followed by the slow addition of sodium borohydride (1.5 g). The solution was allowed to stir overnight. A white precipitate was filtered off, and the supemate was evaporated to dryness under vacuum yielding 41 as a white solid (1 5.5 g). NMR ($D_2O$) showed a singlet at 4.95 ppm corresponding to the benzylic methylene protons, and the absence of a singlet at 10.6 ppm corresponding to the aldehyde proton.

5.2 Synthesis of 4-(Bromomethyl)-1,3-Benzenedisulfonic Acid, Disodium Salt (Compound 43)

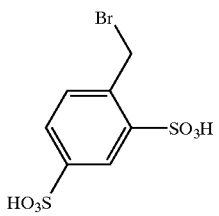

4-(hydroxymethyl)-1,3-benzenedisulfonic acid, disodium salt (42 from above) (8 g) and lithium bromide (3 g) were dissolved in 48% hydrobromic acid (95 g) and heated at 80° C. for 12 hr. The insoluble material was filtered, and the supernate was evaporated to dryness under vacuum. The resulting white solid was refluxed in 300 ml of acetone, and the insoluble material was filtered off. The acetone soluble fraction was evaporated to dryness under vacuum yielding a mixture of 42 and 43 as a tan solid (3.2 g). NMR ($D_2O$) showed a singlet at 4.95 ppm corresponding to the benzylic hydroxymethyl methylene protons from 42, and a singlet at 4.90 ppm corresponding to the benzylic bromomethyl methylene protons from 43. Integration of the proton signals showed the ratio of hydroxymethyl methylene protons from 42 to bromomethyl methylene protons from 43 to be 1:2.

5.3 Synthesis of N-Benzyl Alkylated 2,3,3-Trimethylbenz(e)indolenine (Compound 58)

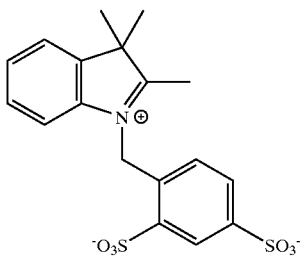

2,3,3-Trimethylbenz(e)indolenine 57 (Aldrich Chemical) (1 gram, 0.004785 moles) was mixed with 2 equivalents of 2,4-disulfo-benzyl bromide 43 (3.2 grams, 0.00957mole) in 3 mL of anhydrous nitrobenzene. After heating with stirring at 190° C. for 30 min under an Argon atmosphere, the reaction was cooled and ether added to precipitate crude 1-(2,4-disulfo-benzyl)-2,3,3-trimethylbenz(e)indolenine intermediate 58. Crude Compound 58 was recrystallized by suspension in methanol and precipitation by diethyl ether. Pure Compound 58 was then isolated by filtration and dried in a vacuum oven to give a tan solid (I gram, yield 39%).

5.4 Synthesis of N-Hexanoate Alkylated 2,3,3-Trimethylbenz(e)indolenine (Compound 59)

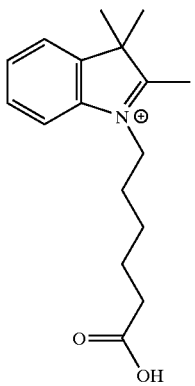

2,3,3-trimethylbenz(e)indolenine 57 (4 grams, 0.0159 moles) was mixed with 1 equivalent of 6-bromohexanoic acid 43 (3.1 grams, 0.0159 mole) in 8 mL of anhydrous nitrobenzene. The reaction was heated (120° C.) and stirred for 16 hrs under an argon atmosphere, the reaction was cooled and ether added to precipitate crude 1-(6-carboxyhexyl)2,3,3-trimethylbenz(e)indolenine 59. Crude Compound 59 was recrystallized by suspension in ethanol and precipitation by diethyl ether. Pure Compound 59 was then isolated by filtration and dried in a vacuum oven to give 5.02 grams as an off white solid (yield 71%).

5.5 Spnthesis of Cyanine Dye Intermediate Compound 20

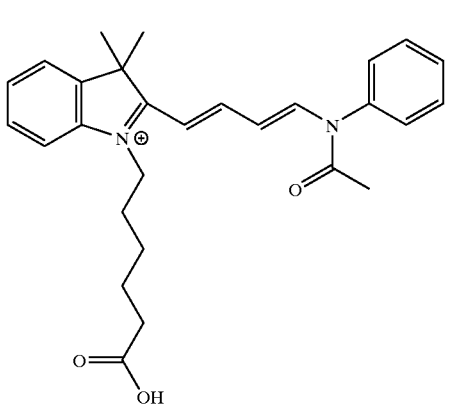

N-Hexyl-6 arboxylate modified indolenine intermediate 59 (1.2 gm, 0.00341 mole) was mixed with 1.2 equivalent of malonaldehyde bis(phenylimine) monohydrochloride (Aldrich Chemical) (1.05 gm, 0.0041 mole) in 15 mL of acetic anhydride After reflux for 1.5 hr, the reaction was cooled and diethyl ether added to precipitate the intermediate 20 in quantitative yield as a tan solid.

5.6 Synthesis of Mobility-Modifying Cyanine Dye MM-Cy5 (Compound 21)

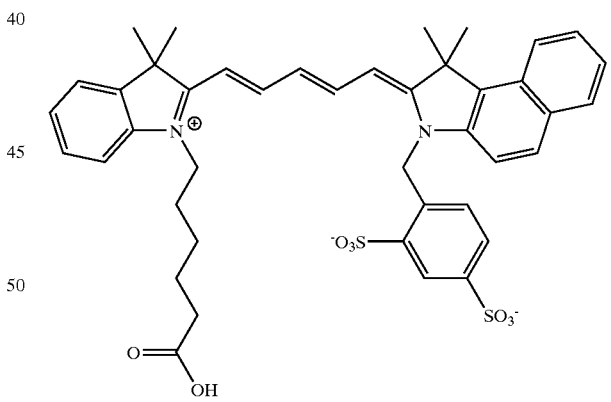

Intermediate 20 (100 mg, 0.000174 mole) was mixed with one equivalent of 1-(2,4-disulfo-benzyl)-2,3,3-trimethylbenz(e)indolenine intermediate 58 (94 mg, 0.000174 mole), 2 equivalents of dry triethylamine (49 uL), and 5 ml of dry ethanol. After stirring at reflux for 30 min, the reaction mixture was cooled and the crude mobility-modifying dye 21 was precipitated with diethyl ether. The dye 21 was purified by chromatography on silica gel eluting with methanol:CH$_2$Cl$_2$ (1:4), followed by recrystallization from methanol/diethyl ether to give 57 mg of dye 21 as dark blue powder (40 % yield).

5.7 Synthesis of MM-Cy5-NHS Ester (Compound 22)

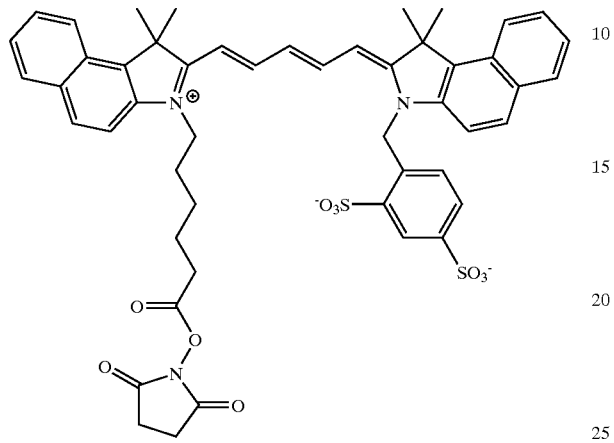

Mobility-modifying cyanine dye 21 (30 mg, 0.00003674 mole), 2 mL of dry dimethyl formamide, 6 equivalents of di-isopropyl ethylamine (40 μl), and 15 equivalents of O-(N-succinimidyl)N,N,N',N'-tetramethyluronium tetrafluoroborate were stirred at room temperature for 15 minutes. The reaction was quenched with 5 % HCI, extracted 3 times with ethyl acetate, and the combined organic layers were washed with brine and concentrated to give crude NHS ester 22 as a blue solid. The NHS ester 22 was purified by chromatography on silica gel eluting with methanol/CH$_2$Cl$_2$/AcOH (15:85:0.1). The purified NHS ester 22 was then recrystallized from methanol/diethyl ether yielding a dark blue powder (27 mg, 80% yield).

5.8 Synthesis of 7-Propargylanino-ddATP (Compound 23)

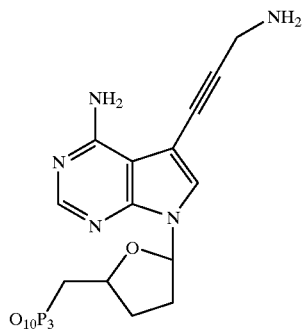

7-Propargylamino-ddATP 23 was synthesized according to the methods described in U.S. Pat. No. 5,151,507.

5.9 Synthesis of MM-Cy5-Labeled Terminator 7-Deaza-ddATP (Compound 24)

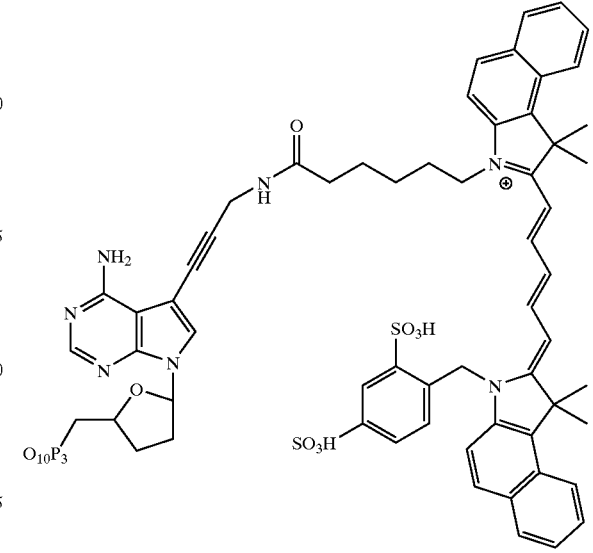

Compound 23 (10 μl of a 30 mM solution in 100 mM TEA-bicarbonate, pH 7.0) was evaporated to dryness. It was then resuspended in 50 μl 250 mM bicarbonate buffer (pH 9.0). A solution of NHS ester 22 (5 μl of a stock of 5 mg/60 μl in dimethyl sulfoxide) was added and stirred in the dark overnight at room temperature. The reaction mixture was purified by HPLC (AX-300 anion exchange). The fractions corresponding to the labeled terminator 24 were concentrated and repurified by HPLC (C-8 reverse phase). The final product was dried in vacuo and diluted with 250 mM CAPSO, pH 9.6.

5.10 Synthesis of Additional Dye-Labeled Terminators

The following additional terminators were synthesized using synthesis strategies similar to those outlined above. The benzorhodamine NHS ester precursors were synthesized as described in U.S. Pat. No. 5,936,087. The extended rhodamine NHS ester precursors were synthesized as described in co pending application Ser. No. 09/325,243, filed Nov. 17, 1998. The various linker-modified ddNTPs were synthesized as described in U.S. Pat. No. 5,821,356 and/or 5,770,716.

Compound 25
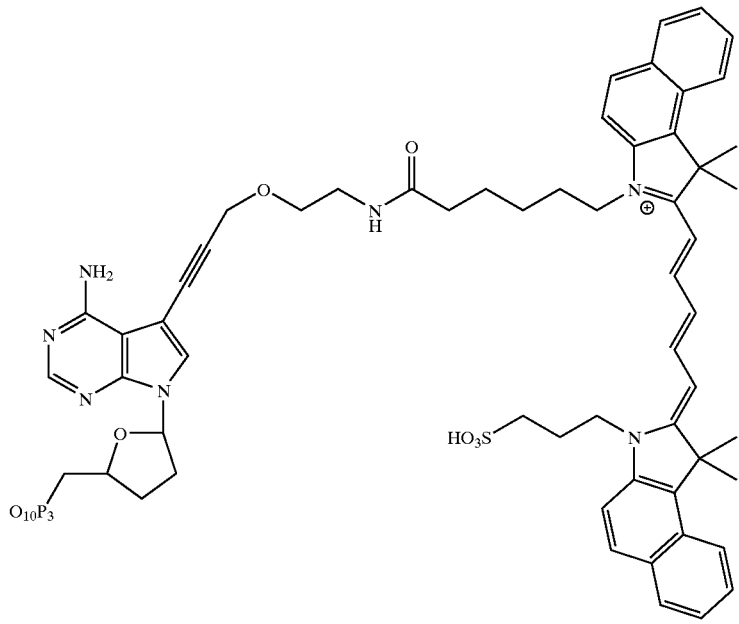
Compound 26
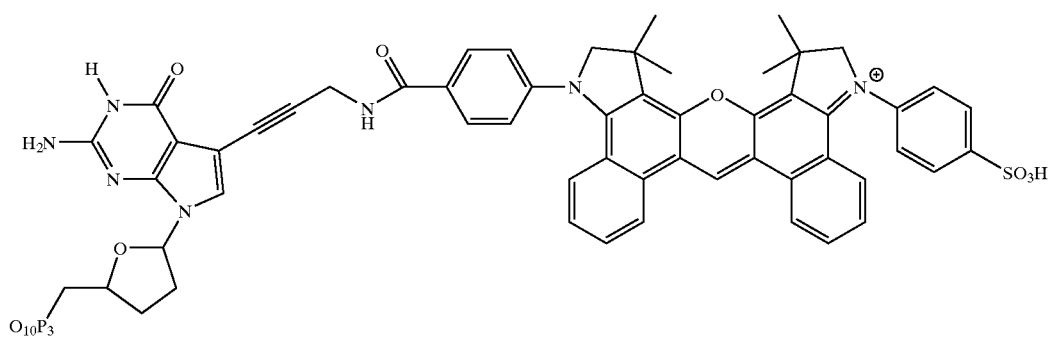
Compound 27
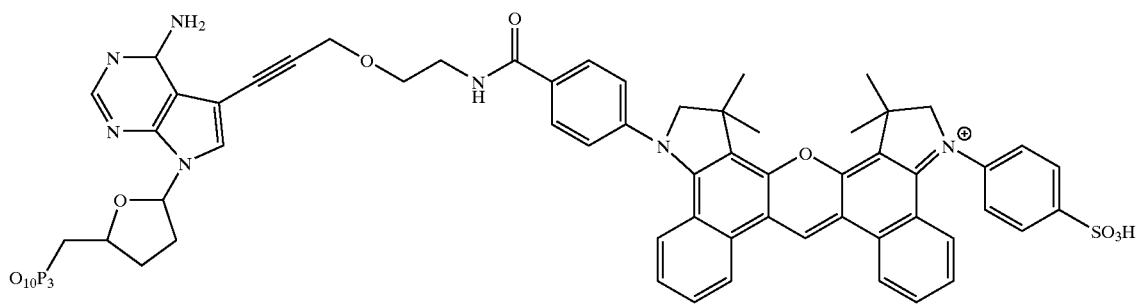
Compound 28
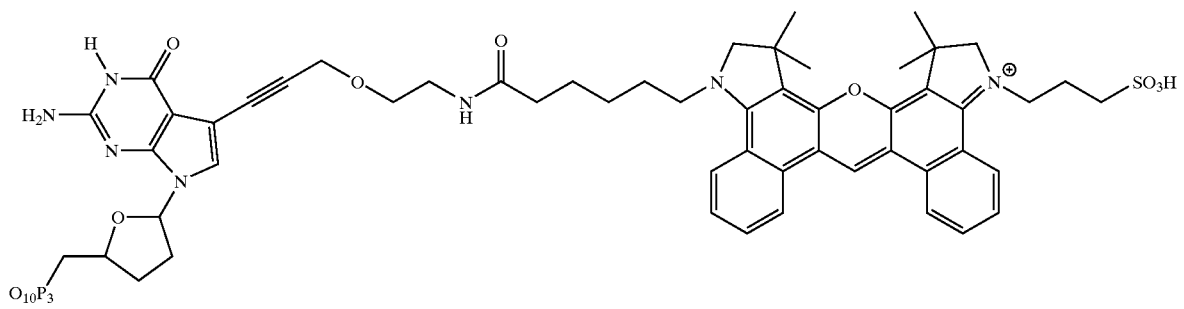

-continued
Compound 29
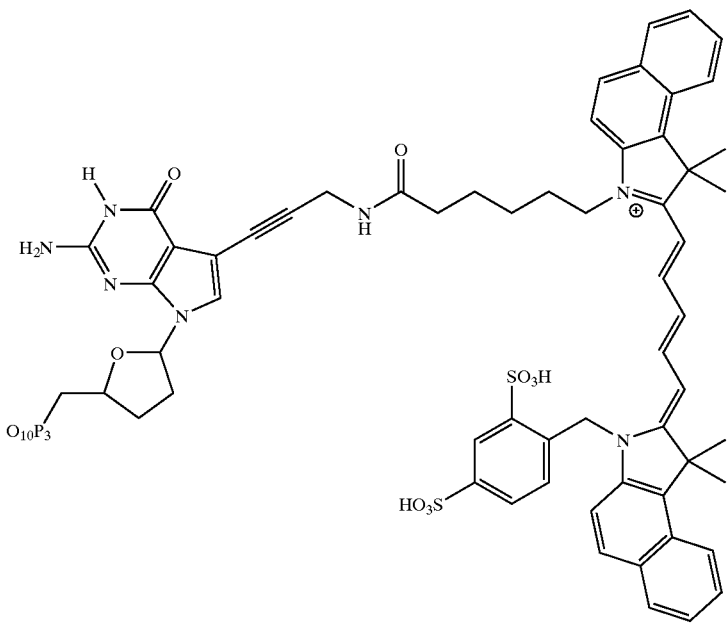
Compound 30
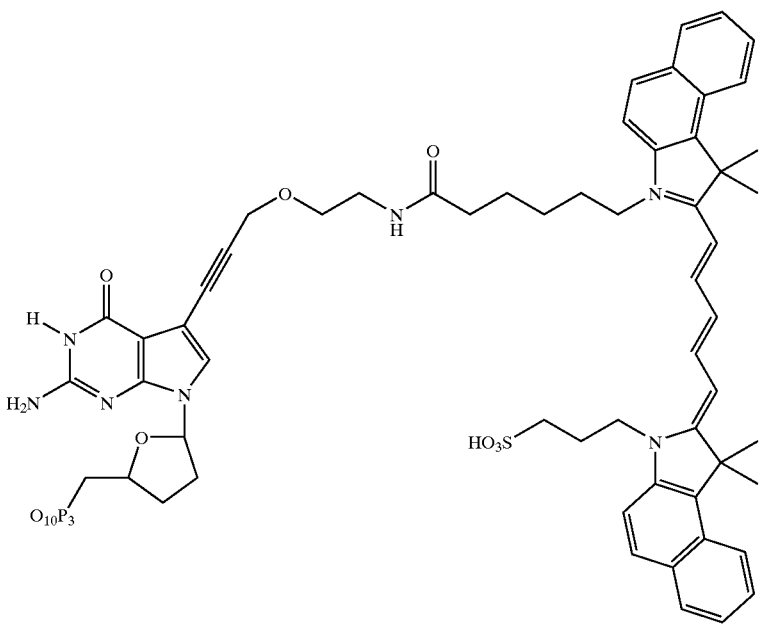
Compound 31
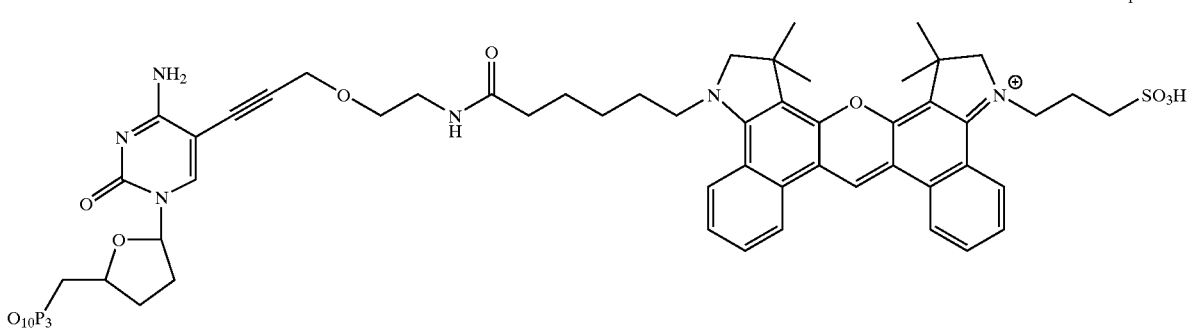

-continued
Compound 32
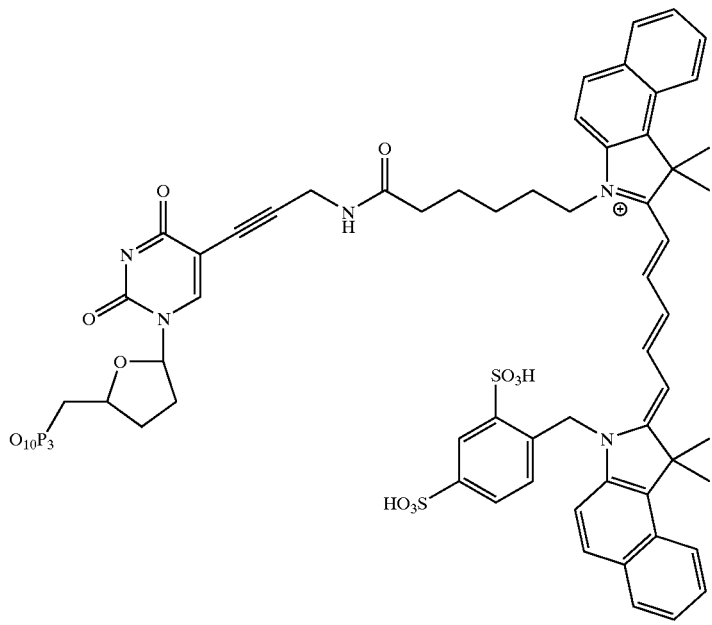
Compound 33
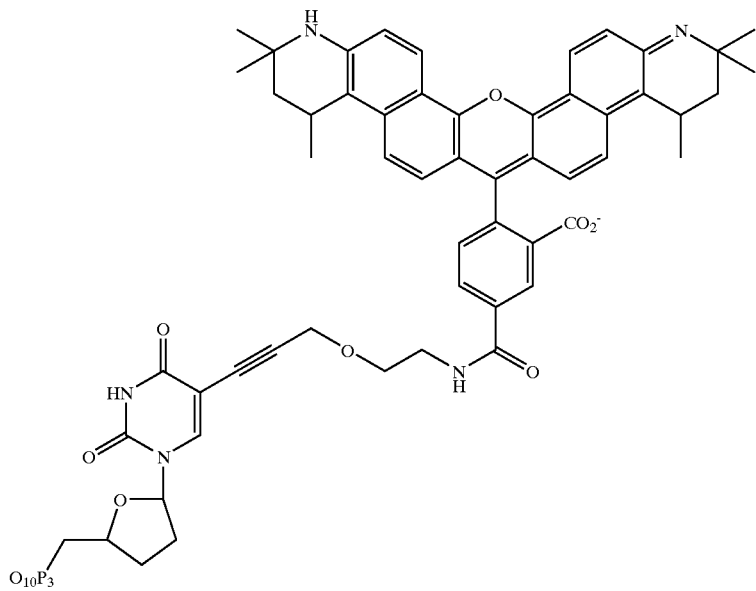

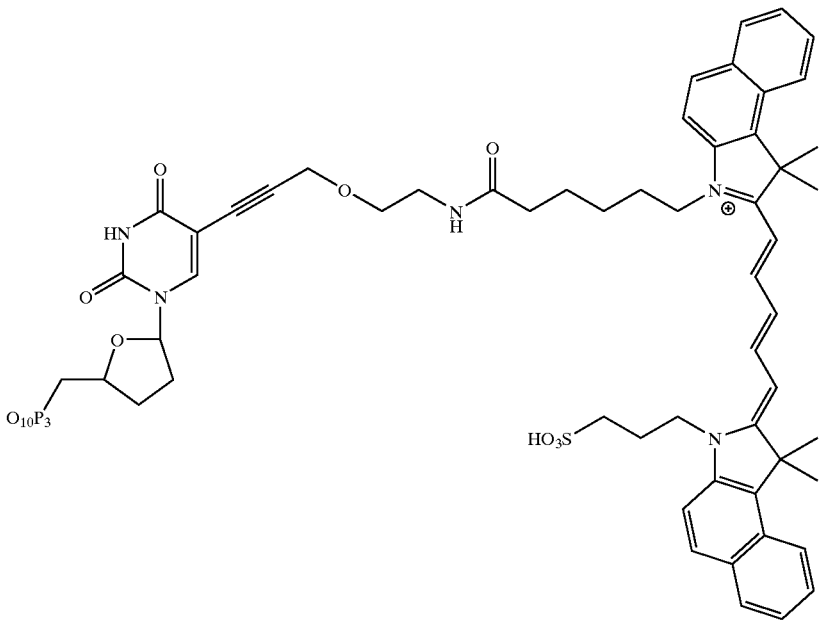

Compound 34

6. EXAMPLE: Terminators Labeled With Mobility-Modifying Dyes of the Invention Act as Substrates for Polymerizing Ernmes Terminators 25, 26, 27, 28, 29, 30, 31, 32, 33 and 34 were used to generate sequencing fragments according to the protocol described in U.S. Pat. No. 5,948,648 (Example 12) or U.S. Pat. No. 5,847,162 (Examples 8–10). Mobility-modifying terminators 29 and 32 retained high biological activity, as evidenced by their efficient incorporation into the terminated fragments.

7. EXAMPLE: The Mobility-Modifying Dyes of the Invention Shift the Relative Electrophoretic Mobilities of Polynucleotides

7.1 Experimental Protocol

The sequencing fragments generated from the sequencing reactions in the previous example were applied to a ABI PRIZM® 310 Genetic Analyzer (PE Biosystems, Foster City, Calif.) modified with a red laser and electrophoresed according to the manufacturers protocol or the protocols described in U.S. Pat. No. 5,948,648 or U.S. Pat. No. 5,847,162.

7.2 Results

The electrophoretic mobilities of fragments labeled with the cyanine dyes relative to those labeled with the rhodamine dyes are tabulated in TABLE 1, below. In the table, a positive (+) shift indicates fragments migrated faster than the standards. A negative (−) shift indicates fragments that migrated slower than the standards.

TABLE 1

Relative Mobilities of Dye-Labeled Sequencing Fragments
Relative Mobilities (Base Units)

|  | +0.5 | 0.0 | −0.5 | −1.0 | −1.5 | −2.0 |
|---|---|---|---|---|---|---|
| Terminator | 26 | 27 |  | 24 |  | 25 |
|  |  | 28 |  | 29 |  | 30 |
|  |  | 31 |  | 32 |  | 34 |
|  |  | 33 |  |  |  |  |

As illustrated in TABLE 1, fragments generated from monosulfonated benzocyanine dye-labeled terminators 25 (ddA), 30 (ddG) and 34 (ddLI) migrate two or more bases slow during electorphoresis relative to DNA fragments generated from dibenzorhodamnine dye (U.S. Pat. No. 5,936,087) labeled terminators 26 (ddGi), 27 (ddA), 28 (ddG), and 31 (ddC), or extended rhodamine dye (U.S. application Ser. No. 09/325,243; attorney docket no. 4446) labeled terminator 33 (ddLT). Mobility-modifying the monosulfonated dye according the the invention by replacing the monosulfonate group with a bis-sulfonated mobility-modifying moiety increases the relative electrophoretic mobilties of polynucleotide fragments labeled with the mobility-modi[]ig dye by one base, as demonstrated by labeled fragments generated with terrinnators 24 (ddA), 29 (ddG) and 32 (ddC).

All publications, patents and patent applications mentioned in this specification are herein incorporated by reference to the same extent as if each individual publication, patent or patent application was specifically and individually indicated to be incorporated by reference.

The invention now having been fuilly described, it will be apparent to one of ordinary skill in the art that many changes and modifications can be made thereto without departing from the spirit or scope of the appended claims.

We claim:

1. A mobility-modifying cyanine dye comprising a compound of the formula (I.I):

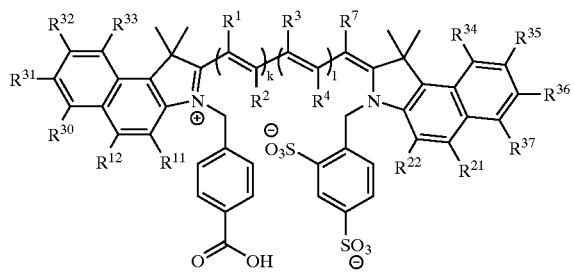

wherein

R¹, R²l R³, R⁴ and R⁷ are each independently hydrogen, halogen, —F, —Cl, —CN, —CF₃, ($C_1$–$C_6$) alkyl, ($C_5$–$C_{14}$) aryl or 5-membered heteroaryl;

$R^{11}$, $R^{12}$, $R^{21}$, $R^{22}$, $R^{30}$, $R^{31}$, $R^{32}$, $R^{33}$, $R^{34}$, $R^{35}$, $R^{36}$, and $R^{37}$ are each independently hydrogen, —S(O)₂O⁻ or —O—S(O)₂O⁻;

k is an integer from 0 to 1; and l is an integer from 0 to 1.

2. The mobility-modifying cyanine dye of claim 1 wherein the sum of k and l is 2.

3. The mobility-modifying cyanine dye of claim 2 wherein R¹, R², R³, R⁴ and R⁷ are hydrogen.

4. The mobility-modifying cyanine dye of claim 3 wherein $R^{11}$, $R^{12}$, $R^{21}$ and $R^{22}$ are hydrogen;

at most two of $R^{30}$, $R^{31}$, $R^{32}$ and $R^{33}$ are independently selected from the group consisting of —S(O)₂O⁻ and —OS(O)₂O⁻; and at most two of $R_{34}$, $R_{35}$, $R^{36}$ and $R^{37}$ are independently selected from the group consisting of —S(O)₂O⁻ and —OS(O)₂O⁻.

5. The mobility-modifying cyanine dye of claim 4 wherein $R^{11}$, $R^{12}$, $R^{21}$, $R^{22}$, $R^{30}$, $R^{31}$, $R^{32}$, $R^{33}$, $R^{34}$, $R^{35}$, $R^{36}$ and $R^{37}$ are hydrogen.

* * * * *